United States Patent
Wang et al.

(10) Patent No.: US 9,644,004 B2
(45) Date of Patent: May 9, 2017

(54) PEPTIDE AND PEPTIDOMIMETIC INHIBITORS

(71) Applicant: Ra Pharmaceuticals, Inc., Cambridge, MA (US)

(72) Inventors: Zhaolin Wang, Wellesley, MA (US); Ping Ye, Lexington, MA (US); Alonso Ricardo, Cambridge, MA (US); Kristopher Josephson, Wayland, MA (US); Paul Anderson, Larchmont, NY (US); Michelle Denise Arata, Malden, MA (US); Zhong Ma, Lexington, MA (US); Nathan Ezekiel Nims, Winchester, MA (US); Eberhard Schneider, Denkte (DE); Gregor Schurmann, Hannover (DE); Peter Wagner, Denkte (DE); Douglas A. Treco, Arlington, MA (US); Hong Zheng, Brighton, MA (US); Daniel Elbaum, Newton, MA (US); Nicolas Cedric Boyer, Somerville, MA (US)

(73) Assignee: Ra Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/962,457

(22) Filed: Dec. 8, 2015

(65) Prior Publication Data

US 2016/0083430 A1  Mar. 24, 2016

Related U.S. Application Data

(63) Continuation of application No. 14/401,697, filed as application No. PCT/US2013/031265 on Mar. 14, 2013, now Pat. No. 9,238,676.

(60) Provisional application No. 61/648,155, filed on May 17, 2012.

(51) Int. Cl.
| | | |
|---|---|---|
| *A61K 38/00* | (2006.01) | |
| *C07K 9/00* | (2006.01) | |
| *C07K 7/08* | (2006.01) | |
| *A61K 47/48* | (2006.01) | |
| *C08G 65/48* | (2006.01) | |
| *A61K 38/10* | (2006.01) | |
| *A61K 45/06* | (2006.01) | |

(52) U.S. Cl.
CPC .............. *C07K 7/08* (2013.01); *A61K 38/10* (2013.01); *A61K 45/06* (2013.01); *A61K 47/48215* (2013.01); *C08G 65/48* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 5,427,908 A | 6/1995 | Dower et al. | |
| 5,436,138 A | 7/1995 | Duronio et al. | |
| 5,580,717 A | 12/1996 | Dower et al. | |
| 5,585,353 A | 12/1996 | Merrifield et al. | |
| 5,596,078 A | 1/1997 | Andersson et al. | |
| 5,643,768 A | 7/1997 | Kawasaki | |
| 5,658,754 A | 8/1997 | Kawasaki | |
| 5,726,287 A | 3/1998 | Andersson et al. | |
| 5,750,344 A | 5/1998 | Doyle | |
| 5,780,221 A | 7/1998 | Schumacher et al. | |
| 5,834,318 A | 11/1998 | Buettner | |
| 5,843,701 A | 12/1998 | Gold et al. | |
| 5,910,437 A | 6/1999 | Kent et al. | |
| 5,990,273 A | 11/1999 | Andersson et al. | |
| 6,040,133 A | 3/2000 | Kent et al. | |
| 6,057,098 A | 5/2000 | Buechler et al. | |
| 6,194,183 B1 | 2/2001 | Markvardsen et al. | |
| 6,258,558 B1 | 7/2001 | Szostak et al. | |
| 6,261,804 B1 | 7/2001 | Szostak et al. | |
| 6,303,344 B1 | 10/2001 | Patten et al. | |
| 6,333,402 B1 | 12/2001 | Markland et al. | |
| 6,361,943 B1 | 3/2002 | Yanagawa et al. | |
| 6,716,973 B2 | 4/2004 | Baskerville et al. | |
| 6,720,472 B2 | 4/2004 | Chada et al. | |
| 6,962,781 B1 | 11/2005 | Williams | |
| 7,135,279 B2 | 11/2006 | Kent et al. | |
| 7,244,701 B2 | 7/2007 | Larsen et al. | |
| 7,314,974 B2 | 1/2008 | Cao et al. | |
| 7,744,910 B2 | 6/2010 | Gschneidner et al. | |
| 8,415,305 B2 | 4/2013 | Krastel et al. | |
| 8,546,326 B2 | 10/2013 | Joabsson et al. | |
| 8,637,454 B2 | 1/2014 | Sternlicht | |
| 2002/0160433 A1* | 10/2002 | Welch ................ C07K 16/1232 435/7.37 |
| 2008/0313749 A1 | 12/2008 | Timmerman et al. | |
| 2010/0183625 A1 | 7/2010 | Sternlicht | |
| 2011/0172126 A1 | 7/2011 | Brust | |
| 2012/0101253 A1 | 4/2012 | Heinis et al. | |

FOREIGN PATENT DOCUMENTS

| | | |
|---|---|---|
| EP | 0036676 | 9/1981 |
| EP | 0052322 | 4/1983 |

(Continued)

OTHER PUBLICATIONS

Abuchowski, A. et al, (1977) Effect of covalent attachment of polyethylene glycol on immunogenicity and circulating life of bovine liver catalase, J. Biol. Chem., 252, 3582.

(Continued)

*Primary Examiner* — Jeanette Lieb
(74) *Attorney, Agent, or Firm* — DT WARD, PC; Donna T. Ward; Christopher P. Sullivan

(57) ABSTRACT

The present invention provides inhibitors and/or antagonists of plasma kallikrein. Also provided are methods of utilizing the inhibitors as therapeutics.

20 Claims, No Drawings

(56) References Cited

FOREIGN PATENT DOCUMENTS

| | | |
|---|---|---|
| EP | 0088046 | 11/1984 |
| EP | 0143949 | 6/1985 |
| EP | 1312680 | 5/2003 |
| WO | 94/01451 | 1/1994 |
| WO | 96/34879 | 11/1996 |
| WO | 97/13522 | 4/1997 |
| WO | 02/103024 | 12/2002 |
| WO | 03/040168 | 5/2003 |
| WO | 2004077062 | 9/2004 |
| WO | 2009/067191 | 5/2009 |
| WO | 2013050615 | 4/2013 |

OTHER PUBLICATIONS

Baeriswyl et al. (2012) Bicyclic peptides with optimized ring size inhibit human plasma kallikrein and its orthologues while sparing paralogous proteases. ChemMedChem. 7(7):1173-6.

Baggio, R. et al. (2002) Identification of epitope-like consensus motifs using mRNA display, J. Mol. Recog. 15:126-134.

Baskerville, S. and Bartel, D.P. (2002) A ribozyme that ligates RNA to protein, Proc. Natl. Acad. Sci. USA 99:9154-9159.

Berman, H.M. et al., (2000) The Protein Data Bank, Nucleic Acids Research, 28: 235-242.

Blackwell, H. E. and Grubbs, R. H. (1998) Highly Efficient Synthesis of Covalently Cross-Linked Peptide Helices by Ring-Closing Metathesis, Angew. Chem., Int. Ed. 37, 3281-3284.

Bracken, et al. (1994) Synthesis and Nuclear Magnetic Resonance Structure Determination of an .alpha.-Helical, Bicyclic, Lactam-Bridged Hexapeptide, J. Am. Chem. Soc., 116, 6431-6432.

Cantel et al. (2008) Synthesis and conformational analysis of a cyclic peptide obtained via i to i+4 intramolecular side-chain to side-chain azide-alkyne 1,3-dipolar cycloaddition, J. Org. Chem., 73 (15), 5663-5674.

Clermont, A. et al. (2011) Plasma kallikrien mediates retinal vascular dysfunction and induces retinal thickening in diabetic rats. Diabetes. 60:1590-8.

Coin, I et al. (2007) Solid-phase peptide synthesis: from standard procedures to the synthesis of difficult sequences, Nature Protcols 2(12):3247-56.

Cwirla, S.E. et al. (1990) Peptides on phage: a vast library of peptides for identifying ligands, Proc. Natl. Acad. Sci. U.S.A. 87:6378-6382.

Dedkova, L. et al. (2003) Enhanced D-amino acid incorporation into protein by modified ribosomes, J. Am. Chem. Soc. 125: 6616-6617.

Dennis et al. (2002) Albumin binding as a general strategy for improving the pharmokinetics of proteins. J Biol Chem. 277(38): 35035-43.

Devlin, J.J., et. al., (1990). Random peptide libraries: a source of specific protein binding molecules, Science 249, 404-406.

Dooley, C.T. et al., "An All D-Amino Acid Opioid Peptide with Central Analgesic Activity from a Combinatorial Library," Science, vol. 266:2019-2022 (1994).

Dooley, C.T. et al., "New, potent N-acetylated in D-amino acid opioid peptides," Peptides: Chemistry, Structure and Biology. Proceedings of the 13th American Peptide Symposium (RS Hodges and JA Smith, Eds.) ESCOM, Leiden, pp. 984-985, (1994).

Fisher, Phyllis J. et al., "Calmodulin interacts with amphiphilic peptides composed of all D-amino acids," Nature, vol. 368:651-653 (1994).

Forster, A.C. et al. (2003) Programming peptidomimetic syntheses by translating genetic codes designed de novo, Proc. Natl. Acad. Sci. USA 100: 6353-6357.

Frankel, A. et al., (2003) Encodamers: unnatural peptide oligomers encoded in RNA, Chem. Biol. 10:1043-1050.

Gao, G. et al., (2003) Kallikrein-binding protein inhibits retinal neovascularization and decreases vascular leakage. Diabetologia. 46:689-98.

Goettig, P. et al., (2010) Natural and synthetic inhibitors of kallikrein-related peptidases (KLKs). Biochimie. 92:1546-67.

Harikumar, et al. (2004) Measurement of intermolecular distances for the natural agonist Peptide docked at the cholecystokinin receptor expressed in situ using fluorescence resonance energy transfer, Mol Pharmacol 65:28-35.

Hartman et al., (2006) Enzymatic aminoacylation of tRNA with unnatural amino acids, Proc. Natl. Acad. Sci. USA 103:4356-4361.

Hartman, M.C.T. et al. (2007) An expanded set of amino acid analogs for the ribosomal translation of unnatural peptides, PLoS ONE 2:e972.

He, M and Taussig, M (2002). Briefs in Functional Genomics and Proteomics. 1(2): 204-212.

Heinis, C. et al., (2009) Phage-encoded combinatorial chemical libraries based on bicyclic peptides. Nat Chem Biol. 5(7):502-7.

Horisawa, K. et al., (2008) Use of cDNA tiling arrays for identifying protein interactions selected by in vitro display technologies, PLoS ONE Feb. 20; 3(2):e1646.

Hwang et al. (1980) Hepatic uptake and degradation of unilamellar sphingomyelin/cholesterol liposomes: a kinetic study, Proc. Natl. Acad. Sci. USA 77: 4030-4034.

Jackson, R.J., et al., (2001) Development of a tRNA-dependent in vitro translation system, RNA 7:765-773.

Johansson (2006) Choosing reporter-quencher pairs for efficient quenching through formation of intramolecular dimers, Methods Mol. Biol. 335:17-29.

Johansson (2005) Fluorescence approaches for determining protein conformations, interactions and mechanisms at membranes, Traffic. 6(12):1078-92.

Karlin and Altschul (1990) Methods for assessing the statistical significance of molecular sequence features by using general scoring schemes, Proc. Natl. Acad. Sci. USA 87:2264-68.

Karlin and Altschul (1993) Applications and statistics for multiple high-scoring segments in molecular sequences, Proc. Natl. Acad. Sci. USA 90:5873-77.

Kay, B.K. et al. (2001) Screening phage-displayed combinatorial peptide libraries, Methods. 24:240-246.

Keefe, A D. (2001) Protein selection using mRNA display, Curr Protoc Mol Biol. May; Chapter 24:Unit 24.5.

Keefe, A.D. and Szostak, J.W. (2001) Functional proteins from a random-sequence library, Nature 15:715-718.

Lam, KitS. et al., (1993) Discovery of D-amino-acid-containing ligands with selectide technology, Gene, vol. 137:13-16.

Lea, W.A. et al., (2011) Fluorescence polarization assays in small molecule screening. Expert Opin Drug Discov. Jan;6(1):17-32.

Levengood, M.R. and Van der Donk, W.A., (2008) Use of lantibiotic synthetases for the preparation of bioactive constrained peptides, Bioorg. and Med. Chem. Lett. 18:3025-3028.

Liu, R. et al. (2000). Optimized synthesis of RNA-protein fusions for in vitro protein selection, Methods Enzymol. 318:268-293.

Markland, W. et al., (1996) Iterative optimization of high-affinity protease inhibitors using phage display. 2. plasma kallikrein and thrombin. Biochemistry. 35(24):8058-67.

Milward, S.W. et al., (2005) A general route for post-translational cyclization of mRNA display libraries, J. Am. Chem. Soc. 127:14142-14143.

Morris, C.J. (2003) Carrageenan-induced paw edema in the rat and mouse. Methods in Molecular Biology. Humana Press Inc., Totowa, NJ. vol. 225, Chapter 13, p. 115-21.

Murakami, H. et al. (2006) A highly flexible tRNA acylation method for non-natural polypeptide synthesis, Nat. Methods 3:357-359.

Neininger et al. (2001) FRET-based detection of different conformations of MK2, EMBO Reports. 2(8):703-708.

Nemoto, H. et al., (1997) In vitro virus: bonding of mRNA bearing puromycin at the 3'-terminal end to the C-terminal end of its encoded protein on the ribosome in vitro, FEBS Lett. 414:405-408.

Oliva, B. et al. (1997) An automated classification of the structure of protein loops, J Mol Biol. Mar. 7;266(4):814-30.

Pepinsky et al., (2001) Improved pharmacokinetic properties of a polyethylene glycol-modified form of interferon-beta-1a with preserved in vitro bioactivity, JPET, 297, 1059.

(56) References Cited

OTHER PUBLICATIONS

Ripka, A.S. et al., (1998) Synthesis of novel cyclic protease inhibitors using grubbs olefin metathesis. Bioorg Med Chem Lett. 8(4):357-60.

Prystay, L. et al., (2001) Determination of equilibrium dissociation constants in fluorescence polarization. J Biomol Screen. Jun;6(3):141-50.

Communication and Supplementary Partial European Search Report for EP Application No. 13790527.9 dated Jul. 22, 2016 (7 pages).

Risseeuw, M.D.P., (2009) Alkylated and bicyclic sugar amino acids: synthesis and applications. Doctoral Thesis, Leiden University. Chapter 1, p. 9-26.

Roberts, R.W., and Szostak, J.W. (1997) RNA-peptide fusions for the in vitro selection of peptides and proteins, Proc. Natl. Acad. Sci. USA 94, 12297-12302.

Rothe, A. et al. (2006) In vitro display technologies reveal novel biopharmaceutics, The FASEB Journal. 20 (10):1599-1610.

Sando, S. et al., (2007) Unexpected preference of the *E. coli* translation system for the ester bond during incorporation of backbone-elongated substrates, J. Am. Chem. Soc. 129:6180-6186.

Schlippe, et al. (2012) In vitro selection of highly modified cyclic peptides that act as tight binding inhibitors. J Am Chem. 134:10469-77.

Schafmeister and Verdine (2000) An All-Hydrocarbon Cross-Linking System for Enhancing the Helicity and Metabolic Stability of Peptides, J. Am. Chem. Soc., 122 (24), 5891-5892.

Scott et al. (1999) Production of cyclic peptides and proteins in vivo, PNAS. vol. 96 No. 24 p. 13638-13643.

Seebeck, F.P. and Szostak, J.W. (2006) Ribosomal synthesis of dehydroalanine-containing peptides J. Am. Chem. Soc. Jun 7;128(22):7150-1.

Sergeeva, A. et al. (2006). Display technologies: application for the discovery of drug and gene delivery agents, Adv. Drug Deliv. Rev. 58:1622-1654.

Shimizu, Y. et al. (2001) Cell-free translation reconstituted with purified components, Nat. Biotech. 19:751-755.

Smith(1994) Oxygen-induced retinopathy in the mouse, Investigative Ophthalmology & Visual Science 35: 101-111.

Smith, A. B. 3rd, et al. (1994) De Novo Design, Synthesis, and X-ray Crystal Structures of Pyrrolinone-Based .beta.-Strand Peptidomimetics, J. Am. Chem. Soc. 116:9947-9962.

Takashashi, T.T et al. (2003) mRNA display: ligand discovery, interaction analysis and beyond, Trends in Biochem. Sci. 28(3):159-165.

Timmerman, P. et al., (2005) Rapid and quantitative cyclization of multiple peptide loops onto synthetic scaffolds for structural mimicry of protein surfaces, ChemBioChem 6:821-824.

Valencia et al. (2008) mRNA-display-based selections for proteins with desired functions: a protease-substrate case study, Biotechnol Prog. May-Jun.; 24(3):561-9.

Wieder et al., (1979) Some properties of polyethylene glycol:phenylalanine ammonia-lyase adducts, J. Biol. Chem. 254, 12579.

Yamagishi, Y. et al., (2011) Natural product-like macrocyclic N-methyl peptide inhibitors against a ubiquitin ligase uncovered from a ribosome-expressed de novo library.

Zhang(2004) Plasminogen kringle 5 reduces vascular leakage in the retina in rat models of oxygen-induced retinopathy and diabetes, Diabetologia 47: 124-131.

Zuraw, B.L. et al., (2008) Clinical practice. Hereditary angioedema. NEJM. 359(10):1027-36.

International Search Report for PCT/US2013/031265 dated Jun. 18, 2013.

Extended European Search Report for corresponding EP application No. 13790527.9 dated Nov. 12, 2015.

Lehmann A: "Ecallantide (DX-88), a plasma 10 kallikrein inhibitor for the treatment of hereditary angioedema and the prevention of blood loss in on-pump cardiothoracic surgery", Expert Opinion on Biological Therapy, Informa Healthcare, Ashley, London: GB, vol. 8, No. 8, Aug. 1, 2008 (Aug. 1, 2008), pp. 1187-1199.

V. Baeriswyl, et al., "Phage selection of cyclic peptide antagonists with increased stability toward intestinal proteases", Protein Engineering Design and Selection, vol. 26, No. 1, Oct. 24, 2012 (Oct. 24, 2012), pp. 81-89.

\* cited by examiner

SEQUENCE LISTING

```
<160> NUMBER OF SEQ ID NOS: 245

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Cys Asn Tyr Trp Ser Pro Trp Thr Glu Cys Ser Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Cys Glu Ser Ile Cys Arg Val Leu Arg Tyr Ser Glu
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(11)
<223> OTHER INFORMATION: dibromoxylene linker between residues
<220> FEATURE:
<223> OTHER INFORMATION: C-term NH2
```

```
<400> SEQUENCE: 3

Met Cys Asn Tyr Trp Ser Pro Trp Thr Glu Cys Ser Arg
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 4

Met Cys Glu Ser Ile Cys Arg Val Leu Arg Tyr Ser Glu
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 5

Met Cys Glu Thr Ile Cys Arg Val Leu Lys Tyr Ser Asp
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 6

Met Cys Glu Ser Ile Cys Arg Val
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2
```

<400> SEQUENCE: 7

Met Cys Glu Ser Ile Cys Arg Val
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 8

Met Cys Glu Ser Ile Cys Arg Val
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nvl
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 9

Val Cys Glu Ser Ile Cys Arg Val
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (8)..(8)
<223> OTHER INFORMATION: Tbg
<220> FEATURE:
<223> OTHER INFORMATION: C-term NH2

<400> SEQUENCE: 10

Met Cys Glu Ser Ile Cys Arg Gly
1               5

<210> SEQ ID NO 11
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: trans-butenyl linker between residues
<220> FEATURE:
<223> OTHER INFORMATION: C-term NH2

<400> SEQUENCE: 11

Met Cys Glu Ser Ile Cys Arg Val
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (5)..(5)
<223> OTHER INFORMATION: Phg
<220> FEATURE:
<223> OTHER INFORMATION: C-term NH2

<400> SEQUENCE: 12

Met Cys Glu Ser Gly Cys Arg Val
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nvl
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (5)..(5)
<223> OTHER INFORMATION: Phg
<220> FEATURE:
<221> NAME/KEY: MOD_RES
<222> LOCATION: (8)..(8)
<223> OTHER INFORMATION: Tbg
<220> FEATURE:
<223> OTHER INFORMATION: C-term NH2

<400> SEQUENCE: 13

Val Cys Glu Ser Gly Cys Arg Gly
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 14

Met Cys Glu Ser Ile Cys Arg Val Asn
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 15

Met Cys Glu Ser Ile Cys Arg
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 16

Met Cys Glu Ser Ile Cys Arg Ala
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 17

Met Cys Glu Ser Ala Cys Arg Val
1               5

<210> SEQ ID NO 18
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 18

Met Cys Glu Ala Ile Cys Arg Val
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (4)..(4)
<223> OTHER INFORMATION: nMeS
<220> FEATURE:
<223> OTHER INFORMATION: C-term NH2

<400> SEQUENCE: 19

Met Cys Glu Ser Ile Cys Arg Val
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (3)..(3)
<223> OTHER INFORMATION: Asp(T)
<220> FEATURE:
<223> OTHER INFORMATION: C-term NH2

<400> SEQUENCE: 20

Met Cys Xaa Ser Ile Cys Arg Val
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nvl
<220> FEATURE:
<221> NAME/KEY: misc_feature
<222> LOCATION: (2)..(6)
<223> OTHER INFORMATION: dibromoxylene linker between residues
<220> FEATURE:
```

```
<221> NAME/KEY: MOD_RES
<222> LOCATION: (7)..(7)
<223> OTHER INFORMATION: Phe(4CH2NH2)
<220> FEATURE:
<223> OTHER INFORMATION: C-term NH2

<400> SEQUENCE: 21

Val Cys Glu Ser Ile Cys Phe Val
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nvl
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (7)..(7)
<223> OTHER INFORMATION: Phe(3CH2NH2)
<220> FEATURE:
<223> OTHER INFORMATION: C-term NH2

<400> SEQUENCE: 22

Val Cys Glu Ser Ile Cys Phe Val
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<223> OTHER INFORMATION: C-term NH2

<400> SEQUENCE: 23

Cys Glu Ser Ile Cys Arg Val
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 24

Met Cys Ala Ser Ile Cys Arg Val
```

1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 25

Ala Cys Glu Ser Ile Cys Arg Val
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (5)..(5)
<223> OTHER INFORMATION: nMeI
<220> FEATURE:
<223> OTHER INFORMATION: C-term NH2

<400> SEQUENCE: 26

Met Cys Glu Ser Ile Cys Arg Val
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (3)..(3)
<223> OTHER INFORMATION: nMeE
<220> FEATURE:
<223> OTHER INFORMATION: C-term NH2

<400> SEQUENCE: 27

Met Cys Glu Glu Ser Ile Cys Arg Val
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: misc_feature
<222> LOCATION: (2)..(6)
<223> OTHER INFORMATION: hexyltetrazolyl-dibromoxylene linker between
      residues
<220> FEATURE:
<223> OTHER INFORMATION: C-term NH2

<400> SEQUENCE: 28

Met Cys Glu Ser Ile Cys Arg Val
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nvl
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (7)..(7)
<223> OTHER INFORMATION: hLys
<220> FEATURE:
<223> OTHER INFORMATION: C-term NH2

<400> SEQUENCE: 29

Val Cys Glu Ser Ile Cys Lys Val
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nvl
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (5)..(5)
<223> OTHER INFORMATION: Phg
<220> FEATURE:
<221> NAME/KEY: MOD_RES
<222> LOCATION: (8)..(8)
<223> OTHER INFORMATION: Tbg
<220> FEATURE:
<223> OTHER INFORMATION: C-term NH2

<400> SEQUENCE: 30

Val Cys Glu Pro Gly Cys Arg Gly
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (1)..(1)
<223> OTHER INFORMATION: Nvl
<220> FEATURE:
<221> NAME/KEY: MOD_RES
<222> LOCATION: (2)..(2)
<223> OTHER INFORMATION: Pen
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 31

Val Xaa Glu Ser Ile Cys Arg Val
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nvl
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (6)..(6)
<223> OTHER INFORMATION: Pen
<220> FEATURE:
<223> OTHER INFORMATION: C-term NH2

<400> SEQUENCE: 32

Val Cys Glu Ser Ile Xaa Arg Val
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nvl
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (7)..(7)
<223> OTHER INFORMATION: hLys
<220> FEATURE:
<223> OTHER INFORMATION: C-term NH2

<400> SEQUENCE: 33

Val Cys Glu Ser Ile Cys Lys Val
1               5
```

```
<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nvl
<220> FEATURE:
<221> NAME/KEY: MOD_RES
<222> LOCATION: (2)..(2)
<223> OTHER INFORMATION: Pen
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (6)..(6)
<223> OTHER INFORMATION: Pen
<220> FEATURE:
<223> OTHER INFORMATION: C-term NH2

<400> SEQUENCE: 34

Val Xaa Glu Ser Ile Xaa Arg Val
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nvl
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 35

Val Cys Glu Ser Ile Cys Arg Phe
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
```

```
<223> OTHER INFORMATION: C-term NH2

<400> SEQUENCE: 36

Cys Ala Ser Gly Cys Arg Gly
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(4)
<223> OTHER INFORMATION: dibromoxylene linker between residues
<220> FEATURE:
<223> OTHER INFORMATION: C-term NH2

<400> SEQUENCE: 37

Cys Ser Ile Cys Arg Val
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<223> OTHER INFORMATION: C-term NH2

<400> SEQUENCE: 38

Cys Glu Ser Ile Cys Arg Val Leu Lys
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 39

Cys Ala Ser Gly Cys Arg Gly
1               5
```

```
<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 40

Met Cys Glu Ser Ile Cys Lys Val
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Heptanoyl
<220> FEATURE:
<221> NAME/KEY: misc_feature
<222> LOCATION: (1)..(5)
<223> OTHER INFORMATION: dibromoxylene linker between residues
<220> FEATURE:
<223> OTHER INFORMATION: C-term NH2

<400> SEQUENCE: 41

Cys Glu Ser Ile Cys Arg Val
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: ortho-xylyl linker between residues
<220> FEATURE:
<223> OTHER INFORMATION: C-term NH2

<400> SEQUENCE: 42

Met Cys Glu Ser Ile Cys Arg Val
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: para-xylyl linker between residues
<220> FEATURE:
<223> OTHER INFORMATION: C-term NH2

<400> SEQUENCE: 43
```

```
Met Cys Glu Ser Ile Cys Arg Val
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: mLutidine linker between residues
<220> FEATURE:
<223> OTHER INFORMATION: C-term NH2

<400> SEQUENCE: 44

Met Cys Glu Ser Ile Cys Arg Val
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<223> OTHER INFORMATION: C-term NH2

<400> SEQUENCE: 45

Cys Glu Ser Ile Cys Arg Val Leu
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<223> OTHER INFORMATION: C-term NH2

<400> SEQUENCE: 46

Cys Glu Ser Ile Cys Arg Val Leu Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
```

```
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: D-Ala
<220> FEATURE:
<223> OTHER INFORMATION: C-term NH2

<400> SEQUENCE: 47

Cys Ala Ser Ile Cys Arg Val
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (4)..(4)
<223> OTHER INFORMATION: Tbg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 48

Cys Ala Ser Gly Cys Arg Gly
1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(3)
<223> OTHER INFORMATION: dibromoxylene linker between residues
<220> FEATURE:
<223> OTHER INFORMATION: C-term NH2

<400> SEQUENCE: 49

Cys Ile Cys Arg Val
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

```
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (5)..(5)
<223> OTHER INFORMATION: Chg
<220> FEATURE:
<223> OTHER INFORMATION: C-term NH2

<400> SEQUENCE: 50

Met Cys Glu Ser Gly Cys Arg Val
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<223> OTHER INFORMATION: C-term NH2

<400> SEQUENCE: 51

Cys Glu Ser Ile Cys Arg Val
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (3)..(3)
<223> OTHER INFORMATION: Sar
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 52

Cys Ala Xaa Gly Cys Arg Gly
1               5

<210> SEQ ID NO 53
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (6)..(6)
<223> OTHER INFORMATION: Phe(4CH2NH2)
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 53

Cys Ala Ser Gly Cys Phe Gly
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nvl
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (7)..(7)
<223> OTHER INFORMATION: Eta-omega methylated Arg
<220> FEATURE:
<223> OTHER INFORMATION: C-term NH2

<400> SEQUENCE: 54

Val Cys Glu Ser Ile Cys Arg Val
1               5

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<223> OTHER INFORMATION: C-term NH2

<400> SEQUENCE: 55

Cys Glu Ser Ile Cys Arg Val Leu Arg Tyr
1               5                   10
```

```
<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<223> OTHER INFORMATION: C-term NH2

<400> SEQUENCE: 56

Cys Glu Ser Ile Cys Arg Val Leu Arg Tyr Ser
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<223> OTHER INFORMATION: C-term NH2

<400> SEQUENCE: 57

Cys Glu Ser Ile Cys Arg Val Leu Arg Tyr Ser Glu
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 58

Cys Ala Pro Gly Cys Arg Gly
1               5

<210> SEQ ID NO 59
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 59

Cys Ala Ser Phe Cys Arg Gly
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: (D)Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 60

Cys Ala Ser Gly Cys Arg Gly
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: Phg
<220> FEATURE:
```

```
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 61

Cys Ala Ser Gly Cys Arg Gly
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: Cppg
<220> FEATURE:
<223> OTHER INFORMATION: C-term NH2

<400> SEQUENCE: 62

Cys Ala Ser Gly Cys Arg Val
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: D-Ala
<220> FEATURE:
<223> OTHER INFORMATION: C-term NH2

<400> SEQUENCE: 63

Cys Ala Ser Val Cys Arg Val
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
```

<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 64

Cys Ala Ser Gly Cys Arg Gly
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 65

Cys Leu Ser Gly Cys Arg Gly
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Heptanoyl
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)

```
<223> OTHER INFORMATION: (D)Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 66

Cys Ala Ser Gly Cys Arg Gly
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Heptanoyl
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 67

Cys Ala Ser Gly Cys Arg Gly
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Heptanoyl
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: nMeS
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2
```

```
<400> SEQUENCE: 68

Cys Ala Ser Gly Cys Arg Gly
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Heptanoyl
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: nMeS
<220> FEATURE:
<221> NAME/KEY: MOD_RES
<222> LOCATION: (4)..(4)
<223> OTHER INFORMATION: (D)Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 69

Cys Ala Ser Gly Cys Arg Gly
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Cppg
<220> FEATURE:
<223> OTHER INFORMATION: C-term NH2

<400> SEQUENCE: 70

Cys Ala Ser Gly Cys Arg Gly
1               5
```

```
<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Chg
<220> FEATURE:
<223> OTHER INFORMATION: C-term NH2

<400> SEQUENCE: 71

Cys Ala Ser Gly Cys Arg Gly
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<223> OTHER INFORMATION: C-term NH2

<400> SEQUENCE: 72

Cys Ala Ala Ile Cys Arg Val
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: OctG
<220> FEATURE:
<221> NAME/KEY: MOD_RES
```

```
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 73

Cys Gly Ser Gly Cys Arg Gly
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (8)..(8)
<223> OTHER INFORMATION: nMeV
<220> FEATURE:
<223> OTHER INFORMATION: C-term NH2

<400> SEQUENCE: 74

Met Cys Glu Ser Ile Cys Arg Val
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 75

Cys Ala Ala Gly Cys Arg Gly
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 76

Cys Gly Ala Gly Cys Arg Gly
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (5)..(5)
<223> OTHER INFORMATION: Cpg
<220> FEATURE:
<223> OTHER INFORMATION: C-term NH2

<400> SEQUENCE: 77

Met Cys Glu Ser Gly Cys Arg Val
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 78
```

```
Cys Xaa Ala Gly Cys Arg Gly
1               5
```

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 79

```
Cys Ala Ala Gly Cys Arg Gly
1               5
```

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (6)..(6)
<223> OTHER INFORMATION: azaTrp
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 80

```
Cys Ala Ser Gly Cys Trp Gly
1               5
```

```
<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Tranexamic
<220> FEATURE:
<221> NAME/KEY: MOD_RES
<222> LOCATION: (3)..(3)
<223> OTHER INFORMATION: (D)Phg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 81

Cys Xaa Gly Cys Arg Gly
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: Chg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 82

Cys Ala Ser Gly Cys Arg Gly
1               5

<210> SEQ ID NO 83
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: ortho-xylyl linker between residues
<220> FEATURE:
<221> NAME/KEY: MOD_RES
<222> LOCATION: (2)..(2)
<223> OTHER INFORMATION: Phg
<220> FEATURE:
<221> NAME/KEY: MOD_RES
<222> LOCATION: (5)..(5)
<223> OTHER INFORMATION: Tbg
<220> FEATURE:
<223> OTHER INFORMATION: C-term NH2

<400> SEQUENCE: 83

Cys Gly Cys Arg Gly
1               5

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: para-xylyl linker between residues
<220> FEATURE:
<221> NAME/KEY: MOD_RES
<222> LOCATION: (2)..(2)
<223> OTHER INFORMATION: Phg
<220> FEATURE:
<221> NAME/KEY: MOD_RES
<222> LOCATION: (5)..(5)
<223> OTHER INFORMATION: Tbg
<220> FEATURE:
<223> OTHER INFORMATION: C-term NH2

<400> SEQUENCE: 84

Cys Gly Cys Arg Gly
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: dibromoxylene linker between residues
<220> FEATURE:
<223> OTHER INFORMATION: C-term NH2

<400> SEQUENCE: 85

Cys Glu Ser Ile Cys Arg Val
1               5
```

```
<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 86

Met Cys Glu Ser Ile Cys Arg Glu Leu Arg Tyr Ser Glu
1               5                   10

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 87

Met Cys Glu Ser Ile Cys Arg Glu
1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 88

Met Cys Glu Ser Asn Cys Arg Val
1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 89

Met Cys Glu Tyr Ile Cys Arg Val
1               5
```

```
<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Tranexamic
<220> FEATURE:
<221> NAME/KEY: MOD_RES
<222> LOCATION: (3)..(3)
<223> OTHER INFORMATION: Phg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 90

Cys Xaa Gly Cys Arg Gly
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (4)..(4)
<223> OTHER INFORMATION: Chg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 91

Cys Xaa Ala Gly Cys Arg Gly
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Acc
<220> FEATURE:
<221> NAME/KEY: MOD_RES
<222> LOCATION: (4)..(4)
<223> OTHER INFORMATION: (D)Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 92

Cys Xaa Ala Gly Cys Arg Gly
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Acc
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 93

Cys Xaa Ala Gly Cys Arg Gly
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
```

```
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: AcPyr
<220> FEATURE:
<221> NAME/KEY: MOD_RES
<222> LOCATION: (4)..(4)
<223> OTHER INFORMATION: (D)Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 94

Cys Xaa Ala Gly Cys Arg Gly
1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: AcPyr
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 95

Cys Xaa Ala Gly Cys Arg Gly
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Acbc
<220> FEATURE:
```

```
<221> NAME/KEY: MOD_RES
<222> LOCATION: (4)..(4)
<223> OTHER INFORMATION: (D)Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 96

Cys Xaa Ala Gly Cys Arg Gly
1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Acbc
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 97

Cys Xaa Ala Gly Cys Arg Gly
1               5

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (4)..(4)
<223> OTHER INFORMATION: (D)Phg
<220> FEATURE:
<221> NAME/KEY: MOD_RES
<222> LOCATION: (7)..(7)
<223> OTHER INFORMATION: Tbg
```

```
<220> FEATURE:
<223> OTHER INFORMATION: C-term NH2

<400> SEQUENCE: 98

Cys Xaa Ala Gly Cys Arg Gly Leu Arg Tyr Ser Glu
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 99

Cys Xaa Ala Gly Cys Arg Gly Leu Arg Tyr Ser Glu
1               5                   10

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: AcPyr
<220> FEATURE:
<221> NAME/KEY: MOD_RES
<222> LOCATION: (4)..(4)
<223> OTHER INFORMATION: Chg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 100

Cys Xaa Ala Gly Cys Arg Gly
1               5
```

```
<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (6)..(6)
<223> OTHER INFORMATION: nMeC
<220> FEATURE:
<223> OTHER INFORMATION: C-term NH2

<400> SEQUENCE: 101

Met Cys Glu Ser Ile Cys Arg Val
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: 3-methoxy dibromoxylene linker between residues
<220> FEATURE:
<223> OTHER INFORMATION: C-term NH2

<400> SEQUENCE: 102

Met Cys Glu Ser Ile Cys Arg Val
1               5

<210> SEQ ID NO 103
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 103

Met Cys Asn Tyr Trp Ser Pro Trp Thr Glu Cys Ser Arg
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 104

Met Cys Asn Tyr Trp Ser Pro Trp Thr Glu Cys Ser Ala
1               5                   10

<210> SEQ ID NO 105
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 105

Met Cys Asn Tyr Trp Ser Pro Trp Thr Ser Glu Ile Cys
1               5                   10

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 106

Asn Tyr Trp Ser Pro Trp Thr
1               5

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 107

Met Ser Asn Tyr Trp Ser Pro Trp Thr Glu Ser Ser Ala
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(11)
<223> OTHER INFORMATION: dibromoxylene linker between residues
<220> FEATURE:
<223> OTHER INFORMATION: C-term NH2

<400> SEQUENCE: 108

Met Cys Asn Tyr Trp Ser Pro Trp Thr Glu Cys Ser Ala
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(13)
```

<223> OTHER INFORMATION: dibromoxylene linker between residues
<220> FEATURE:
<223> OTHER INFORMATION: C-term NH2

<400> SEQUENCE: 109

Met Cys Asn Tyr Trp Ser Pro Trp Thr Ser Glu Ile Cys
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 110

Met Cys Asn Tyr Trp Ser Pro Trp Thr Glu Cys Ser
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 111

Met Cys Asn Tyr Trp Ser Pro Trp Thr Glu Cys
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 112

Met Cys Asn Tyr Trp Ser Pro Trp Thr Glu
1               5                   10

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 113

Met Cys Asn Tyr Trp Ser Pro Trp Thr
1               5

<210> SEQ ID NO 114
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<223> OTHER INFORMATION: C-term NH2

<400> SEQUENCE: 114

Met Cys Asn Tyr Trp Ser Pro Trp
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 115

Met Cys Asn Tyr Trp Ser Pro
1               5

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 116

Cys Asn Tyr Trp Ser Pro Trp Thr Glu Cys Ser Ala
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 117

Asn Tyr Trp Ser Pro Trp Thr Glu Cys Ser Ala
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 118

Tyr Trp Ser Pro Trp Thr Glu Cys Ser Ala
1               5                   10
```

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 119

Trp Ser Pro Trp Thr Glu Cys Ser Ala
1               5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 120

Ser Pro Trp Thr Glu Cys Ser Ala
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 121

Pro Trp Thr Glu Cys Ser Ala
1               5

<210> SEQ ID NO 122
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 122

Met Cys Asn Tyr Trp Ser Pro Trp Thr Ser Glu Ile
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: C-term NH2

<400> SEQUENCE: 123

Met Cys Asn Tyr Trp Ser Pro Trp Thr Ser Glu
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 124

Met Cys Asn Tyr Trp Ser Pro Trp Thr Ser
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(10)
<223> OTHER INFORMATION: dibromoxylene linker between residues
<220> FEATURE:
<223> OTHER INFORMATION: C-term NH2

<400> SEQUENCE: 125

Cys Asn Tyr Trp Ser Pro Trp Thr Glu Cys Ser Ala
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 126

Cys Asn Tyr Trp Ser Pro Trp Thr Glu Cys
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 127
```

Cys Asn Tyr Trp Ser Pro Trp Thr Glu Ala
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 128

Cys Asn Tyr Trp Ser Pro Trp Thr Ala Cys
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 129

Cys Asn Tyr Trp Ser Pro Trp Ala Glu Cys
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 130

Cys Asn Tyr Trp Ser Pro Ala Thr Glu Cys
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 131

Cys Asn Tyr Trp Ala Pro Trp Thr Glu Cys
1               5                   10

<210> SEQ ID NO 132
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 132

Cys Asn Tyr Ala Ser Pro Trp Thr Glu Cys
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 133

Cys Asn Ala Trp Ser Pro Trp Thr Glu Cys
1               5                   10

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 134

Cys Asn Tyr Trp Ser Pro Trp Thr Cys
1               5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 135

Cys Asn Tyr Trp Ser Pro Trp Thr
1               5

<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

<221> NAME/KEY: misc_feature
<222> LOCATION: (1)..(10)
<223> OTHER INFORMATION: dibromoxylene linker between residues
<220> FEATURE:
<223> OTHER INFORMATION: C-term NH2

<400> SEQUENCE: 136

Cys Asn Tyr Trp Ser Pro Trp Thr Ala Cys
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 137

Cys Asn Tyr Trp Ser Ala Trp Thr Glu Cys
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 138

Ala Asn Tyr Trp Ser Pro Trp Thr Glu Cys
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nvl
<220> FEATURE:
<223> OTHER INFORMATION: C-term NH2

<400> SEQUENCE: 139

Val Asn Tyr Trp Ser Pro Trp Thr Ala Cys
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac

```
<220> FEATURE:
<221> NAME/KEY: MOD_RES
<222> LOCATION: (10)..(10)
<223> OTHER INFORMATION: Nvl
<220> FEATURE:
<223> OTHER INFORMATION: C-term NH2

<400> SEQUENCE: 140

Cys Asn Tyr Trp Ser Pro Trp Thr Ala Val
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nvl
<220> FEATURE:
<221> NAME/KEY: MOD_RES
<222> LOCATION: (10)..(10)
<223> OTHER INFORMATION: Nvl
<220> FEATURE:
<223> OTHER INFORMATION: C-term NH2

<400> SEQUENCE: 141

Val Asn Tyr Trp Ser Pro Trp Thr Ala Val
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(10)
<223> OTHER INFORMATION: cyclic
<220> FEATURE:
<223> OTHER INFORMATION: C-term NH2

<400> SEQUENCE: 142

Cys Asn Tyr Trp Ser Pro Trp Thr Ala Cys
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 143

Ala Asn Tyr Trp Ser Pro Trp Thr Ala Cys
1               5                   10
```

```
<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 144

Cys Asn Tyr Trp Ser Pro Trp Thr Ala Ala
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 145

Ala Asn Tyr Trp Ser Pro Trp Thr Ala Ala
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 146

Cys Asn Tyr Trp Ser Pro Trp Ala Ala Cys
1               5                   10

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: AcPyr
<220> FEATURE:
<221> NAME/KEY: MOD_RES
<222> LOCATION: (4)..(4)
<223> OTHER INFORMATION: Chg
<220> FEATURE:
<221> NAME/KEY: MOD_RES
```

```
<222> LOCATION: (6)..(6)
<223> OTHER INFORMATION: AzaTrp
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 147

Cys Xaa Ala Gly Cys Trp Gly
1               5

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term heptanoyl
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: nMeS
<220> FEATURE:
<221> NAME/KEY: MOD_RES
<222> LOCATION: (4)..(4)
<223> OTHER INFORMATION: Chg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 148

Cys Ala Ser Gly Cys Arg Gly
1               5

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Cyclo-L
<220> FEATURE:
<221> NAME/KEY: MOD_RES
<222> LOCATION: (4)..(4)
<223> OTHER INFORMATION: (D)Phg
<220> FEATURE:
<221> NAME/KEY: MOD_RES
<222> LOCATION: (7)..(7)
```

<223> OTHER INFORMATION: Tbg
<220> FEATURE:
<223> OTHER INFORMATION: C-term NH2

<400> SEQUENCE: 149

Cys Xaa Ala Gly Cys Arg Gly
1               5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Cyclo-L
<220> FEATURE:
<221> NAME/KEY: MOD_RES
<222> LOCATION: (4)..(4)
<223> OTHER INFORMATION: Phg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 150

Cys Xaa Ala Gly Cys Arg Gly
1               5

<210> SEQ ID NO 151
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (2)..(2)
<223> OTHER INFORMATION: AEA
<220> FEATURE:
<221> NAME/KEY: MOD_RES
<222> LOCATION: (3)..(3)
<223> OTHER INFORMATION: Phg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 151

Cys Xaa Gly Cys Arg Gly

```
1               5

<210> SEQ ID NO 152
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (4)..(4)
<223> OTHER INFORMATION: Chg
<220> FEATURE:
<223> OTHER INFORMATION: C-term 3,3-dimethylbutan-2-amine

<400> SEQUENCE: 152

Cys Xaa Ala Gly Cys Arg
1               5

<210> SEQ ID NO 153
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (4)..(4)
<223> OTHER INFORMATION: Chg
<220> FEATURE:
<223> OTHER INFORMATION: C-term OH

<400> SEQUENCE: 153

Cys Xaa Ala Gly Cys Arg
1               5

<210> SEQ ID NO 154
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-SAc
<220> FEATURE:
```

```
<221> NAME/KEY: misc_feature
<222> LOCATION: (1)..(4)
<223> OTHER INFORMATION: dibromoxylene linker between residues
<220> FEATURE:
<223> OTHER INFORMATION: C-term NH2

<400> SEQUENCE: 154

Xaa Ser Ile Cys Arg Val
1               5

<210> SEQ ID NO 155
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<223> OTHER INFORMATION: C-term NH2

<400> SEQUENCE: 155

Cys Ser Ile Cys Arg Val
1               5

<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: para-xylyl linker between residues
<220> FEATURE:
<223> OTHER INFORMATION: C-term NH2

<400> SEQUENCE: 156

Cys Ser Ile Cys Arg Val
1               5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: 1,3,5-dibromoxylene linker between residues
<220> FEATURE:
<221> NAME/KEY: MOD_RES
<222> LOCATION: (2)..(2)
<223> OTHER INFORMATION: Aib
```

```
<220> FEATURE:
<221> NAME/KEY: MOD_RES
<222> LOCATION: (4)..(4)
<223> OTHER INFORMATION: Chg
<220> FEATURE:
<221> NAME/KEY: misc_feature
<222> LOCATION: (5)..(9)
<223> OTHER INFORMATION: 1,3,5-dibromoxylene linker between residues
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 157

Cys Xaa Ala Gly Cys Arg Gly Pro Cys
1               5

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: 1,3,5-dibromoxylene linker between residues
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (4)..(4)
<223> OTHER INFORMATION: Chg
<220> FEATURE:
<221> NAME/KEY: misc_feature
<222> LOCATION: (5)..(11)
<223> OTHER INFORMATION: 1,3,5-dibromoxylene linker between residues
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 158

Cys Xaa Ala Gly Cys Arg Gly Leu Arg Tyr Cys
1               5                   10

<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Chg
<220> FEATURE:
<221> NAME/KEY: misc_feature
<222> LOCATION: (2)..(6)
<223> OTHER INFORMATION: dibromoxylene linker between residues
<220> FEATURE:
```

```
<223> OTHER INFORMATION: C-term NH2

<400> SEQUENCE: 159

Gly Cys Arg Val Ala Cys
1               5

<210> SEQ ID NO 160
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Chg
<220> FEATURE:
<221> NAME/KEY: misc_feature
<222> LOCATION: (2)..(6)
<223> OTHER INFORMATION: dibromoxylene linker between residues
<220> FEATURE:
<223> OTHER INFORMATION: C-term NH2

<400> SEQUENCE: 160

Gly Cys Arg Val Pro Cys
1               5

<210> SEQ ID NO 161
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: ortho-xylyl linker between residues
<220> FEATURE:
<223> OTHER INFORMATION: C-term NH2

<400> SEQUENCE: 161

Cys Ser Ile Cys Arg Val
1               5

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
```

```
<222> LOCATION: (4)..(4)
<223> OTHER INFORMATION: Chg
<220> FEATURE:
<223> OTHER INFORMATION: C-term 2-amino-3,3-dimethylbutan-1-ol

<400> SEQUENCE: 162

Cys Xaa Ala Gly Cys Arg
1               5

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: dibromoxylene linker between residues
<220> FEATURE:
<221> NAME/KEY: MOD_RES
<222> LOCATION: (7)..(7)
<223> OTHER INFORMATION: nMeR
<220> FEATURE:
<223> OTHER INFORMATION: C-term NH2

<400> SEQUENCE: 163

Met Cys Glu Ser Ile Cys Arg Val
1               5

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Chg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 164

Cys Ser Gly Cys Arg Gly
1               5

<210> SEQ ID NO 165
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
```

```
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (2)..(2)
<223> OTHER INFORMATION: nMeS
<220> FEATURE:
<221> NAME/KEY: MOD_RES
<222> LOCATION: (3)..(3)
<223> OTHER INFORMATION: Chg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 165

Cys Ser Gly Cys Arg Gly
1               5

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: AcPyr
<220> FEATURE:
<221> NAME/KEY: MOD_RES
<222> LOCATION: (4)..(4)
<223> OTHER INFORMATION: Chg
<220> FEATURE:
<221> NAME/KEY: MOD_RES
<222> LOCATION: (6)..(6)
<223> OTHER INFORMATION: 4-BZA
<220> FEATURE:
<223> OTHER INFORMATION: C-term NH2

<400> SEQUENCE: 166

Cys Xaa Ala Gly Cys Xaa Val
1               5

<210> SEQ ID NO 167
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Chg
```

-continued

```
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 167

Cys Pro Gly Cys Arg Gly
1               5

<210> SEQ ID NO 168
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (2)..(2)
<223> OTHER INFORMATION: Cyclo-L
<220> FEATURE:
<221> NAME/KEY: MOD_RES
<222> LOCATION: (3)..(3)
<223> OTHER INFORMATION: Chg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 168

Cys Xaa Gly Cys Arg Gly
1               5

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Cyclo-L
<220> FEATURE:
<221> NAME/KEY: MOD_RES
<222> LOCATION: (4)..(4)
<223> OTHER INFORMATION: Chg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2
```

-continued

```
<400> SEQUENCE: 169

Cys Xaa Ala Gly Cys Arg Gly
1               5

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Cyclo-L
<220> FEATURE:
<221> NAME/KEY: MOD_RES
<222> LOCATION: (4)..(4)
<223> OTHER INFORMATION: Chg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 170

Cys Xaa Ala Gly Cys Arg Gly Leu Arg Tyr
1               5                   10

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (6)..(6)
<223> OTHER INFORMATION: D-Arg
<220> FEATURE:
<223> OTHER INFORMATION: C-term NH2

<400> SEQUENCE: 171

Cys Glu Ser Ile Cys Arg Val
1               5

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (6)..(6)
<223> OTHER INFORMATION: Orn
<220> FEATURE:
<223> OTHER INFORMATION: C-term NH2

<400> SEQUENCE: 172

Cys Glu Ser Ile Cys Xaa Val
1               5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: cyclic
<220> FEATURE:
<221> NAME/KEY: MOD_RES
<222> LOCATION: (4)..(4)
<223> OTHER INFORMATION: Aib
<220> FEATURE:
<221> NAME/KEY: MOD_RES
<222> LOCATION: (6)..(6)
<223> OTHER INFORMATION: Chg
<220> FEATURE:
<221> NAME/KEY: MOD_RES
<222> LOCATION: (9)..(9)
<223> OTHER INFORMATION: Tbg
<220> FEATURE:
<223> OTHER INFORMATION: C-term NH2

<400> SEQUENCE: 173

Ala Cys Pro Xaa Ala Gly Asp Arg Gly
1               5

<210> SEQ ID NO 174
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (2)..(2)
<223> OTHER INFORMATION: Cyclo-L
<220> FEATURE:
<221> NAME/KEY: MOD_RES
<222> LOCATION: (3)..(3)
<223> OTHER INFORMATION: Chg
<220> FEATURE:
<221> NAME/KEY: MOD_RES
<222> LOCATION: (6)..(6)
<223> OTHER INFORMATION: Tbg
<220> FEATURE:
```

```
<223> OTHER INFORMATION: C-term NH2

<400> SEQUENCE: 174

Cys Xaa Gly Cys Lys Gly
1               5

<210> SEQ ID NO 175
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Cyclo-L
<220> FEATURE:
<221> NAME/KEY: MOD_RES
<222> LOCATION: (4)..(4)
<223> OTHER INFORMATION: Chg
<220> FEATURE:
<223> OTHER INFORMATION: C-term OH

<400> SEQUENCE: 175

Cys Xaa Ala Gly Cys Arg Val
1               5

<210> SEQ ID NO 176
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (3)..(3)
<223> OTHER INFORMATION: Chg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 176

Cys Xaa Gly Cys Arg Gly
1               5

<210> SEQ ID NO 177
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (2)..(2)
<223> OTHER INFORMATION: Acc
<220> FEATURE:
<221> NAME/KEY: MOD_RES
<222> LOCATION: (3)..(3)
<223> OTHER INFORMATION: Chg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 177

Cys Xaa Gly Cys Arg Gly
1               5

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Cyclo-L
<220> FEATURE:
<221> NAME/KEY: MOD_RES
<222> LOCATION: (4)..(4)
<223> OTHER INFORMATION: Chg
<220> FEATURE:
<223> OTHER INFORMATION: C-term NHCH3

<400> SEQUENCE: 178

Cys Xaa Ala Gly Cys Arg Val
1               5

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
```

```
<223> OTHER INFORMATION: dibromoxylene linker between residues
<220> FEATURE:
<221> NAME/KEY: MOD_RES
<222> LOCATION: (2)..(2)
<223> OTHER INFORMATION: AcPyr
<220> FEATURE:
<221> NAME/KEY: MOD_RES
<222> LOCATION: (4)..(4)
<223> OTHER INFORMATION: Chg
<220> FEATURE:
<221> NAME/KEY: MOD_RES
<222> LOCATION: (6)..(6)
<223> OTHER INFORMATION: 3-BZA
<220> FEATURE:
<223> OTHER INFORMATION: C-term NH2

<400> SEQUENCE: 179

Cys Xaa Ala Gly Cys Xaa Val
1               5

<210> SEQ ID NO 180
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (2)..(2)
<223> OTHER INFORMATION: (a-Me)P
<220> FEATURE:
<221> NAME/KEY: MOD_RES
<222> LOCATION: (3)..(3)
<223> OTHER INFORMATION: Chg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 180

Cys Pro Gly Cys Arg Gly
1               5

<210> SEQ ID NO 181
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (2)..(2)
<223> OTHER INFORMATION: Acbc
<220> FEATURE:
<221> NAME/KEY: MOD_RES
```

```
<222> LOCATION: (3)..(3)
<223> OTHER INFORMATION: Chg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 181

Cys Xaa Gly Cys Arg Gly
1               5

<210> SEQ ID NO 182
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (2)..(2)
<223> OTHER INFORMATION: AcPyr
<220> FEATURE:
<221> NAME/KEY: MOD_RES
<222> LOCATION: (3)..(3)
<223> OTHER INFORMATION: Chg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 182

Cys Xaa Gly Cys Arg Gly
1               5

<210> SEQ ID NO 183
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Chg
<220> FEATURE:
<223> OTHER INFORMATION: C-term OH

<400> SEQUENCE: 183

Cys Pro Gly Cys Arg Val
1               5
```

-continued

```
<210> SEQ ID NO 184
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Chg
<220> FEATURE:
<223> OTHER INFORMATION: C-term NHCH3

<400> SEQUENCE: 184

Cys Pro Gly Cys Arg Val
1               5

<210> SEQ ID NO 185
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: AcPyr
<220> FEATURE:
<221> NAME/KEY: MOD_RES
<222> LOCATION: (4)..(4)
<223> OTHER INFORMATION: Chg
<220> FEATURE:
<221> NAME/KEY: MOD_RES
<222> LOCATION: (6)..(6)
<223> OTHER INFORMATION: 4-BZA-N-hexylcarbamate
<220> FEATURE:
<223> OTHER INFORMATION: C-term NH2

<400> SEQUENCE: 185

Cys Xaa Ala Gly Cys Xaa Val
1               5

<210> SEQ ID NO 186
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
```

```
<220> FEATURE:
<221> NAME/KEY: MOD_RES
<222> LOCATION: (3)..(3)
<223> OTHER INFORMATION: Chg
<220> FEATURE:
<221> NAME/KEY: MOD_RES
<222> LOCATION: (5)..(5)
<223> OTHER INFORMATION: R(N-omega hexylcarbamate)
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 186

Cys Pro Gly Cys Arg Gly
1               5

<210> SEQ ID NO 187
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: (D)Phg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 187

Cys Pro Gly Cys Arg Gly
1               5

<210> SEQ ID NO 188
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Phg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2
```

```
<400> SEQUENCE: 188

Cys Pro Gly Cys Arg Gly
1               5

<210> SEQ ID NO 189
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: (2-OMe)Phg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 189

Cys Pro Gly Cys Arg Gly
1               5

<210> SEQ ID NO 190
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (4)..(4)
<223> OTHER INFORMATION: Chg
<220> FEATURE:
<221> NAME/KEY: MOD_RES
<222> LOCATION: (7)..(7)
<223> OTHER INFORMATION: Tbg
<220> FEATURE:
<223> OTHER INFORMATION: C-term NH2

<400> SEQUENCE: 190

Cys Xaa Ala Gly Cys Arg Gly Leu Arg Tyr Ser Glu
1               5                   10

<210> SEQ ID NO 191
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(5)
<223> OTHER INFORMATION: dibromoxylene linker between residues
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (4)..(4)
<223> OTHER INFORMATION: Chg
<220> FEATURE:
<221> NAME/KEY: MOD_RES
<222> LOCATION: (7)..(7)
<223> OTHER INFORMATION: Tbg
<220> FEATURE:
<221> NAME/KEY: MOD_RES
<222> LOCATION: (12)..(12)
<223> OTHER INFORMATION: E(PEG40K)
<220> FEATURE:
<223> OTHER INFORMATION: C-term NH2

<400> SEQUENCE: 191

Cys Xaa Ala Gly Cys Arg Gly Leu Arg Tyr Ser Glu
1               5                   10

<210> SEQ ID NO 192
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: (alpha-Me)Phg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 192

Cys Pro Gly Cys Arg Gly
1               5

<210> SEQ ID NO 193
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term BODIPY-TMR
<220> FEATURE:
<221> NAME/KEY: misc_feature
<222> LOCATION: (2)..(6)
```

```
<223> OTHER INFORMATION: dibromoxylene linker between residues
<220> FEATURE:
<223> OTHER INFORMATION: C-term NH2

<400> SEQUENCE: 193

Met Cys Glu Ser Ile Cys Arg Val
1               5

<210> SEQ ID NO 194
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (2)..(2)
<223> OTHER INFORMATION: Aze
<220> FEATURE:
<221> NAME/KEY: MOD_RES
<222> LOCATION: (3)..(3)
<223> OTHER INFORMATION: Chg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 194

Cys Xaa Gly Cys Arg Gly
1               5

<210> SEQ ID NO 195
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Chg
<220> FEATURE:
<223> OTHER INFORMATION: C-term OH

<400> SEQUENCE: 195

Cys Pro Gly Cys Arg
1               5

<210> SEQ ID NO 196
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Chg
<220> FEATURE:
<223> OTHER INFORMATION: C-term (S)-2,2-dimethyl-1-(pyridin-2-yl)propan-
      1-amine

<400> SEQUENCE: 196

Cys Pro Gly Cys Arg
1               5

<210> SEQ ID NO 197
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Chg
<220> FEATURE:
<223> OTHER INFORMATION: C-term 2-methyl-1-(4H-1,2,4-triazol-3-yl)
      propan-1-amine

<400> SEQUENCE: 197

Cys Pro Gly Cys Arg
1               5

<210> SEQ ID NO 198
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Chg
<220> FEATURE:
<221> NAME/KEY: MOD_RES
<222> LOCATION: (5)..(5)
<223> OTHER INFORMATION: 2-APY
<220> FEATURE:
<221> NAME/KEY: MOD_RES
<222> LOCATION: (6)..(6)
```

```
<223> OTHER INFORMATION: Tbg
<220> FEATURE:
<223> OTHER INFORMATION: C-term NH2

<400> SEQUENCE: 198

Cys Pro Gly Cys Xaa Gly
1               5

<210> SEQ ID NO 199
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (2)..(2)
<223> OTHER INFORMATION: (alpha-Me)Pro
<220> FEATURE:
<221> NAME/KEY: MOD_RES
<222> LOCATION: (3)..(3)
<223> OTHER INFORMATION: Phg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 199

Cys Pro Gly Cys Arg Gly
1               5

<210> SEQ ID NO 200
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (2)..(2)
<223> OTHER INFORMATION: (alpha-Me)Pro
<220> FEATURE:
<221> NAME/KEY: MOD_RES
<222> LOCATION: (3)..(3)
<223> OTHER INFORMATION: (D)Phg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 200

Cys Pro Gly Cys Arg Gly
```

1               5

<210> SEQ ID NO 201
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Chg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 201

Cys Glu Gly Cys Arg Gly
1               5

<210> SEQ ID NO 202
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Phg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term OH

<400> SEQUENCE: 202

Cys Pro Gly Cys Arg Gly Leu
1               5

<210> SEQ ID NO 203
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:

```
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Chg
<220> FEATURE:
<221> NAME/KEY: MOD_RES
<222> LOCATION: (5)..(5)
<223> OTHER INFORMATION: 2-amino-4-(6-aminopyridin-3-yl)butanoic acid
<220> FEATURE:
<223> OTHER INFORMATION: C-term NH2

<400> SEQUENCE: 203

Cys Pro Gly Cys Xaa Val
1               5

<210> SEQ ID NO 204
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: (nMe)Ile
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 204

Cys Ser Ile Cys Arg Gly
1               5

<210> SEQ ID NO 205
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Phg
<220> FEATURE:
<221> NAME/KEY: MOD_RES
<222> LOCATION: (5)..(5)
<223> OTHER INFORMATION: 4-Cl-Phe
<220> FEATURE:
<221> NAME/KEY: MOD_RES
<222> LOCATION: (6)..(6)
<223> OTHER INFORMATION: Tbg
```

```
<220> FEATURE:
<223> OTHER INFORMATION: C-term NH2

<400> SEQUENCE: 205

Cys Pro Gly Cys Phe Gly
1               5

<210> SEQ ID NO 206
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: (D)Phg
<220> FEATURE:
<221> NAME/KEY: MOD_RES
<222> LOCATION: (5)..(5)
<223> OTHER INFORMATION: 4-Cl-Phe
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 206

Cys Pro Gly Cys Phe Gly
1               5

<210> SEQ ID NO 207
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Phg
<220> FEATURE:
<221> NAME/KEY: MOD_RES
<222> LOCATION: (5)..(5)
<223> OTHER INFORMATION: 3-Cl-Phe
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 207

Cys Pro Gly Cys Phe Gly
1               5
```

```
<210> SEQ ID NO 208
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: (D)Phg
<220> FEATURE:
<221> NAME/KEY: MOD_RES
<222> LOCATION: (5)..(5)
<223> OTHER INFORMATION: 3-Cl-Phe
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 208

Cys Pro Gly Cys Phe Gly
1               5

<210> SEQ ID NO 209
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Phg
<220> FEATURE:
<221> NAME/KEY: MOD_RES
<222> LOCATION: (5)..(5)
<223> OTHER INFORMATION: 5-Cl-Trp
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 209

Cys Pro Gly Cys Trp Gly
1               5

<210> SEQ ID NO 210
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: (D)Phg
<220> FEATURE:
<221> NAME/KEY: MOD_RES
<222> LOCATION: (5)..(5)
<223> OTHER INFORMATION: 5-Cl-Trp
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 210

Cys Pro Gly Cys Trp Gly
1               5

<210> SEQ ID NO 211
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Phg
<220> FEATURE:
<221> NAME/KEY: MOD_RES
<222> LOCATION: (5)..(5)
<223> OTHER INFORMATION: Dab
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 211

Cys Pro Gly Cys Xaa Gly
1               5

<210> SEQ ID NO 212
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
```

```
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: (D)Phg
<220> FEATURE:
<221> NAME/KEY: MOD_RES
<222> LOCATION: (5)..(5)
<223> OTHER INFORMATION: Dab
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 212

Cys Pro Gly Cys Xaa Gly
1               5

<210> SEQ ID NO 213
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (2)..(2)
<223> OTHER INFORMATION: E(PEG40K)
<220> FEATURE:
<221> NAME/KEY: MOD_RES
<222> LOCATION: (3)..(3)
<223> OTHER INFORMATION: Chg
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 213

Cys Glu Gly Cys Arg Gly
1               5

<210> SEQ ID NO 214
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Chg
```

```
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term OH

<400> SEQUENCE: 214

Cys Pro Gly Cys Arg Gly
1               5

<210> SEQ ID NO 215
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Phg
<220> FEATURE:
<221> NAME/KEY: MOD_RES
<222> LOCATION: (5)..(5)
<223> OTHER INFORMATION: (4-amidino)Phe
<220> FEATURE:
<223> OTHER INFORMATION: C-term NH2

<400> SEQUENCE: 215

Cys Pro Gly Cys Phe Val
1               5

<210> SEQ ID NO 216
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Phg
<220> FEATURE:
<221> NAME/KEY: MOD_RES
<222> LOCATION: (6)..(6)
<223> OTHER INFORMATION: Tbg
<220> FEATURE:
<221> NAME/KEY: MOD_RES
<222> LOCATION: (8)..(8)
<223> OTHER INFORMATION: nMeR
<220> FEATURE:
<223> OTHER INFORMATION: C-term NH2

<400> SEQUENCE: 216

Cys Pro Gly Cys Arg Gly Leu Arg Tyr Ser Glu
1               5                   10
```

```
<210> SEQ ID NO 217
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: (D)Phg
<220> FEATURE:
<221> NAME/KEY: MOD_RES
<222> LOCATION: (6)..(6)
<223> OTHER INFORMATION: Tbg
<220> FEATURE:
<221> NAME/KEY: MOD_RES
<222> LOCATION: (8)..(8)
<223> OTHER INFORMATION: nMeR
<220> FEATURE:
<223> OTHER INFORMATION: C-term NH2

<400> SEQUENCE: 217

Cys Pro Gly Cys Arg Gly Leu Arg Tyr Ser Glu
1               5                   10

<210> SEQ ID NO 218
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Ind
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 218

Cys Pro Xaa Cys Arg Gly
1               5

<210> SEQ ID NO 219
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: Phg
<220> FEATURE:
<221> NAME/KEY: MOD_RES
<222> LOCATION: (5)..(5)
<223> OTHER INFORMATION: ABP
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 219

Cys Pro Gly Cys Xaa Gly
1               5

<210> SEQ ID NO 220
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
<221> NAME/KEY: MOD_RES
<222> LOCATION: (3)..(3)
<223> OTHER INFORMATION: (D)Phg
<220> FEATURE:
<221> NAME/KEY: MOD_RES
<222> LOCATION: (5)..(5)
<223> OTHER INFORMATION: ABP
<220> FEATURE:
<221> NAME/KEY: MOD_RES
<222> LOCATION: (6)..(6)
<223> OTHER INFORMATION: Tbg
<220> FEATURE:
<223> OTHER INFORMATION: C-term NH2

<400> SEQUENCE: 220

Cys Pro Gly Cys Xaa Gly
1               5

<210> SEQ ID NO 221
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (des NH2)Cys
<220> FEATURE:
<221> NAME/KEY: misc_feature
<222> LOCATION: (1)..(4)
<223> OTHER INFORMATION: dibromoxylene linker between residues
<220> FEATURE:
```

```
<221> NAME/KEY: MOD_RES
<222> LOCATION: (3)..(3)
<223> OTHER INFORMATION: Phg
<220> FEATURE:
<223> OTHER INFORMATION: C-term 4-(aminomethyl)benzimidamide

<400> SEQUENCE: 221

Cys Pro Gly Cys
1

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(10)
<223> OTHER INFORMATION: cyclic

<400> SEQUENCE: 222

Cys Asn Tyr Trp Ser Pro Trp Thr Ala Ala
1               5                   10

<210> SEQ ID NO 223
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(10)
<223> OTHER INFORMATION: dibromoxylene linker between residues
<220> FEATURE:
<221> NAME/KEY: MOD_RES
<222> LOCATION: (3)..(3)
<223> OTHER INFORMATION: nMeY
<220> FEATURE:
<221> NAME/KEY: MOD_RES
<222> LOCATION: (5)..(5)
<223> OTHER INFORMATION: nMeS
<220> FEATURE:
<221> NAME/KEY: MOD_RES
<222> LOCATION: (8)..(8)
<223> OTHER INFORMATION: nMeT
<220> FEATURE:
<223> OTHER INFORMATION: C-term NH2

<400> SEQUENCE: 223

Cys Asn Tyr Trp Ser Pro Trp Thr Ala Cys
1               5                   10

<210> SEQ ID NO 224
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (1)..(10)
<223> OTHER INFORMATION: cyclic
<220> FEATURE:
<221> NAME/KEY: MOD_RES
```

```
<222> LOCATION: (3)..(3)
<223> OTHER INFORMATION: nMeY
<220> FEATURE:
<221> NAME/KEY: MOD_RES
<222> LOCATION: (5)..(5)
<223> OTHER INFORMATION: nMeS
<220> FEATURE:
<221> NAME/KEY: MOD_RES
<222> LOCATION: (8)..(8)
<223> OTHER INFORMATION: nMeT
<220> FEATURE:
<223> OTHER INFORMATION: C-term NH2

<400> SEQUENCE: 224

Cys Asn Tyr Trp Ser Pro Trp Thr Ala Cys
1               5                   10

<210> SEQ ID NO 225
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (10)..(10)
<223> OTHER INFORMATION: D-Cys
<220> FEATURE:
<223> OTHER INFORMATION: C-term NH2

<400> SEQUENCE: 225

Cys Asn Tyr Trp Ser Pro Trp Thr Ala Cys
1               5                   10

<210> SEQ ID NO 226
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: D-Ala
<220> FEATURE:
<223> OTHER INFORMATION: C-term NH2

<400> SEQUENCE: 226

Cys Asn Tyr Trp Ser Pro Trp Thr Ala Cys
1               5                   10

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: D-Thr
<220> FEATURE:
<223> OTHER INFORMATION: C-term NH2
```

```
<400> SEQUENCE: 227

Cys Asn Tyr Trp Ser Pro Trp Thr Ala Cys
1               5                   10

<210> SEQ ID NO 228
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: D-Trp
<220> FEATURE:
<223> OTHER INFORMATION: C-term NH2

<400> SEQUENCE: 228

Cys Asn Tyr Trp Ser Pro Trp Thr Ala Cys
1               5                   10

<210> SEQ ID NO 229
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (6)..(6)
<223> OTHER INFORMATION: D-Pro
<220> FEATURE:
<223> OTHER INFORMATION: C-term NH2

<400> SEQUENCE: 229

Cys Asn Tyr Trp Ser Pro Trp Thr Ala Cys
1               5                   10

<210> SEQ ID NO 230
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: D-Ser
<220> FEATURE:
<223> OTHER INFORMATION: C-term NH2

<400> SEQUENCE: 230

Cys Asn Tyr Trp Ser Pro Trp Thr Ala Cys
1               5                   10

<210> SEQ ID NO 231
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: D-Trp
<220> FEATURE:
<223> OTHER INFORMATION: C-term NH2

<400> SEQUENCE: 231

Cys Asn Tyr Trp Ser Pro Trp Thr Ala Cys
1               5                   10

<210> SEQ ID NO 232
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D-Tyr
<220> FEATURE:
<223> OTHER INFORMATION: C-term NH2

<400> SEQUENCE: 232

Cys Asn Tyr Trp Ser Pro Trp Thr Ala Cys
1               5                   10

<210> SEQ ID NO 233
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: D-Asn
<220> FEATURE:
<223> OTHER INFORMATION: C-term NH2

<400> SEQUENCE: 233

Cys Asn Tyr Trp Ser Pro Trp Thr Ala Cys
1               5                   10

<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: nMeA
<220> FEATURE:
<223> OTHER INFORMATION: C-term NH2

<400> SEQUENCE: 234

Cys Asn Tyr Trp Ser Pro Trp Thr Ala Cys
1               5                   10
```

```
<210> SEQ ID NO 235
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: nMeT
<220> FEATURE:
<223> OTHER INFORMATION: C-term NH2

<400> SEQUENCE: 235

Cys Asn Tyr Trp Ser Pro Trp Thr Ala Cys
1               5                   10

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: nMeW
<220> FEATURE:
<223> OTHER INFORMATION: C-term NH2

<400> SEQUENCE: 236

Cys Asn Tyr Trp Ser Pro Trp Thr Ala Cys
1               5                   10

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: nMeS
<220> FEATURE:
<223> OTHER INFORMATION: C-term NH2

<400> SEQUENCE: 237

Cys Asn Tyr Trp Ser Pro Trp Thr Ala Cys
1               5                   10

<210> SEQ ID NO 238
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
```

```
<222> LOCATION: (4)..(4)
<223> OTHER INFORMATION: nMeW
<220> FEATURE:
<223> OTHER INFORMATION: C-term NH2

<400> SEQUENCE: 238

Cys Asn Tyr Trp Ser Pro Trp Thr Ala Cys
1               5                   10

<210> SEQ ID NO 239
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: nMeY
<220> FEATURE:
<223> OTHER INFORMATION: C-term NH2

<400> SEQUENCE: 239

Cys Asn Tyr Trp Ser Pro Trp Thr Ala Cys
1               5                   10

<210> SEQ ID NO 240
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(3)
<223> OTHER INFORMATION: Residues joined by a bridging moiety
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (8)..(8)
<223> OTHER INFORMATION: Any amino acid or absent
<220> FEATURE:
<223> OTHER INFORMATION: see specification as filed for detailed
      description of substitutions and preferred embodiments

<400> SEQUENCE: 240

Cys Xaa Xaa Xaa Cys Arg Val Xaa
1               5

<210> SEQ ID NO 241
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 241

His His His His His His
1               5

<210> SEQ ID NO 242
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term may be H, acyl groups containing a
      linear or branched, saturated or unsaturated hydrocarbon chain
      from 1 to 20 carbon atoms, amides, carbamates, ureas, PEG or
      hydroxyalkyl starch
<220> FEATURE:
<221> NAME/KEY: MOD_RES
<222> LOCATION: (1)..(1)
<223> OTHER INFORMATION: Met, norvaline, Ala, Gly, Ser, Val, tert-
      butylglycine, Leu, phenylglycine, Ile, Pro, Trp, 7-azatryptophan,
      Phe, 4-fluoro-phenylalanine, Thr, Tyr, Val, Lys, N-methyl-
      methionine, N- methyl-valine, N-methyl-alanine, sarcosine, N-
      methyl-tert-
<220> FEATURE:
<221> NAME/KEY: MOD_RES
<222> LOCATION: (1)..(1)
<223> OTHER INFORMATION: cont'd from above; butylglycine, N-methyl-
      leucine, N-methyl-phenylglycine, N-methyl-isoleucine, N-methyl-
      tryptophan, N-methyl-7-azatryptophan, N-methyl-phenylalanine, N-
      methyl-4-fluorophenylalanine, N-methyl-threonine, N-methyl-
      tyrosine,
<220> FEATURE:
<221> NAME/KEY: MOD_RES
<222> LOCATION: (1)..(1)
<223> OTHER INFORMATION: cont'd from above; N-methyl-valine, N-methyl-
      lysine or absent
<220> FEATURE:
<221> NAME/KEY: MOD_RES
<222> LOCATION: (2)..(2)
<223> OTHER INFORMATION: Cys, penicillamine, des-amino-Cys, D-Cys,
      homocysteine or Tyr
<220> FEATURE:
<221> NAME/KEY: MOD_RES
<222> LOCATION: (3)..(3)
<223> OTHER INFORMATION: Ala, D-Ala, N-methyl-alanine, Glu, N-methyl-
      glutamate, D-Glu, Gly, sarcosine, norleucine, Lys, D-Lys, Asn,
      D-Asn, D-Glu, Arg, D-Arg, Phe, D-Phe, N-methyl-phenylalanine, Gln,
      D-Gln, Asp, D-Asp, Ser, D-Ser, N-methyl-serine, Thr, D-Thr,
      N-methyl-
<220> FEATURE:
<221> NAME/KEY: MOD_RES
<222> LOCATION: (3)..(3)
<223> OTHER INFORMATION: cont'd from above; threonine, Pro, D-Pro, Leu,
      D-Leu, N-methyl-leucine, Ile, D-Ile, N-methyl-isoleucine, Val,
      D-Val, N-methyl-valine, tert-butylglycine, D-tert-butylglycine,
      N-methyl-tert-butylglycine, Trp, D-Trp, N-methyl-tryptophan, Tyr,
      D-Tyr,
<220> FEATURE:
<221> NAME/KEY: MOD_RES
<222> LOCATION: (3)..(3)
<223> OTHER INFORMATION: cont'd from above; N-methyl-tyrosine, 1-
      aminocyclopropane-carboxylic acid, 1-aminocyclobutanecarboxylic
      acid, 1-amino-cyclopentanecarboxylic acid, 1-
      aminocyclohexanecarboxylic acid, 4-aminotetrahydro-2H-pyran-4-
      carboxylic acid, aminoisobutyric
<220> FEATURE:
<221> NAME/KEY: MOD_RES
<222> LOCATION: (3)..(3)
<223> OTHER INFORMATION: cont'd from above; acid, (S)-2-amino-3-(1H-
      tetrazol-5-yl) propanoic acid, Glu, Gly, N-methyl-glutamate, 2-
      amino pentanoic acid, 2-amino hexanoic acid, 2-amino heptanoic
      acid, 2-amino octanoic acid, 2-amino nonanoic acid, 2-amino
      decanoic acid,
<220> FEATURE:
<221> NAME/KEY: MOD_RES
<222> LOCATION: (3)..(3)
<223> OTHER INFORMATION: cont'd from above; 2-amino undecanoic acid, 2-
      amino dodecanoic acid, octylglycine, tranexamic acid, aminovaleric
      acid, 2-(2-aminoethoxy)acetic acid or absent
<220> FEATURE:
<221> NAME/KEY: MOD_RES
<222> LOCATION: (4)..(4)
<223> OTHER INFORMATION: Ala, N-methyl-alanine, Gly, sarcosine, Ser, N-
      methyl-serine, Pro, Thr, N-methyl-threonine, Val, N-methyl-valine,
      Ile, N-methyl-isoleucine, Phe, N-methyl-phenylalanine, 4-
```

```
      fluorophenyl-alanine, N-methyl-4-fluorophenylalanine, N-methyl-
      norleucine,
<220> FEATURE:
<221> NAME/KEY: MOD_RES
<222> LOCATION: (4)..(4)
<223> OTHER INFORMATION: cont'd from above; pipecolic acid, 2-carboxy
      azetidine or absent
<220> FEATURE:
<221> NAME/KEY: MOD_RES
<222> LOCATION: (5)..(5)
<223> OTHER INFORMATION: Ala, Phe, Ile, N-methyl-isoleucine, Asn, Val,
      cyclopentyl-glycine, cyclohexylglycine, cyclopropylglycine,
      phenylglycine, D-phenylglycine, tert-butylglycine,
      hexafluoroleucine, 3-Fluorovaline, 2-amino-4,4-difluoro-3-
      methylbutanoic acid,
<220> FEATURE:
<221> NAME/KEY: MOD_RES
<222> LOCATION: (5)..(5)
<223> OTHER INFORMATION: cont'd from above; 3-fluoro-isoleucine, 4-
      fluoroisoleucine, 5-fluoroisoleucine, 4-methyl-phenylglycine, 4-
      ethyl-phenyl-glycine or 4-isopropyl-phenylglycine
<220> FEATURE:
<221> NAME/KEY: MOD_RES
<222> LOCATION: (6)..(6)
<223> OTHER INFORMATION: Cys, D-Cys, homocysteine or penicillamine
<220> FEATURE:
<221> NAME/KEY: MOD_RES
<222> LOCATION: (7)..(7)
<223> OTHER INFORMATION: Arg, eta-omega methylated Arg, Lys, homolysine,
      (S)-2-amino-5-(3-methylguanidino) pentanoic acid, (S)-2-amino-3-
      (4-(amino-methyl)phenyl)propanoic acid, (S)-2-amino-3-(3-
      (aminomethyl)phenyl)propanoic acid, 7-azatryptophan, (S)-2-amino-
      4-(2-
<220> FEATURE:
<221> NAME/KEY: MOD_RES
<222> LOCATION: (7)..(7)
<223> OTHER INFORMATION: cont'd from above; aminobenzo[d]oxazol-5-
      yl)butanoic acid, a compound of formula I or a compound of formula
      II
<220> FEATURE:
<221> NAME/KEY: MOD_RES
<222> LOCATION: (8)..(8)
<223> OTHER INFORMATION: Ala, Ile, N-methyl isoleucine,
      cyclohexylglycine, cyclopentyl-glycine, Glu, Phe, Val, N-methyl-
      valine, tert-butylglycine, hexafluoroleucine, 3-Fluorovaline, 2-
      amino-4,4-difluoro-3-methylbutanoic acid, 3-fluoro-isoleucine, 4-
      fluoroisoleucine,
<220> FEATURE:
<221> NAME/KEY: MOD_RES
<222> LOCATION: (8)..(8)
<223> OTHER INFORMATION: cont'd from above; 5-fluoroisoleucine, (S)-
      leucinol, (S)-valinol, (S)-tert-leucinol, (R)-3-methylbutan-2-
      amine, (S)-2-methyl-1-phenylpropan-1-amine or (S)-N,2-dimethyl-1-
      (pyridin-2-yl) propan-1-amine
<220> FEATURE:
<221> NAME/KEY: MOD_RES
<222> LOCATION: (9)..(9)
<223> OTHER INFORMATION: Leu, Asn, Pro, Sar, N-methyl-alanine, N-methyl-
      leucine or absent
<220> FEATURE:
<221> NAME/KEY: MOD_RES
<222> LOCATION: (10)..(10)
<223> OTHER INFORMATION: Cys, D-Cys, penicillamine, Phe, 4-
      chlorophenylalanine, 4-fluoro-phenylalanine, 3-chlorotyrosine, 3-
      fluorotyrosine, Tyr, Pro, Arg, eta-omega methylated Arg, Lys,
      homolysine, (S)-2-amino-5-(3-methylguanidino) pentanoic acid, (S)-
      2-amino-3-(4-(aminomethyl)
<220> FEATURE:
<221> NAME/KEY: MOD_RES
<222> LOCATION: (10)..(10)
<223> OTHER INFORMATION: cont'd from above; phenyl)propanoic acid, (S)-
      2-amino-3-(3-(aminomethyl)phenyl)propanoic acid, 7-azatryptophan,
      (S)-2-amino-4-(2-aminobenzo[d]oxazol-5-yl)butanoic acid, a
      compound of formula I, a compound of formula II or absent
<220> FEATURE:
<221> NAME/KEY: MOD_RES
<222> LOCATION: (11)..(11)
<223> OTHER INFORMATION: Phe, 4-chlorophenylalanine, 4-
      fluorophenylalanine, 3-chloro-tyrosine, 3-fluorotyrosine, Tyr,
```

```
           Cys, D-Cys, penicillamine or absent
<220> FEATURE:
<221> NAME/KEY: MOD_RES
<222> LOCATION: (12)..(12)
<223> OTHER INFORMATION: Ser, Cys, D-Cys, homocysteine, penicillamine or
      absent
<220> FEATURE:
<221> NAME/KEY: MOD_RES
<222> LOCATION: (13)..(13)
<223> OTHER INFORMATION: Asp, Glu, Cys, D-Cys, penicillamine or absent
<220> FEATURE:
<223> OTHER INFORMATION: C-term may be -NH2, -N(CH3)2, -N-piperidine,
      -N-pyrrolidine, -N-N'-alkyl piperazine
<220> FEATURE:
<223> OTHER INFORMATION: see specification as filed for detailed
      description of substitutions and preferred embodiments

<400> SEQUENCE: 242

Xaa Xaa Xaa Xaa Xaa Xaa Xaa Xaa Xaa Xaa Xaa Xaa Xaa
1               5                   10

<210> SEQ ID NO 243
<211> LENGTH: 13
<212> TYPE: PRT
<213> ORGANISM: Artificial Sequence
<220> FEATURE:
<223> OTHER INFORMATION: Description of Artificial Sequence: Synthetic
      cyclic peptide
<220> FEATURE:
<223> OTHER INFORMATION: N-term may be H, acyl groups containing a
      linear or branched, saturated or unsaturated hydrocarbon chain
      from 1 to 20 carbon atoms, amides, carbamates, ureas, PEG or
      hydroxyalkyl starch
<220> FEATURE:
<221> NAME/KEY: MOD_RES
<222> LOCATION: (1)..(1)
<223> OTHER INFORMATION: Met, norvaline, Ala, Gly, Ser, Val, tert-
      butylglycine, Leu, phenylglycine, Ile, Pro, Trp, 7-azatryptophan,
      Phe, 4-fluoro-phenylalanine, Thr, Tyr, Lys, the N-methylated
      derivatives of these amino acids or absent
<220> FEATURE:
<221> NAME/KEY: MOD_RES
<222> LOCATION: (2)..(2)
<223> OTHER INFORMATION: Cys, penicillamine, des-aminoCys, D-Cys or
      homocysteine
<220> FEATURE:
<221> NAME/KEY: MOD_RES
<222> LOCATION: (3)..(3)
<223> OTHER INFORMATION: Ala, D-Ala, N-methyl-alanine, Glu, N-methyl-
      glutamate, D-Glu, Gly, sarcosine, norleucine, Lys, D-Lys, Asn, D-
      Asn, D-Glu, Arg, D-Arg, Phe, D-Phe, N-methyl-phenylalanine, Gln,
      D-Gln, Asp, D-Asp, Ser, D-Ser, N-methyl-serine, Thr, D-Thr, N-
      methyl-
<220> FEATURE:
<221> NAME/KEY: MOD_RES
<222> LOCATION: (3)..(3)
<223> OTHER INFORMATION: cont'd from above; threonine, Pro, D-Pro, Leu,
      D-Leu, N-methyl-leucine, Ile, D-Ile, N-methyl-isoleucine, Val, D-
      Val, N-methyl-valine, tert-butylglycine, D-tert-butylglycine, N-
      methyl-tert-butylglycine, Trp, D-Trp, N-methyl-tryptophan, Tyr,
      D-Tyr,
<220> FEATURE:
<221> NAME/KEY: MOD_RES
<222> LOCATION: (3)..(3)
<223> OTHER INFORMATION: cont'd from above; N-methyl-tyrosine, 1-
      aminocyclopropane-carboxylic acid, 1-aminocyclobutanecarboxylic
      acid, 1-amino-cyclopentanecarboxylic acid, 1-
      aminocyclohexanecarboxylic acid, 4-aminotetrahydro-2H-pyran-4-
      carboxylic acid, aminoisobutyric
<220> FEATURE:
<221> NAME/KEY: MOD_RES
<222> LOCATION: (3)..(3)
<223> OTHER INFORMATION: cont'd from above; acid, (S)-2-amino-3-(1H-
      tetrazol-5-yl) propanoic acid, Glu, Gly, N-methyl-glutamate, 2-
      amino pentanoic acid, 2-amino hexanoic acid, 2-amino heptanoic
      acid, 2-amino octanoic acid, 2-amino nonanoic acid, 2-amino
      decanoic acid,
```

```
<220> FEATURE:
<221> NAME/KEY: MOD_RES
<222> LOCATION: (3)..(3)
<223> OTHER INFORMATION: cont'd from above; 2-amino undecanoic acid, 2-
      amino dodecanoic acid, octylglycine, tranexamic acid, aminovaleric
      acid, 2-(2-aminoethoxy)acetic acid or absent
<220> FEATURE:
<221> NAME/KEY: MOD_RES
<222> LOCATION: (4)..(4)
<223> OTHER INFORMATION: Ala, N-methyl-alanine, Gly, sarcosine, Ser, N-
      methyl-serine, Pro, Thr, N-methyl-threonine, Val, N-methyl-valine,
      Ile, N-methyl-isoleucine, Phe, N-methyl-phenylalanine, 4-
      fluorophenyl-alanine, N-methyl-4-fluorophenylalanine, N-methyl-
      norleucine,
<220> FEATURE:
<221> NAME/KEY: MOD_RES
<222> LOCATION: (4)..(4)
<223> OTHER INFORMATION: cont'd from above; pipecolic acid, 2-carboxy
      azetidine or absent
<220> FEATURE:
<221> NAME/KEY: MOD_RES
<222> LOCATION: (5)..(5)
<223> OTHER INFORMATION: Ala, Phe, Ile, N-methyl-isoleucine, Asn, Val,
      cyclopentyl-glycine, cyclohexylglycine, cyclopropylglycine,
      phenylglycine, D-phenylglycine, tert-butylglycine,
      hexafluoroleucine, 3-Fluorovaline, 2-amino-4,4-difluoro-3-
      methylbutanoic acid,
<220> FEATURE:
<221> NAME/KEY: MOD_RES
<222> LOCATION: (5)..(5)
<223> OTHER INFORMATION: cont'd from above; 3-fluoro-isoleucine, 4-
      fluoroisoleucine, 5-fluoroisoleucine, 4-methyl-phenylglycine, 4-
      ethyl-phenyl-glycine or 4-isopropyl-phenylglycine
<220> FEATURE:
<221> NAME/KEY: MOD_RES
<222> LOCATION: (6)..(6)
<223> OTHER INFORMATION: Cys, D-Cys, homocysteine or penicillamine
<220> FEATURE:
<221> NAME/KEY: MOD_RES
<222> LOCATION: (7)..(7)
<223> OTHER INFORMATION: Arg, eta-omega methylated Arg, Lys, homolysine,
      (S)-2-amino-5-(3-methylguanidino) pentanoic acid, (S)-2-amino-3-
      (4-(amino-methyl)phenyl)propanoic acid, (S)-2-amino-3-(3-
      (aminomethyl) phenyl)propanoic acid, 7-azatryptophan, (S)-2-amino-
      4-(2-
<220> FEATURE:
<221> NAME/KEY: MOD_RES
<222> LOCATION: (7)..(7)
<223> OTHER INFORMATION: cont'd from above; aminobenzo[d]oxazol-5-
      yl)butanoic acid, a compound of formula I or a compound of formula
      II
<220> FEATURE:
<221> NAME/KEY: MOD_RES
<222> LOCATION: (8)..(8)
<223> OTHER INFORMATION: Ala, Ile, N-methyl isoleucine,
      cyclohexylglycine, cyclopentyl-glycine, Glu, Phe, Val, N-methyl-
      valine, tert-butylglycine, hexafluoroleucine, 3-Fluorovaline, 2-
      amino-4,4-difluoro-3-methylbutanoic acid, 3-fluoro-isoleucine, 4-
      fluoroisoleucine,
<220> FEATURE:
<221> NAME/KEY: MOD_RES
<222> LOCATION: (8)..(8)
<223> OTHER INFORMATION: cont'd from above; 5-fluoroisoleucine, (S)-
      leucinol, (S)-valinol, (S)-tert-leucinol, (R)-3-methylbutan-2-
      amine, (S)-2-methyl-1-phenylpropan-1-amine or (S)-N,2-dimethyl-1-
      (pyridin-2-yl) propan-1-amine
<220> FEATURE:
<221> NAME/KEY: MOD_RES
<222> LOCATION: (9)..(9)
<223> OTHER INFORMATION: Leu, Asn, Pro, Sar, N-methyl-alanine, N-methyl-
      leucine or absent
<220> FEATURE:
<221> NAME/KEY: MOD_RES
<222> LOCATION: (10)..(10)
<223> OTHER INFORMATION: Cys, D-Cys, penicillamine, Phe, 4-
      chlorophenylalanine, 4-fluoro-phenylalanine, 3-chlorotyrosine,
      3-fluorotyrosine, Tyr, Pro, Arg, eta-omega methylated Arg, Lys,
      homolysine, (S)-2-amino-5-(3-methylguanidino) pentanoic acid, (S)-
      2-amino-3-(4-(aminomethyl)
```

```
<220> FEATURE:
<221> NAME/KEY: MOD_RES
<222> LOCATION: (10)..(10)
<223> OTHER INFORMATION: cont'd from above; phenyl)propanoic acid, (S)-
      2-amino-3-(3-(aminomethyl)phenyl)propanoic acid, 7-azatryptophan,
      (S)-2-amino-4-(2-aminobenzo[d]oxazol-5-yl)butanoic acid, a
      compound of formula I, a compound of formula II or absent
<220> FEATURE:
<221> NAME/KEY: MOD_RES
<222> LOCATION: (11)..(11)
<223> OTHER INFORMATION: Phe, 4-chlorophenylalanine, 4-
      fluorophenylalanine, 3-chloro-tyrosine, 3-fluorotyrosine, Tyr,
      Cys, D-Cys, penicillamine or absent
<220> FEATURE:
<221> NAME/KEY: MOD_RES
<222> LOCATION: (12)..(12)
<223> OTHER INFORMATION: Ser, Cys, D-Cys, homocysteine, penicillamine or
      absent
<220> FEATURE:
<221> NAME/KEY: MOD_RES
<222> LOCATION: (13)..(13)
<223> OTHER INFORMATION: Asp, Glu, Cys, D-Cys, penicillamine or absent
<220> FEATURE:
<223> OTHER INFORMATION: C-term may be -NH2, -N(CH3)2, -N-piperidine,
      -N-pyrrolidine, -N-N'-alkyl piperazine
<220> FEATURE:
<223> OTHER INFORMATION: see specification as filed for detailed
      description of substitutions and preferred embodiments

<400> SEQUENCE: 243

Xaa Xaa Xaa Xaa Xaa Xaa Xaa Xaa Xaa Xaa Xaa Xaa Xaa
1               5                   10

<210> SEQ ID NO 244
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term may be H, acyl groups containing a
      linear or branched, saturated or unsaturated hydrocarbon chain
      from 1 to 20 carbon atoms, amides, carbamates, ureas, PEG or
      hydroxyalkyl starch
<220> FEATURE:
<221> NAME/KEY: MOD_RES
<222> LOCATION: (1)..(1)
<223> OTHER INFORMATION: Met, norvaline Ala, Gly, Ser, Val, tert-
      butylglycine, Leu, phenylglycine, Ile, Pro, Trp, 7-azatryptophan,
      Phe, 4-fluoro-phenylalanine, Thr, Tyr, Val, Lys, N-methyl-
      methionine, N-methyl-norvaline, N-methyl-alanine, sarcosine, N-
      methyl-tert-
<220> FEATURE:
<221> NAME/KEY: MOD_RES
<222> LOCATION: (1)..(1)
<223> OTHER INFORMATION: cont'd from above; butylglycine, N-methyl-
      leucine, N-methyl-phenylglycine, N-methyl-isoleucine, N-methyl-
      tryptophan, -methyl-7-azatryptophan, N-methyl-phenylalanine, N-
      methyl-4-fluorophenylalanine, N-methyl-threonine, N-methyl-
      tyrosine,
<220> FEATURE:
<221> NAME/KEY: MOD_RES
<222> LOCATION: (1)..(1)
<223> OTHER INFORMATION: cont'd from above; N-methyl-valine, N-methyl-
      lysine or absent
<220> FEATURE:
<221> NAME/KEY: MOD_RES
<222> LOCATION: (2)..(2)
<223> OTHER INFORMATION: sarcosine, Ala, D-Ala, N-methyl-alanine, Cys,
      D-Cys, N-methyl-cysteine, homocysteine, norvaline, D-norvaline, N-
      methyl-norvaline, Ser, D-Ser, N-methyl-serine, penicillamine
      or absent
```

```
<220> FEATURE:
<221> NAME/KEY: MOD_RES
<222> LOCATION: (3)..(3)
<223> OTHER INFORMATION: Asn, N-methyl-asparagine, Gln, N-methyl-
      glutamine, (S)-2-amino-3-(oxazol-2-yl)propanoic acid, (S)-2-amino-
      3-(oxazol-5-yl) propanoic acid, (S)-2-amino-3-(1,3,4-oxadiazol-2-
      yl)propanoic acid, (S)-2-amino-3-(1,2,4-oxadiazol-3-yl)propanoic
      acid, 4-
<220> FEATURE:
<221> NAME/KEY: MOD_RES
<222> LOCATION: (3)..(3)
<223> OTHER INFORMATION: cont'd from above; fluorophenylalanine, 3-
      chlorotyrosine, 3-fluorotyrosine, Tyr or Lys
<220> FEATURE:
<221> NAME/KEY: MOD_RES
<222> LOCATION: (4)..(4)
<223> OTHER INFORMATION: Phe, N-methyl-phenylalanine,
      4-chlorophenylalanine, 4-fluoro-phenylalanine, 3-chlorotyrosine,
      3-fluorotyrosine, Tyr, N-methyl-tyrosine or Ala
<220> FEATURE:
<221> NAME/KEY: MOD_RES
<222> LOCATION: (5)..(5)
<223> OTHER INFORMATION: Ala, N-methyl-alanine, Trp, N-methyl-
      tryptophan, 7-aza-tryptophan, 5-fluoro-tryptophan, 5-
      chlorotryptophan, (S)-2-amino-3-(5-fluoro-1H-indazol-3-yl)
      propanoic acid or (S)-2-amino-3-(1H-indazol-3-yl)propanoic acid
<220> FEATURE:
<221> NAME/KEY: MOD_RES
<222> LOCATION: (6)..(6)
<223> OTHER INFORMATION: Ser, N-methyl-serine, Thr, N-methyl-threonine
      or Ala
<220> FEATURE:
<221> NAME/KEY: MOD_RES
<222> LOCATION: (7)..(7)
<223> OTHER INFORMATION: N-methyl-alanine, sarcosine, N-methyl-serine,
      Pro, N-methyl-threonine, N-methyl-valine, N-methyl-isoleucine, N-
      methyl-leucine, N-methyl-phenylalanine, N-methyl-4-fluorophenyl-
      alanine, N-methyl-tyrosine, Leu or Ala
<220> FEATURE:
<221> NAME/KEY: MOD_RES
<222> LOCATION: (8)..(8)
<223> OTHER INFORMATION: Trp, N-methyl-tryptophan, 7-azatryptophan, 5-
      fluorotryptophan, 5-chlorotryptophan, (S)-2-amino-3-(5-fluoro-1H-
      indazol-3-yl) propanoic acid, (S)-2-amino-3-(1H-indazol-3-yl)
      propanoic acid, 4-fluorophenylalanine, 4-chlorophenylalanine,
      3-chlorotyrosine,
<220> FEATURE:
<221> NAME/KEY: MOD_RES
<222> LOCATION: (8)..(8)
<223> OTHER INFORMATION: cont'd from above; 3-fluorotyrosine, Tyr, N-
      methyl-tyrosine, Ala or absent
<220> FEATURE:
<221> NAME/KEY: MOD_RES
<222> LOCATION: (9)..(9)
<223> OTHER INFORMATION: Thr, N-methyl-threonine, tert-butylglycine,
      Ser, N-methyl-serine, Asn, (S)-2-amino-3-(oxazol-2-yl)propanoic
      acid, (S)-2-amino-3-(oxazol-5-yl)propanoic acid, (S)-2-amino-3-
      (1,3,4-oxadiazol-2-yl)propanoic acid, (S)-2-amino-3-(1,2,4-
<220> FEATURE:
<221> NAME/KEY: MOD_RES
<222> LOCATION: (9)..(9)
<223> OTHER INFORMATION: cont'd from above; oxadiazol-3-yl)propanoic
      acid or absent
<220> FEATURE:
<221> NAME/KEY: MOD_RES
<222> LOCATION: (10)..(10)
<223> OTHER INFORMATION: Ala, D-Ala, N-methyl-alanine, Glu, N-methyl-
      glutamate, D-Glu, Gly, sarcosine, norleucine, Lys, D-Lys, Asn, D-
      Asn, Arg, D-Arg, Phe, D-Phe, N-methyl-phenylalanine, Gln, D-Gln,
      Asp, D-Asp, Ser, D-Ser, N-methyl-serine, Thr, D-Thr, N-methyl-
      threonine, Pro, D-
<220> FEATURE:
<221> NAME/KEY: MOD_RES
<222> LOCATION: (10)..(10)
<223> OTHER INFORMATION: cont'd from above; Pro, Leu, D-Leu, N-methyl-
      leucine, Ile, D-Ile, N-methyl-isoleucine, Val, D-Val, N-methyl-
      valine, tert-butylglycine, D-tert-butylglycine, N-methyl-tert-
      butylglycine, Trp, D-Trp, N-methyl-tryptophan, Tyr, D-Tyr, N-
      methyl-tyrosine,
```

```
<220> FEATURE:
<221> NAME/KEY: MOD_RES
<222> LOCATION: (10)..(10)
<223> OTHER INFORMATION: cont'd from above; Cys, D-Cys, N-methyl-
      cysteine, penicillamine, homocysteine or absent
<220> FEATURE:
<221> NAME/KEY: MOD_RES
<222> LOCATION: (11)..(11)
<223> OTHER INFORMATION: Ala, D-Ala, N-methyl-alanine, Glu, N-methyl-
      glutamate, D-Glu, Gly, sarcosine, norleucine, Lys, D-Lys, Asn,
      D-Asn, Arg, D-Arg, Phe, D-Phe, N-methyl-phenylalanine, Gln, D-Gln,
      Asp, D-Asp, Ser, D-Ser, N-methyl-serine, Thr, D-Thr, N-methyl-
      threonine,
<220> FEATURE:
<221> NAME/KEY: MOD_RES
<222> LOCATION: (11)..(11)
<223> OTHER INFORMATION: cont'd from above; Pro, D-Pro, Leu, D-Leu,
      N-methyl-leucine, Ile, D-Ile, N-methyl-isoleucine, Val, D-Val,
      N-methyl-valine, tert-butylglycine, D-tert-butylglycine, N-methyl-
      tert-butyl-glycine, Trp, D-Trp, N-methyl-tryptophan, Tyr, D-Tyr,
<220> FEATURE:
<221> NAME/KEY: MOD_RES
<222> LOCATION: (11)..(11)
<223> OTHER INFORMATION: cont'd from above; N-methyl-tyrosine or absent
<220> FEATURE:
<221> NAME/KEY: MOD_RES
<222> LOCATION: (12)..(12)
<223> OTHER INFORMATION: Ala, D-Ala, N-methyl-alanine, Glu, N-methyl-
      glutamate, D-Glu, Gly, sarcosine, norleucine, Lys, D-Lys, Asn,
      D-Asn, Arg, D-Arg, Phe, D-Phe, N-methyl-phenylalanine, Gln, D-Gln,
      Asp, D-Asp, Ser, D-Ser, N-methyl-serine, Thr, D-Thr, N-methyl-
      threonine,
<220> FEATURE:
<221> NAME/KEY: MOD_RES
<222> LOCATION: (12)..(12)
<223> OTHER INFORMATION: cont'd from above; Pro, D-Pro, Leu, D-Leu, N-
      methyl-leucine, Ile, D-Ile, N-methyl-isoleucine, Val, D-Val, N-
      methyl-valine, tert-butylglycine, D-tert-butylglycine, N-methyl-
      tert-butyl-glycine, Trp, D-Trp, N-methyl-tryptophan, Tyr, D-Tyr,
      N-methyl-
<220> FEATURE:
<221> NAME/KEY: MOD_RES
<222> LOCATION: (12)..(12)
<223> OTHER INFORMATION: cont'd from above; tyrosine, phenylglycine,
      cyclohexylglycine or absent
<220> FEATURE:
<221> NAME/KEY: MOD_RES
<222> LOCATION: (13)..(13)
<223> OTHER INFORMATION: Cys, D-Cys, N-methyl-cysteine, homocysteine,
      penicillamine, Arg, Ala or absent
<220> FEATURE:
<223> OTHER INFORMATION: C-term may be -NH2, -NR1 (where R1 is any
      cyclic alkyl group or any linear alkyl group), PEG or hydroxyalkyl
      starch
<220> FEATURE:
<223> OTHER INFORMATION: see specification as filed for detailed
      description of substitutions and preferred embodiments

<400> SEQUENCE: 244

Xaa Xaa Xaa Xaa Xaa Xaa Xaa Xaa Xaa Xaa Xaa Xaa Xaa
1               5                   10

<210> SEQ ID NO 245
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term may be H, acyl groups containing a
      linear or branched, saturated or unsaturated hydrocarbon chain
      from 1 to 20 carbon atoms, amides, carbamates, ureas, PEG or
      hydroxyalkyl starch
```

```
<220> FEATURE:
<221> NAME/KEY: MOD_RES
<222> LOCATION: (1)..(1)
<223> OTHER INFORMATION: Met, norvaline Ala, Gly, Ser, Val, tert-
      butylglycine, Leu, phenylglycine, Ile, Pro, Trp, 7-azatryptophan,
      Phe, 4-fluoro-phenylalanine, Thr, Tyr, Val, Lys, N-methyl-
      methionine, N-methyl-norvaline, N-methyl-alanine, sarcosine,
      N-methyl-tert-
<220> FEATURE:
<221> NAME/KEY: MOD_RES
<222> LOCATION: (1)..(1)
<223> OTHER INFORMATION: cont'd from above; butylglycine, N-methyl-
      leucine, N-methyl-phenylglycine, N-methyl-isoleucine, N-methyl-
      tryptophan, N-methyl-7-azatryptophan, N-methyl-phenylalanine,
      N-methyl-4-fluorophenylalanine, N-methyl-threonine, N-methyl-
      tyrosine,
<220> FEATURE:
<221> NAME/KEY: MOD_RES
<222> LOCATION: (1)..(1)
<223> OTHER INFORMATION: cont'd from above; N-methyl-valine, N-methyl-
      lysine or absent
<220> FEATURE:
<221> NAME/KEY: MOD_RES
<222> LOCATION: (3)..(3)
<223> OTHER INFORMATION: Asn, N-methyl-asparagine, Gln, N-methyl-
      glutamine, (S)-2-amino-3-(oxazol-2-yl)propanoic acid, (S)-2-amino-
      3-(oxazol-5-yl) propanoic acid, (S)-2-amino-3-(1,3,4-oxadiazol-2-
      yl)propanoic acid, (S)-2-amino-3-(1,2,4-oxadiazol-3-yl)propanoic
      acid, 4-
<220> FEATURE:
<221> NAME/KEY: MOD_RES
<222> LOCATION: (3)..(3)
<223> OTHER INFORMATION: cont'd from above; fluorophenylalanine,
      3-chlorotyrosine, 3-fluorotyrosine, Tyr or Lys
<220> FEATURE:
<221> NAME/KEY: MOD_RES
<222> LOCATION: (4)..(4)
<223> OTHER INFORMATION: Phe, N-methyl-phenylalanine,
      4-chlorophenylalanine, 4-fluoro-phenylalanine, 3-chlorotyrosine,
      3-fluorotyrosine, Tyr, N-methyl-tyrosine or Ala
<220> FEATURE:
<221> NAME/KEY: MOD_RES
<222> LOCATION: (5)..(5)
<223> OTHER INFORMATION: Ala, N-methyl-alanine, Trp, N-methyl-
      tryptophan, 7-aza-tryptophan, 5-fluoro-tryptophan, 5-
      chlorotryptophan, (S)-2-amino-3-(5-fluoro-1H-indazol-3-
      yl)propanoic acid or (S)-2-amino-3-(1H-indazol-3-yl)propanoic acid
<220> FEATURE:
<221> NAME/KEY: MOD_RES
<222> LOCATION: (6)..(6)
<223> OTHER INFORMATION: Ser, N-methyl-serine, Thr, N-methyl-threonine
      or Ala
<220> FEATURE:
<221> NAME/KEY: MOD_RES
<222> LOCATION: (7)..(7)
<223> OTHER INFORMATION: N-methyl-alanine, sarcosine, N-methyl-serine,
      Pro, N-methyl-threonine, N-methyl-valine, N-methyl-isoleucine,
      N-methyl-leucine, N-methyl-phenylalanine, N-methyl-4-fluorophenyl-
      alanine, N-methyl-tyrosine, Leu or Ala
<220> FEATURE:
<221> NAME/KEY: MOD_RES
<222> LOCATION: (8)..(8)
<223> OTHER INFORMATION: Trp, N-methyl-tryptophan, 7-azatryptophan, 5-
      fluorotryptophan, 5-chlorotryptophan, (S)-2-amino-3-(5-fluoro-1H-
      indazol-3-yl) propanoic acid, (S)-2-amino-3-(1H-indazol-3-
      yl)propanoic acid, 4-fluorophenylalanine, 4-chlorophenylalanine,
      3-chlorotyrosine,
<220> FEATURE:
<221> NAME/KEY: MOD_RES
<222> LOCATION: (8)..(8)
<223> OTHER INFORMATION: cont'd from above; 3-fluorotyrosine, Tyr, N-
      methyl-tyrosine, Ala or absent
<220> FEATURE:
<221> NAME/KEY: MOD_RES
<222> LOCATION: (9)..(9)
<223> OTHER INFORMATION: Cys, D-Cys, N-methyl-cysteine, penicillamine,
      homocysteine, Thr, N-methyl-threonine, D-Thr, tert-butylglycine,
      Ser, Asn, (S)-2-amino-3-(oxazol-2-yl)propanoic acid, (S)-2-amino-
      3-(oxazol-5-yl)propanoic acid, (S)-2-amino-3-(1,3,4-oxadiazol-
```

-continued

```
<220> FEATURE:
<221> NAME/KEY: MOD_RES
<222> LOCATION: (9)..(9)
<223> OTHER INFORMATION: cont'd from above; 2-yl)propanoic acid, (S)-2-
      amino-3-(1,2,4-oxadiazol-3-yl)propanoic acid or absent
<220> FEATURE:
<221> NAME/KEY: MOD_RES
<222> LOCATION: (10)..(10)
<223> OTHER INFORMATION: Ala, D-Ala, N-methyl-alanine, Glu, N-methyl-
      glutamate, D-Glu, Gly, sarcosine, norleucine, Lys, D-Lys, Asn,
      D-Asn, Arg, D-Arg, Phe, D-Phe, N-methyl-phenylalanine, Gln, D-Gln,
      Asp, D-Asp, Ser, D-Ser, N-methyl-serine, Thr, D-Thr, N-methyl-
<220> FEATURE:
<221> NAME/KEY: MOD_RES
<222> LOCATION: (10)..(10)
<223> OTHER INFORMATION: cont'd from above; threonine, Pro, D-Pro, Leu,
      D-Leu, N-methyl-leucine, Ile, D-Ile, N-methyl-isoleucine, Val, D-
      Val, N-methyl-valine, tert-butylglycine, D-tert-butyl-
      glycine, N-methyl-tert-butylglycine, Trp, D-Trp, N-methyl-
<220> FEATURE:
<221> NAME/KEY: MOD_RES
<222> LOCATION: (10)..(10)
<223> OTHER INFORMATION: cont'd from above; tryptophan, Tyr, D-Tyr, N-
      methyl-tyrosine, Cys, D-Cys, N-methyl-cysteine, penicillamine,
      homocysteine or absent
<220> FEATURE:
<221> NAME/KEY: MOD_RES
<222> LOCATION: (11)..(11)
<223> OTHER INFORMATION: Ala, D-Ala, N-methyl-alanine, Glu, N-methyl-
      glutamate, D-Glu, Gly, sarcosine, norleucine, Lys, D-Lys, Asn,
      D-Asn, Arg, D-Arg, Phe, D-Phe, N-methyl-phenylalanine, Gln, D-Gln,
      Asp, D-Asp, Ser, D-Ser, N-methyl-serine, Thr, D-Thr, N-methyl-
<220> FEATURE:
<221> NAME/KEY: MOD_RES
<222> LOCATION: (11)..(11)
<223> OTHER INFORMATION: cont'd from above; threonine, Pro, D-Pro, Leu,
      D-Leu, N-methyl-leucine, Ile, D-Ile, N-methyl-isoleucine, Val, D-
      Val, N-methyl-valine, tert-butylglycine, D-tert-butylglycine, N-
      methyl-tert-butylglycine, Trp, D-Trp, N-methyl-tryptophan, Tyr,
      D-Tyr, and
<220> FEATURE:
<221> NAME/KEY: MOD_RES
<222> LOCATION: (11)..(11)
<223> OTHER INFORMATION: cont'd from above; N-methyl-tyrosine Cys, D-
      Cys, N-methyl-cysteine, penicillamine, homocysteine or absent
<220> FEATURE:
<221> NAME/KEY: MOD_RES
<222> LOCATION: (12)..(12)
<223> OTHER INFORMATION: Ala, D-Ala, N-methyl-alanine, Glu, N-methyl-
      glutamate, D-Glu, Gly, sarcosine, norleucine, Lys, D-Lys, Asn, D-
      Asn, Arg, D-Arg, Phe, D-Phe, N-methyl-phenylalanine, Gln, D-Gln,
      Asp, D-Asp, Ser, D-Ser, N-methyl-serine, Thr, D-Thr, N-methyl-
<220> FEATURE:
<221> NAME/KEY: MOD_RES
<222> LOCATION: (12)..(12)
<223> OTHER INFORMATION: cont'd from above; threonine, Pro, D-Pro, Leu,
      D-Leu, N-methyl-leucine, Ile, D-Ile, N-methyl-isoleucine, Val,
      D-Val, N-methyl-valine, tert-butylglycine, D-tert-butylglycine,
      N-methyl-tert-butylglycine, Trp, D-Trp, N-methyl-tryptophan, Tyr,
      D-Tyr, N-
<220> FEATURE:
<221> NAME/KEY: MOD_RES
<222> LOCATION: (12)..(12)
<223> OTHER INFORMATION: cont'd from above; methyl-tyrosine,
      phenylglycine, and cyclohexylglycine, Cys, D-Cys, N-methyl-
      cysteine, penicillamine, homocysteine or absent
<220> FEATURE:
<221> NAME/KEY: MOD_RES
<222> LOCATION: (13)..(13)
<223> OTHER INFORMATION: Cys, D-Cys, N-methyl-cysteine, homocysteine,
      penicillamine, Arg, Ala or absent
<220> FEATURE:
<223> OTHER INFORMATION: C-term may be -NH2, -NR1 (where R1 is any
      cyclic alkyl group or any linear alkyl group), PEG or hydroxyalkyl
      starch
<220> FEATURE:
<223> OTHER INFORMATION: see specification as filed for detailed
      description of substitutions and preferred embodiments
```

```
<400> SEQUENCE: 245

Xaa Cys Xaa Xaa Xaa Xaa Xaa Xaa Xaa Xaa Xaa Xaa Xaa
1               5                   10
```

PEPTIDE AND PEPTIDOMIMETIC INHIBITORS

CROSS REFERENCE TO RELATED APPLICATIONS

This application is a continuation of U.S. application Ser. No. 14/401,697 filed Nov. 17, 2014, which is a 35 U.S.C. §371 U.S. National Stage Entry of International Application No. PCT/US2013/031265 filed Mar. 14, 2013, which claims the benefit of U.S. Provisional Patent Application No. 61/648,155, filed May 17, 2012, the contents of each of which are incorporated herein by reference in their entirety.

REFERENCE TO SEQUENCE LISTING

The present application is being filed along with a Sequence Listing in electronic format. The Sequence Listing is provided as a file entitled 2011-1001USCONSEQLST.txt created on Dec. 7, 2015 which is 129,010 bytes in size. The information in electronic format of the Sequence Listing is incorporated herein by reference in its entirety.

FIELD OF THE INVENTION

The present invention relates to peptides. Specifically provided are peptides and peptidomimetics, whether cyclic or linear, having improved and beneficial characteristics as therapeutic compounds.

BACKGROUND OF THE INVENTION

Plasma kallikrein (EC.3.4.21.34) is a serine protease that is normally synthesized in the liver and circulates in the plasma by binding to high molecular weight kininogen (HMWK) or as prekallikrein, an inactive precursor (zymogen) of kallikrein. It is activated by proteolytic cleavage by Factor XIIa and contains an endopeptidase activity for cleaving peptide bonds after Arg or Lys residues.

Plasma kallikrein plays an important role in a variety of physiologic progresses, including, but not limited to, blood pressure regulation, the contact activation pathway of blood coagulation, fibrinolysis, inflammation, and pain.

The main physiologic regulator of kallikrein is C1 esterase inhibitor, or C1 INH. C1 INH is a potent inhibitor of Factor XIIa, and under normal conditions the inhibition of Factor XIIa prevents the conversion of prekallikrein to kallikrein and the subsequent generation of bradykinin from HMWK by activated kallikrein. Of note, patients with mutations that reduce C1 INH activity have inappropriately high plasma kallikrein activity that leads to elevated levels of bradykinin, a potent vasodilator and pain mediator. Thus, inherited C1 INH deficiency is the cause of hereditary angioedema (HAE), a debilitating and life-threatening condition characterized by severe swelling, edema, and pain.

Bradykinin is normally degraded by angiotensin converting enzyme (ACE), and patients treated with ACE inhibitors for blood pressure reduction may display elevated bradykinin levels and suffer from a syndrome termed acquired angioedema.

While HAE can be effectively controlled by administration of purified or recombinant C1 INH, it has been demonstrated that both plasma kallikrein inhibitors and bradykinin receptor antagonists are also effective in the treatment of HAE.

Elevated bradykinin levels are also associated with pain, inflammation, neutrophil recruitment, hypotension and septic shock. Furthermore, the inhibition of the kallikrein-bradykinin system may be useful in a variety of clinical situations, including, but not limited to, edemas (including diabetic macular edema, cerebral edema, and radiation-induced edema), diabetic retinopathy, retinal vein occlusion, intracerebral hemorrhage, stroke, systemic lupus, allergic rhinitis, controlling vascular leakage and blood loss during surgery, disseminated intravascular coagulation, inflammatory bowel disease, inflammation resulting from cardiopulmonary bypass, ischemia-reperfusion injury, and inflammatory or rheumatoid arthritis.

Given the many functional roles played by kallikrein, there remains a need for kallikrein inhibitors having pharmacokinetic and pharmacodynamic properties suitable for therapeutic application. The properties include, but are not limited to, high potency, high specificity for plasma kallikrein as compared to related protease, chemical and physical stability, ease of formulation, metabolic stability, appropriate pharmacokinetics, low toxicity, and good absorption from the intestinal tract (i.e. oral bioavailability).

SUMMARY OF THE INVENTION

The present invention provides for the production of peptides and peptide mimetics having improved pharmacokinetic and pharmacodynamic properties for inhibiting plasma kallikrein and their use in the treatment of diseases where reductions in circulating plasma kallikrein activity may be therapeutically beneficial.

In some embodiments, the present invention provides a peptide or peptide mimetic of the formula $R_1$-Xaa0-Xaa1-Xaa2-Xaa3-Xaa4-Xaa5-Xaa6-Xaa7-Xaa8-Xaa9-Xaa10-Xaa11-Xaa12-$R_2$, wherein: $R_1$ is selected from the group consisting of H, acyl groups containing a linear or branched, saturated or unsaturated hydrocarbon chain from 1 to 20 carbon atoms, amides, carbamates, ureas, PEG, hydroxyalkyl starch, polypeptides or proteins; Xaa0 is absent, or an amino acid selected from the group consisting of Met, norvaline, Ala, Gly, Ser, Val, tert-butylglycine, Leu, phenylglycine, Ile, Pro, Trp, 7-azatryptophan, Phe, 4-fluorophenylalanine, Thr, Tyr, Val, Lys, N-methyl-methionine, N-methyl-valine, N-methyl-alanine, sarcosine, N-methyl-tert-butylglycine, N-methyl-leucine, N-methyl-phenylglycine, N-methyl-isoleucine, N-methyl-tryptophan, N-methyl-7-azatryptophan, N-methyl-phenylalanine, N-methyl-4-fluorophenylalanine, N-methyl-threonine, N-methyl-tyrosine, N-methyl-valine, and N-methyl-lysine; Xaa1 is selected from the group consisting of Cys, penicillamine, des-amino-Cys, D-Cys, homocysteine, and Tyr; Xaa2 is absent, or an amino acid selected from the group consisting of Ala, D-Ala, N-methyl-alanine, Glu, N-methyl-glutamate, D-Glu, Gly, sarcosine, norleucine, Lys, D-Lys, Asn, D-Asn, D-Glu, Arg, D-Arg, Phe, D-Phe, N-methyl-phenylalanine, Gln, D-Gln, Asp, D-Asp, Ser, D-Ser, N-methyl-serine, Thr, D-Thr, N-methyl-threonine, Pro, D-Pro, Leu, D-Leu, N-methyl-leucine, Ile, D-Ile, N-methyl-isoleucine, Val, D-Val, N-methyl-valine, tert-butylglycine, D-tert-butylglycine, N-methyl-tert-butylglycine, Trp, D-Trp, N-methyl-tryptophan, Tyr, D-Tyr, N-methyl-tyrosine, 1-aminocyclopropanecarboxylic acid, 1-aminocyclobutanecarboxylic acid, 1-aminocyclopentanecarboxylic acid, 1-aminocyclohexanecarboxylic acid, 4-aminotetrahydro-2H-pyran-4-carboxylic acid, aminoisobutyric acid, (S)-2-amino-3-(1H-tetrazol-5-yl)propanoic acid, Glu, Gly, N-methyl-glutamate, 2-amino pentanoic acid, 2-amino hexanoic acid, 2-amino heptanoic acid, 2-amino octanoic acid, 2-amino nonanoic acid, 2-amino decanoic acid, 2-amino undecanoic acid, 2-amino dodecanoic acid, octylglycine, tranexamic acid, aminovaleric acid, and 2-(2-aminoethoxy)acetic acid; Xaa3 is absent, or an amino acid selected from the group consisting of Ala, N-methyl-alanine, Gly, sarcosine, Ser, N-methyl-serine, Pro, Thr, N-methyl-threonine, Val, N-methyl-valine, Ile, N-methyl-isoleucine, Phe, N-methyl-phenylalanine, 4-fluorophenylalanine, N-methyl-4-fluorophenylalanine, N-methyl-norleucine, pipecolic acid, and 2-carboxy azetidine; Xaa4 is an amino acid selected from the group consisting of Ala, Phe, Ile, N-methyl-isoleucine, Asn, Val, cyclopentylglycine, cyclohexylglycine, cyclopropylglycine, phenylglycine, D-phenylglycine, tert-butylglycine, hexafluoroleucine, 3-Fluorovaline, 2-amino-4,4-difluoro-3-methylbutanoic acid, 3-fluoro-isoleucine, 4-fluoroisoleucine, 5-fluoroisoleucine, 4-methyl-phenylglycine, 4-ethylphenylglycine, and 4-isopropyl-phenylglycine; Xaa5 is an amino acid selected from the group consisting of Cys, D-Cys, homocysteine, and penicillamine; Xaa6 is an amino acid selected from the group consisting of Arg, η-ω-methyl-arginine, Lys, homolysine, (S)-2-amino-5-(3-methylguanidino)pentanoic acid, (S)-2-amino-3-(4-(aminomethyl)phenyl)propanoic acid, (S)-2-amino-3-(3-(aminomethyl)phenyl)propanoic acid, 7-azatryptophan, (S)-2-amino-4-(2-aminobenzo[d]oxazol-5-yl)butanoic acid, a compound of formula I;

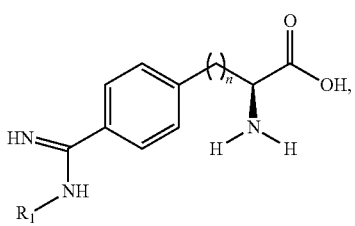

(I)

wherein n=1 or 2; $R_1$ is a hydrogen, a hydroxyl or an amine protecting group for example C1-6 alkoxycarbonyl, and compound of formula II;

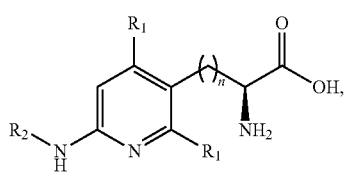

(II)

in which n=1 or 2, $R_1$ is a hydrogen or a methyl group and $R_2$ is a hydrogen or an amine protecting group, for example C1-6 alkoxycarbonyl; Xaa7 is an amino acid selected from the group consisting of Ala, Ile, N-methyl isoleucine, cyclohexylglycine, cyclopentylglycine, Glu, Phe, Val, N-methyl-valine, tert-butylglycine, hexafluoroleucine, 3-Fluorovaline, 2-amino-4,4-difluoro-3-methylbutanoic acid, 3-fluoro-isoleucine, 4-fluoroisoleucine, 5-fluoroisoleucine, (S)-leucinol, (S)-valinol, (S)-tert-leucinol, (R)-3-methylbutan-2-amine, (S)-2-methyl-1-phenylpropan-1-amine, and (S)—N,2-dimethyl-1-(pyridin-2-yl)propan-1-amine; Xaa8 is absent or an amino acid selected from the group consisting of Leu, Asn, Pro, Sar, N-methyl-alanine, and N-methyl-leucine; Xaa9 is absent or an amino acid selected from the group consisting of Cys, D-Cys, penicillamine, Phe, 4-chlorophenylalanine, 4-fluorophenylalanine, 3-chlorotyrosine, 3-fluorotyrosine, Tyr, Pro, Arg, η-ω-methyl-arginine, Lys, homolysine, (S)-2-amino-5-(3-methylguanidino)pentanoic acid, (S)-2-amino-3-(4-(aminomethyl)phenyl)propanoic acid, (S)-2-amino-3-(3-(aminomethyl)phenyl)propanoic acid, 7-azatryptophan, (S)-2-amino-4-(2-aminobenzo[d]oxazol-5-yl)butanoic acid, a compound of formula I in which n=1 or 2; $R_1$ is a hydrogen, a hydroxyl or an amine protecting group for example C1-6 alkoxycarbonyl, a compound of formula II in which n=1 or 2, $R_1$ is a hydrogen or a methyl group and $R_2$ is a hydrogen or an amine protecting group, for example C1-6 alkoxycarbonyl; Xaa10 is absent or an amino acid selected from the group consisting of Phe, 4-chlorophenylalanine, 4-fluorophenylalanine, 3-chlorotyrosine, 3-fluorotyrosine, Tyr, Cys, D-Cys, penicillamine; Xaa11 is absent or an amino acid selected from the group consisting of Ser, Cys, D-Cys, homocysteine, penicillamine; Xaa12 is absent, or an amino acid selected from the group consisting of Asp, Glu, Cys, D-Cys, penicillamine; and $R_2$ is absent or selected from the group consisting of —NH$_2$, —N(CH$_3$)$_2$, —N-piperidine, —N-pyrrolidine, —N—N'-alkyl piperazine.

In some embodiments, the present invention provides a peptide or peptide mimetic of the formula $R_1$-Xaa0-Xaa1-Xaa2-Xaa3-Xaa4-Xaa5-Xaa6-Xaa7-Xaa8-Xaa9-Xaa10-Xaa11-Xaa12-$R_2$, wherein: $R_1$ is selected from the group consisting of H, acyl groups containing a linear or branched, saturated or unsaturated hydrocarbon chain from 1 to 20 carbon atoms, amides, carbamates, ureas, PEG, hydroxyalkyl starch, polypeptides or proteins; Xaa0 is absent, or an amino acid selected from the group consisting of Met, norvaline, Ala, Gly, Ser, Val, tert-butylglycine, Leu, phenylglycine, Ile, Pro, Trp, 7-azatryptophan, Phe, 4-fluorophenylalanine, Thr, Tyr, Lys and the N-methylated derivatives of these amino acids; Xaa1 is selected from the group consisting of Cys, penicillamine, des-aminoCys, D-Cys, and homocysteine; Xaa2 is absent, or an amino acid selected from the group consisting of Ala, D-Ala, N-methyl-alanine, Glu, N-methyl-glutamate, D-Glu, Gly, sarcosine, norleucine, Lys, D-Lys, Asn, D-Asn, D-Glu, Arg, D-Arg, Phe, D-Phe, N-methyl-phenylalanine, Gln, D-Gln, Asp, D-Asp, Ser, D-Ser, N-methyl-serine, Thr, D-Thr, N-methyl-threonine, Pro, D-Pro, Leu, D-Leu, N-methyl-leucine, Ile, D-Ile, N-methyl-isoleucine, Val, D-Val, N-methyl-valine, tert-butylglycine, D-tert-butylglycine, N-methyl-tert-butylglycine, Trp, D-Trp, N-methyl-tryptophan, Tyr, D-Tyr, N-methyl-tyrosine, 1-aminocyclopropanecarboxylic acid, 1-aminocyclobutanecarboxylic acid, 1-aminocyclopentanecarboxylic acid, 1-aminocyclohexanecarboxylic acid, 4-aminotetrahydro-2H-pyran-4-carboxylic acid, aminoisobutyric acid, (S)-2-amino-3-(1H-tetrazol-5-yl)propanoic acid, Glu, Gly, N-methyl-glutamate, 2-amino pentanoic acid, 2-amino hexanoic acid, 2-amino heptanoic acid, 2-amino octanoic acid, 2-amino nonanoic acid, 2-amino decanoic acid, 2-amino undecanoic acid, 2-amino dodecanoic acid, octylglycine, tranexamic acid, aminovaleric acid, and 2-(2-aminoethoxy)acetic acid; Xaa3 is absent, or an amino acid selected from the group consisting of Ala, N-methyl-alanine, Gly, sarcosine, Ser, N-methyl-serine, Pro, Thr, N-methyl-valine, Ile, N-methyl-isoleucine, Phe, N-methyl-phenylalanine, 4-fluorophenylalanine, N-methyl-4-fluorophenylalanine, N-methyl-norleucine, pipecolic acid, and 2-carboxy azetidine; Xaa4 is an amino acid selected from the group consisting of Ala, Phe, Ile, N-methyl-isoleucine, Asn, Val, cyclopentylglycine, cyclohexylglycine, cyclopropylglycine, phenylglycine, D-phenylglycine, tert-butylglycine, hexafluoroleucine, 3-Fluorovaline, 2-amino-4,4-difluoro-3-methylbutanoic acid, 3-fluoro-isoleucine, 4-fluoroisoleucine, 5-fluoroisoleucine, 4-methyl-phenylglycine, 4-ethyl-phenylglycine, and 4-isopropyl-phenylglycine; Xaa5 is an amino acid selected from the group consisting of Cys, D-Cys, homocysteine, and penicillamine; Xaa6 is an amino acid selected from the group consisting of Arg, η-ω-methyl-arginine, Lys, homolysine, (S)-2-amino-5-(3-methylguanidino)pentanoic acid, (S)-2-amino-3-(4-(aminomethyl)phenyl)propanoic acid, (S)-2-amino-3-(3-(aminomethyl)phenyl)propanoic acid, 7-azatryptophan, (S)-2-amino-4-(2-aminobenzo[d]oxazol-5-yl)butanoic acid, a compound of formula I;

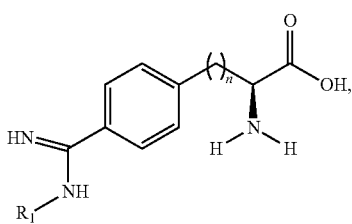

(I)

wherein n=1 or 2; $R_1$ is a hydrogen, a hydroxyl or an amine protecting group for example C1-6 alkoxycarbonyl, and compound of formula II;

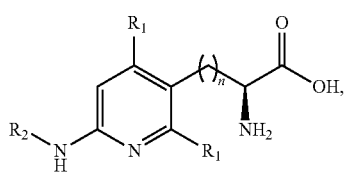

(II)

in which n=1 or 2, $R_1$ is a hydrogen or a methyl group and $R_2$ is a hydrogen or an amine protecting group, for example C1-6 alkoxycarbonyl; Xaa7 is an amino acid selected from the group consisting of Ala, Ile, N-methyl-isoleucine, cyclohexylglycine, cyclopentylglycine, Glu, Phe, Val, N-methylvaline, tert-butylglycine, hexafluoroleucine, 3-Fluorovaline, 2-amino-4,4-difluoro-3-methylbutanoic acid, 3-fluoro-isoleucine, 4-fluoroisoleucine, 5-fluoroisoleucine, (S)-leucinol, (S)-valinol, (S)-tert-leucinol, (R)-3-methylbutan-2-amine, (S)-2-methyl-1-phenylpropan-1-amine, and (S)—N,2-dimethyl-1-(pyridin-2-yl)propan-1-amine; Xaa8 is absent or an amino acid selected from the group consisting of Leu, Asn, Pro, Sar, N-methyl-alanine, and N-methyl-leucine; Xaa9 is absent or an amino acid selected from the group consisting of Cys, D-Cys, penicillamine, Phe, 4-chlorophenylalanine, 4-fluorophenylalanine, 3-chlorotyrosine, 3-fluorotyrosine, Tyr, Pro, Arg, η-ω-methyl-arginine, Lys, homolysine, (S)-2-amino-5-(3-methylguanidino)pentanoic acid, (S)-2-amino-3-(4-(aminomethyl)phenyl)propanoic acid, (S)-2-amino-3-(3-(aminomethyl)phenyl)propanoic acid, 7-azatryptophan, (S)-2-amino-4-(2-aminobenzo[d]oxazol-5-yl)butanoic acid, a compound of formula I in which n=1 or 2; $R_1$ is a hydrogen, a hydroxyl or an amine protecting group for example C1-6 alkoxycarbonyl, a compound of formula II in which n=1 or 2, $R_1$ is a hydrogen or a methyl group and $R_2$ is a hydrogen or an amine protecting group, for example C1-6 alkoxycarbonyl; Xaa10 is absent or an amino acid selected from the group consisting of Phe, 4-chlorophenylalanine, 4-fluorophenylalanine, 3-chlorotyrosine, 3-fluorotyrosine, Tyr, Cys, D-Cys, penicillamine; Xaa11 is absent or an amino acid selected from the group consisting of Ser, Cys, D-Cys, homocysteine, penicillamine; Xaa12 is absent, or an amino acid selected from the group consisting of Asp, Glu, Cys, D-Cys, penicillamine; and $R_2$ is absent or selected from the group consisting of —NH$_2$, —N(CH$_3$)$_2$, —N-piperidine, —N-pyrrolidine, —N—N'-alkyl piperazine.

In some embodiments, the peptides or peptide mimetics of the present invention are cyclized by a reaction of the residues Xaa1 and Xaa5 with a reagent. In some embodiments, cyclic peptides or cyclic peptide mimetics are cyclized with a reagent selected from the group consisting of: 1,2-bis(bromomethyl)benzene, 1,3-bis(bromomethyl)benzene, 1,4-bis(bromomethyl)benzene, 2,6-bis(bromomethyl)pyridine, and (E)-1,4-dibromobut-2-ene, 1,2-bis(bromomethyl)-4-alkylbenzene, wherein the alkyl group contains between 1 and 22 carbon atoms. In some embodiments, the peptides or peptide mimetics of the present invention are cyclized by a reaction of the residues Xaa1, Xaa5 and either Xaa9 or Xaa11 or Xaa12 with tris(bromomethyl)benzene.

In some embodiments, peptides or peptide mimetics of the present invention comprise the amino acid sequence: $R_1$ Xaa0 Xaa1 Xaa2 Xaa3 Xaa4 Xaa5 Xaa6 Xaa7 Xaa8 Xaa9 Xaa10 Xaa11 Xaa12 $R_2$ wherein: $R_1$ is selected from the group consisting of H, acyl groups containing a linear or branched, saturated or unsaturated hydrocarbon chain from 1 to 20 carbon atoms, amides, carbamates, ureas, PEG, hydroxyalkyl starch, polypeptides or proteins; Xaa0 is absent, or an amino acid selected from the group consisting of Met, norvaline Ala, Gly, Ser, Val, tert-butylglycine, Leu, phenylglycine, Ile, Pro, Trp, 7-azatryptophan, Phe, 4-fluorophenylalanine, Thr, Tyr, Val, Lys, N-methyl-methionine, N-methyl-norvaline, N-methyl-alanine, sarcosine, N-methyl-tert-butylglycine, N-methyl-leucine, N-methyl-phenylglycine, N-methyl-isoleucine, N-methyl-tryptophan, -methyl-7-azatryptophan, N-methyl-phenylalanine, N-methyl-4-fluorophenylalanine, N-methyl-threonine, N-methyl-tyrosine, N-methyl-valine, and N-methyl-lysine; Xaa1 is absent or an amino acid selected from the group consisting of sarcosine, Ala, D-Ala, N-methyl-alanine, Cys, D-Cys, N-methyl-cysteine, homocysteine, norvaline, D-norvaline, N-methyl-norvaline, Ser, D-Ser, N-methyl-serine, and penicillamine; Xaa2 is an amino acid selected from the group consisting of Asn, N-methyl-asparagine, Gln, N-methyl-glutamine, (S)-2-amino-3-(oxazol-2-yl)propanoic acid, (S)-2-amino-3-(oxazol-5-yl)propanoic acid, (S)-2-amino-3-(1,3,4-oxadiazol-2-yl)propanoic acid, (S)-2-amino-3-(1,2,4-oxadiazol-3-yl)propanoic acid, 4-fluorophenylalanine, 3-chlorotyrosine, 3-fluorotyrosine, Tyr, and Lys; Xaa3 is an amino acid selected from the group consisting of Phe, N-methyl-phenylalanine, 4-chlorophenylalanine, 4-fluorophenylalanine, 3-chlorotyrosine, 3-fluorotyrosine, Tyr, N-methyl-tyrosine, and Ala; Xaa4 is an amino acid selected from the group consisting of Ala, N-methyl-alanine, Trp, N-methyl-tryptophan, 7-azatryptophan, 5-fluoro-tryptophan, 5-chlorotryptophan, (S)-2-amino-3-(5-fluoro-1H-indazol-3-yl)propanoic acid, and (S)-2-amino-3-(1H-indazol-3-yl)propanoic acid; Xaa5 is an amino acid selected from the group consisting of Ser, N-methyl-serine, Thr, N-methyl-threonine, and Ala; Xaa6 is an amino acid selected from the group consisting of N-methyl-alanine, sarcosine, N-methyl-serine, Pro, N-methyl-threonine, N-methyl-valine, N-methyl-isoleucine, N-methyl-leucine, N-methyl-phenylalanine, N-methyl-4-fluorophenylalanine, N-methyl-tyrosine, Leu, and Ala; Xaa7 is absent or an amino acid selected from the group consisting of Trp, N-methyl-tryptophan, 7-azatryptophan, 5-fluorotryptophan, 5-chlorotryptophan, (S)-2-amino-3-(5-fluoro-1H-indazol-3-yl)propanoic acid, (S)-2-amino-3-(1H-indazol-3-yl)propanoic acid, 4-fluorophenylalanine, 4-chlorophenylalanine, 3-chlorotyrosine, 3-fluorotyrosine, Tyr, N-methyl-tyrosine, and Ala; Xaa8 is absent or an amino acid selected from the group consisting of Thr, N-methyl-threonine, tert-butylglycine, Ser, N-methyl-serine, Asn, (S)-2-amino-3-(oxazol-2-yl)propanoic acid, (S)-2-amino-3-(oxazol-5-yl)propanoic acid, (S)-2-amino-3-(1,3,4-oxadiazol-2-yl)propanoic acid, and (S)-2-amino-3-(1,2,4-oxadiazol-3-yl)propanoic acid; Xaa9 is absent or an amino acid selected from the group consisting of Ala, D-Ala, N-methyl-alanine, Glu, N-methyl-glutamate, D-Glu, Gly, sarcosine, norleucine, Lys, D-Lys, Asn, D-Asn, Arg, D-Arg, Phe, D-Phe, N-methyl-phenylalanine, Gln, D-Gln, Asp, D-Asp, Ser, D-Ser, N-methyl-serine, Thr, D-Thr, N-methyl-threonine, Pro, D-Pro, Leu, D-Leu, N-methyl-leucine, Ile, D-Ile, N-methyl-isoleucine, Val, D-Val, N-methyl-valine, tert-butylglycine, D-tert-butylglycine, N-methyl-tert-butylglycine, Trp, D-Trp, N-methyl-tryptophan, Tyr, D-Tyr, N-methyl-tyrosine, Cys, D-Cys, N-methyl-cysteine, penicillamine, and homocysteine; Xaa10 is absent or an amino acid selected from the group consisting of Ala, D-Ala, N-methyl-alanine, Glu, N-methyl-glutamate, D-Glu, Gly, sarcosine, norleucine, Lys, D-Lys, Asn, D-Asn, Arg, D-Arg, Phe, D-Phe, N-methyl-phenylalanine, Gln, D-Gln, Asp, D-Asp, Ser, D-Ser, N-methyl-serine, Thr, D-Thr, N-methyl-threonine, Pro, D-Pro, Leu, D-Leu, N-methyl-leucine, Ile, D-Ile, N-methyl-isoleucine, Val, D-Val, N-methyl-valine, tert-butylglycine, D-tert-butylglycine, N-methyl-tert-butylglycine, Trp, D-Trp, N-methyl-tryptophan, Tyr, D-Tyr, and N-methyl-tyrosine; Xaa11 is absent or an amino acid selected from the group consisting of Ala, D-Ala, N-methyl-alanine, Glu, N-methyl-glutamate, D-Glu, Gly, sarcosine, norleucine, Lys, D-Lys, Asn, D-Asn, Arg, D-Arg, Phe, D-Phe, N-methyl-phenylalanine, Gln, D-Gln, Asp, D-Asp, Ser, D-Ser, N-methyl-serine, Thr, D-Thr, N-methyl-threonine, Pro, D-Pro, Leu, D-Leu, N-methyl-leucine, Ile, D-Ile, N-methyl-isoleucine, Val, D-Val, N-methyl-valine, tert-butylglycine, D-tert-butylglycine, N-methyl-tert-butylglycine, Trp, D-Trp, N-methyl-tryptophan, Tyr, D-Tyr, N-methyl-tyrosine, phenylglycine, and cyclohexylglycine; Xaa12 is absent, or an amino acid selected from the group consisting of Cys, D-Cys, N-methyl-cysteine, homocysteine, penicillamine, Arg, and Ala; and $R_2$ is absent or selected from the group consisting of —$NH_2$, —$NR_1$ (where $R_1$ is any cyclic alkyl group or any linear alkyl group), PEG, hydroxyalkyl starch, polypeptides, and proteins.

In some embodiments, the peptides or peptide mimetics of the present invention comprise the amino acid sequence $R_1$ Xaa0 Cys Xaa2 Xaa3 Xaa4 Xaa5 Xaa6 Xaa7 Xaa8 Xaa9 Xaa10 Xaa11 Xaa12 $R_2$ wherein, $R_1$ is selected from the group consisting of H, acyl groups containing a linear or branched, saturated or unsaturated hydrocarbon chain from 1 to 20 carbon atoms, amides, carbamates, ureas, PEG, hydroxyalkyl starch, polypeptides or proteins; Xaa0 is absent, or an amino acid selected from the group consisting of Met, norvaline Ala, Gly, Ser, Val, tert-butylglycine, Leu, phenylglycine, Ile, Pro, Trp, 7-azatryptophan, Phe, 4-fluorophenylalanine, Thr, Tyr, Val, Lys, N-methyl-methionine, N-methyl-norvaline, N-methyl-alanine, sarcosine, N-methyl-tert-butylglycine, N-methyl-leucine, N-methyl-phenylglycine, N-methyl-isoleucine, N-methyl-tryptophan, N-methyl-7-azatryptophan, N-methyl-phenylalanine, N-methyl-4-fluorophenylalanine, N-methyl-threonine, N-methyl-tyrosine, N-methyl-valine, and N-methyl-lysine; Xaa1 is absent an amino acid selected from the group consisting of sarcosine, Ala, D-Ala, N-methyl-alanine, Cys, D-Cys, N-methyl-cysteine, penicillamine, homocysteine, norvaline, D-norvaline, N-methyl-norvaline, Ser, D-Ser, and N-methyl-serine; Xaa2 is an amino acid selected from the group consisting of Asn, N-methyl-asparagine, Gln, N-methyl-glutamine, (S)-2-amino-3-(oxazol-2-yl)propanoic acid, (S)-2-amino-3-(oxazol-5-yl)propanoic acid, (S)-2-amino-3-(1,3,4-oxadiazol-2-yl)propanoic acid, (S)-2-amino-3-(1,2,4-oxadiazol-3-yl)propanoic acid, 4-fluorophenylalanine, 3-chlorotyrosine, 3-fluorotyrosine, Tyr, and Lys; Xaa3 is an amino acid selected from the group consisting of Phe, N-methyl-phenylalanine, 4-chlorophenylalanine, 4-fluorophenylalanine, 3-chlorotyrosine, 3-fluorotyrosine, Tyr, N-methyl-tyrosine, and Ala; Xaa4 is an amino acid selected from the group consisting of Ala, N-methyl-alanine, Trp, N-methyl-tryptophan, 7-azatryptophan, 5-fluoro-tryptophan, 5-chlorotryptophan, (S)-2-amino-3-(5-fluoro-1H-indazol-3-yl)propanoic acid, and (S)-2-amino-3-(1H-indazol-3-yl)propanoic acid; Xaa5 is an amino acid selected from the group consisting of Ser, N-methyl-serine, Thr, N-methyl-threonine, and Ala; Xaa6 is an amino acid selected from the group consisting of N-methyl-alanine, sarcosine, N-methyl-serine, Pro, N-methyl-threonine, N-methyl-valine, N-methyl-isoleucine, N-methyl-leucine, N-methyl-phenylalanine, N-methyl-4-fluorophenylalanine, N-methyl-tyrosine, Leu, and Ala; Xaa7 is absent or an amino acid selected from the group consisting of Trp, N-methyl-tryptophan, 7-azatryptophan, 5-fluorotryptophan, (S)-2-amino-3-(5-fluoro-1H-indazol-3-yl)propanoic acid, (S)-2-amino-3-(1H-indazol-3-yl)propanoic acid, 4-fluorophenylalanine, 4-chlorophenylalanine, 3-chlorotyrosine, 3-fluorotyrosine, 5-chlorotryptophan, Tyr, N-methyl-tyrosine, and Ala; Xaa8 is absent or an amino acid selected from the group Cys, D-Cys, N-methyl-cysteine, penicillamine, homocysteine, Thr, N-methyl-threonine, D-Thr, tert-butylglycine, Ser, Asn, (S)-2-amino-3-(oxazol-2-yl)propanoic acid, (S)-2-amino-3-(oxazol-5-yl)propanoic acid, (S)-2-amino-3-(1,3,4-oxadiazol-2-yl)propanoic acid, (S)-2-amino-3-(1,2,4-oxadiazol-3-yl)propanoic acid; Xaa9 is absent or an amino acid selected from the group consisting of Ala, D-Ala, N-methyl-alanine, Glu, N-methyl-glutamate, D-Glu, Gly, sarcosine, norleucine, Lys, D-Lys, Asn, D-Asn, Arg, D-Arg, Phe, D-Phe, N-methyl-phenylalanine, Gln, D-Gln, Asp, D-Asp, Ser, D-Ser, N-methyl-serine, Thr, D-Thr, N-methyl-threonine, Pro, D-Pro, Leu, D-Leu, N-methyl-leucine, Ile, D-Ile, N-methyl-isoleucine, Val, D-Val, N-methyl-valine, tert-butylglycine, D-tert-butylglycine, N-methyl-tert-butylglycine, Trp, D-Trp, N-methyl-tryptophan, Tyr, D-Tyr, N-methyl-tyrosine, Cys, D-Cys, N-methyl-cysteine, penicillamine, and homocysteine; Xaa10 is absent or an amino acid selected from the group consisting of Ala, D-Ala, N-methyl-alanine, Glu, N-methyl-glutamate, D-Glu, Gly, sarcosine, norleucine, Lys, D-Lys, Asn, D-Asn, Arg, D-Arg, Phe, D-Phe, N-methyl-phenylalanine, Gln, D-Gln, Asp, D-Asp, Ser, D-Ser, N-methyl-serine, Thr, D-Thr, N-methyl-threonine, Pro, D-Pro, Leu, D-Leu, N-methyl-leucine, Ile, D-Ile, N-methyl-isoleucine, Val, D-Val, N-methyl-valine, tert-butylglycine, D-tert-butylglycine, N-methyl-tert-butylglycine, Trp, D-Trp, N-methyl-tryptophan, Tyr, D-Tyr, and N-methyl-tyrosine Cys, D-Cys, N-methyl-cysteine, penicillamine, and homocysteine; Xaa11 is absent or an amino acid selected from the group consisting of Ala, D-Ala, N-methyl-alanine, Glu, N-methyl-glutamate, D-Glu, Gly, sarcosine, norleucine, Lys, D-Lys, Asn, D-Asn, Arg, D-Arg, Phe, D-Phe, N-methyl-phenylalanine, Gln, D-Gln, Asp, D-Asp, Ser, D-Ser, N-methyl-serine, Thr, D-Thr, N-methyl-threonine, Pro, D-Pro, Leu, D-Leu, N-methyl-leucine, Ile, D-Ile, N-methyl-isoleucine, Val, D-Val, N-methyl-valine, tert-butylglycine, D-tert-butylglycine, N-methyl-tert-butylglycine, Trp, D-Trp, N-methyl-tryptophan, Tyr, D-Tyr, N-methyl-tyrosine, phenylglycine, and cyclohexylglycine, Cys, D-Cys, N-methyl-cysteine, penicillamine, and homocysteine; Xaa12 is absent, or an amino acid selected from the group Cys, D-Cys, N-methyl-cysteine, penicillamine, homocysteine, Arg, and Ala; and $R_2$ is absent or selected from the group consisting of —$NH_2$, —$NR_1$ (where $R_1$ is any cyclic alkyl group or any linear alkyl group), PEG, hydroxyalkyl starch, polypeptides, and proteins.

In one embodiment, the peptides and/or peptide mimetics described herein may be serine protease inhibitors. In one embodiment, the serine protease is plasma kallikrein.

In some embodiments, peptide or peptide mimetics are provided, wherein one of the residues at positions Xaa8, Xaa9, Xaa10, Xaa11 or Xaa12 is selected from the group consisting of Cys, D-Cys, N-methyl-cysteine, penicillamine, and homocysteine. In some embodiments, peptide or peptide mimetics are provided, wherein the residue at position Xaa1 is selected from the group consisting of Cys, D-Cys, N-methyl-cysteine, penicillamine, and homocysteine. In some embodiments, peptide or peptide mimetics are provided, wherein the peptide or peptide mimetic is cyclized by a reaction with a thiol-reactive reagent. In some embodiments, peptide or peptide mimetics are provided, wherein the reagent is selected from the group consisting of: 1,2-bis(bromomethyl)benzene, 1,3-bis(bromomethyl)benzene, 1,4-bis(bromomethyl)benzene, 2,6-bis(bromomethyl)pyridine, substituted bis(bromomethyl)benzenes and (E)-1,4-dibromobut-2-ene. In some embodiments, peptide or peptide mimetics are provided, wherein the reagent is 1,3-bis(bromomethyl)benzene.

In some embodiments, peptide or peptide mimetics are provided, wherein a loop is formed between two cysteine residues. In some embodiments, peptide or peptide mimetics are provided, wherein the loop comprises a bridging moiety selected from the group consisting of:

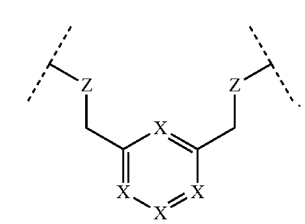

I

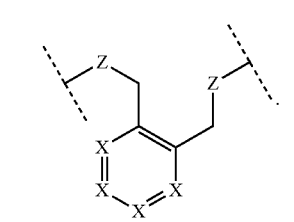

II

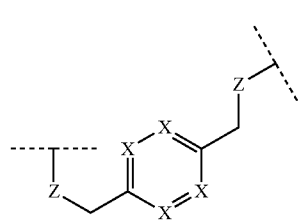

III

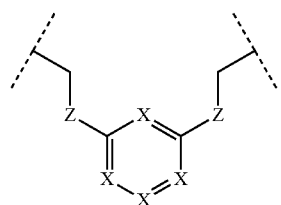

IV

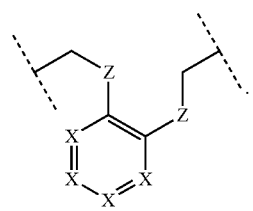

V

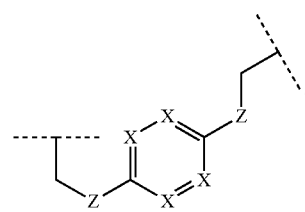

VI

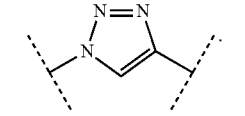

VII

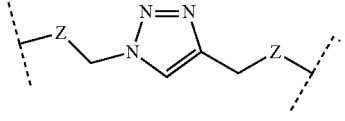

VIII

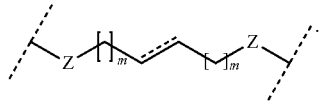

IX

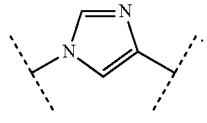

X

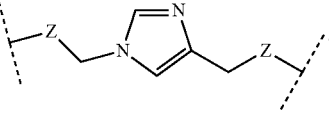

XI

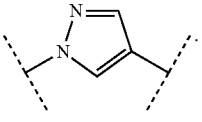

XII

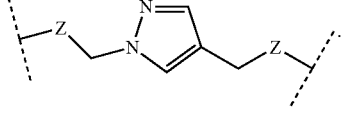

XIII

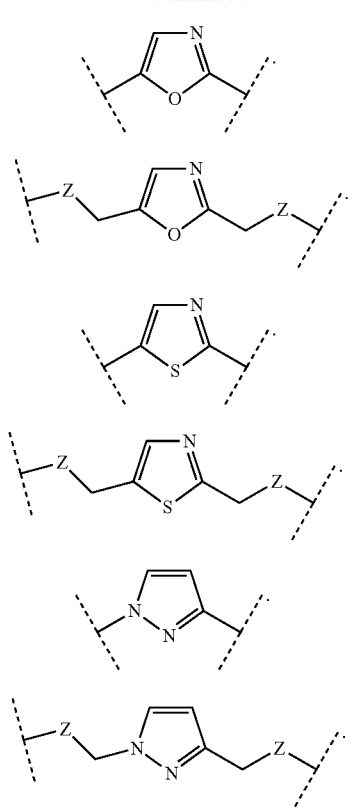

In some embodiments, peptide or peptide mimetics are provided comprising a cyclic loop formed according to a method comprising one or more chemical reactions selected from the group consisting of a Heck reaction, a Buchwald reaction and an Olefin metathesis.

In some embodiments, a method is provided for the treatment or prevention of suffering from hereditary angioedema in a subject comprising the administration to said subject in need thereof of a therapeutically effective amount of one or more serine protease inhibitors. In some embodiments, such methods are characterized in that the serine protease is plasma kallikrein and the one or more serine protease inhibitors are peptide or peptide mimetics of the present invention. In some embodiments, methods are provided wherein administration is selected from the group consisting of oral, intravenous, intramuscular, intraperitoneal, subcutaneous, transdermal, and intravitreal. In some embodiments, methods are provided wherein the inhibitor of plasma kallikrein is conjugated to a water soluble polymer. In some embodiments, methods are provided wherein the water soluble polymer is a hydrophilic polymer. In some embodiments, methods are provided wherein the hydrophilic polymer is selected from the group consisting of polyalkylene oxide homopolymers, polypropylene glycols, polyoxyethylenated polyols, and copolymers thereof. In some embodiments, methods are provided wherein the water soluble polymer is polyethylene glycol (PEG).

In some embodiments, present invention provides a pharmaceutical composition comprising one or more of the peptides or peptide mimetics of the present invention, and a pharmaceutically acceptable carrier or excipient. In some embodiments, present invention provides a kit for the diagnosis, prognosis, prophylaxis or treatment of hereditary angioedema in a mammal, characterized in that said kit comprises one or more plasma kallikrein inhibitors, optionally with reagents and/or instructions for use, wherein said one or more plasma kallikrein inhibitors comprise; a sequence of at least 8 contiguous amino acids of any of the peptides or peptide mimetics of the present invention. In some embodiments, kits are provided wherein the one or more plasma kallikrein inhibitors comprise a detectable label or can bind to a detectable label to form a detectable complex.

In some embodiments, peptide or peptide mimetics are provided having kallikrein inhibitory activity of less than 100 nM $IC_{50}$, 50 nM $IC_{50}$, 20 nM $IC_{50}$, 10 nM $IC_{50}$, 5 nM $IC_{50}$ and/or 1 nM $IC_{50}$. In some embodiments, such peptides or peptide mimetics are cyclic. In some embodiments, peptide or peptide mimetics are provided having an $IC_{50}$ of less than 50 nM and/or less than 10 nM against human kallikrein. In some embodiments, peptide or peptide mimetics are provided having an $IC_{50}$ of less than 50 nM and/or 12 nM against both human and mouse kallikrein.

In some embodiments, peptide or peptide mimetics are provided, comprising at least one loop formed between two cysteine residues. In some embodiments, peptide or peptide mimetics are provided wherein the at least one loop is 1, 2, 3, 4, 5, 6 or 7 amino acids in length. In some embodiments, peptide or peptide mimetics are provided comprising the consensus sequence Cys-($X_1X_2X_3$-)Cys-Arg-Val-R, wherein two cysteines are joined to each other by a bridging moiety to form a loop and —($X_1X_2X_3$—) represent a region of any independently natural or unnatural amino acids and wherein R represents zero, one or more amino acids. In some embodiments, peptide or peptide mimetic inhibitors of plasma kallikrein are provided, comprising a sequence of at least 6 contiguous amino acids of any of sequences recited herein and having at least one peptidic bond replacement, said at least one peptidic bond replacement being with a non-peptide moiety. In some embodiments, such peptide or peptide mimetic inhibitors are provided, wherein the non-peptide moiety is selected from the group consisting of thioamide, sulfonamide, sulfonate, phosphonamide, phosphonate phosphothioate, phosphinate, alkane, 1 or 2 hydroxyethylene, dihydroxylethylene, C—C single bond (alkane), C—C double bond (alkene), C—C triple bond (alkyne), C—O bond (methyleneoxy), O—N or N—O bond, (methyleneamino), triazole, hydrazide, urea, ketone, urethane bond, (di)haloalkene, methylenemercapto, methyleneamino, trifluoroethylamino, hydrazide and amideoxy.

DETAILED DESCRIPTION

The present invention relates to the discovery of novel peptides, specifically cyclic peptides and peptide mimetics which are useful in the diagnosis and/or treatment of disease in which the inhibition of plasma kallikrein is desirable.

As used herein, a "mimetic" refers to a molecule which exhibits some of the properties or features of another molecule. A "peptide mimetic" (also referred to as a peptidomimetic) is a mimetic in which the molecule contains non-peptidic structural elements that are capable of mimicking or antagonizing the biological action(s) of a natural peptide. A peptidomimetic may have many similarities to natural peptides, such as: amino acid side chains that are not found among the known 20 proteinogenic amino acids, non-peptide-based linkers used to effect cyclization between the ends or internal portions of the molecule, substitutions of the amide bond hydrogen moiety by methyl groups (N-methylation) or other alkyl groups, replacement of a peptide bond with a chemical group or bond that is resistant to chemical or enzymatic treatments, N- and C-terminal modifications, and conjugation with a non-peptidic extension (such as polyethylene glycol, lipids, carbohydrates, nucleosides, nucleotides, nucleoside bases, various small molecules, or phosphate or sulfate groups). As used herein, the term "cyclic peptide mimetic" or "cyclic polypeptide mimetic" refers to a peptide mimetic that has as part of its structure one or more cyclic features such as a loop, bridging moiety, and/or an internal linkage. As used herein, the term "bridging moiety" refers to one or more components of a bridge formed between two adjacent or non-adjacent amino acids in a polypeptide. The bridging moiety may be of any size or composition. In some embodiments, a bridging moiety comprises one or more chemical bonds between two adjacent or non-adjacent amino acids. In some embodiments, such chemical bonds may be between one or more functional groups on adjacent or non-adjacent amino acids. In some embodiments, the bridging moiety comprises one or more features including, but not limited to a disulfide bonds, thioether bonds and cyclic rings. In some embodiments, the bridging moiety comprises a disulfide bond formed between two cysteine residues. In some embodiments, the bridging moiety comprises one or more thioether bonds. In some embodiments, bridging moieties comprise non-protein or non-peptide based moieties, including, but not limited to cyclic rings [including, but not limited to aromatic ring structures (e.g. xylyls)]. Such bridging moieties may be introduced by reaction with reagents containing multiple reactive halides, including, but not limited to poly(bromomethyl)benzenes, poly(bromomethyl)pyridines, poly(bromomethyl)alkylbenzenes and/or (E)-1,4-dibromobut-2-ene. In some embodiments, bridging moieties of the present invention include, but are not limited to the following structures:

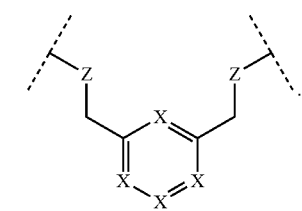

I

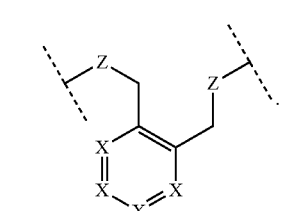

II

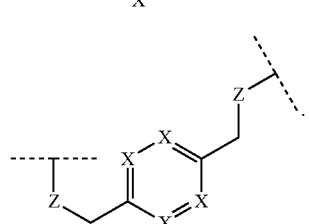

III

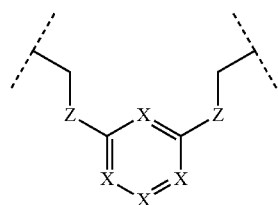

IV

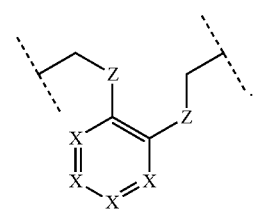

V

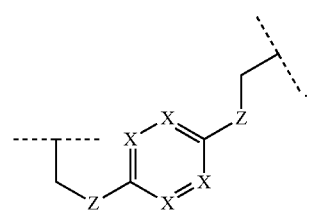

VI

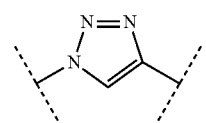

VII

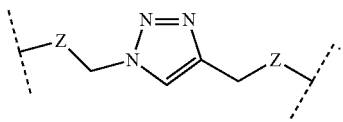

VIII

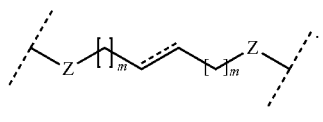

IX

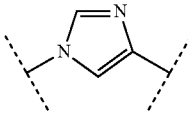

X

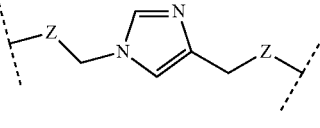

XI

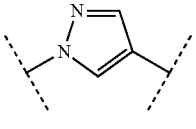

XII

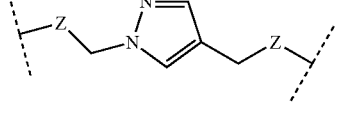

XIII

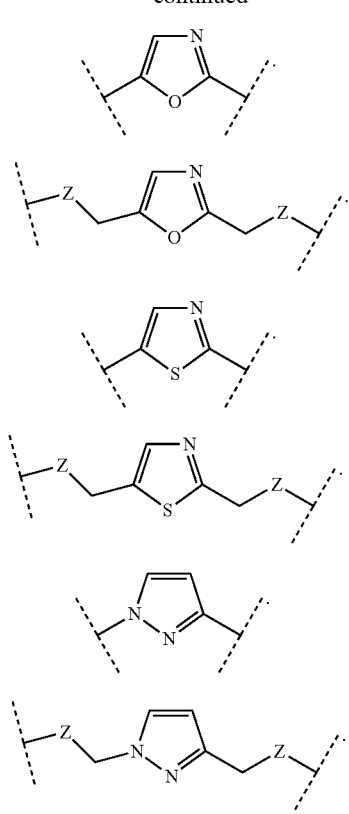

wherein each X is independently N or CH, such that no ring contains more than 2 N; each Z is independently a bond, NR, O, S, $CH_2$, C(O)NR, NRC(O), $S(O)_vNR$, $NRS(O)_v$; each m is independently selected from 0, 1, 2, and 3; each v is independently selected from 1 and 2; each R is independently selected from H and $C_1$-$C_6$; and each bridging moiety is connected to the peptide by independently selected $C_0$-$C_6$ spacers.

Unless otherwise defined, all technical and scientific terms used herein have the same meaning as commonly understood by one of ordinary skill in the art to which this invention belongs. Although methods and materials similar or equivalent to those described herein can be used in the practice or testing of the cyclic peptides and methods featured in the invention, suitable methods and materials are described below.

Peptides as Drugs

By virtue of their size and complexity, peptides are able to form numerous, highly specific contacts with their biological targets and can show a high level of selectivity for the correct or desired target as compared to a closely related target within the same family. In the case of plasma kallikrein, several serine proteases (such as, but not limited to, Factor XIa, Factor XIIa, plasmin and the like) show close similarity to plasma kallikrein and are often inhibited by the same small molecule inhibitors. Although a small molecule identified as a potent inhibitor of plasma kallikrein may inhibit Factor XIa less potently, the level of inhibition may be inadequate to prevent inactivation of Factor XIa, with undesirable effects on the normal blood coagulation cascade. Such "off-target effects" or "side effects" often cause highly effective drugs to fail regulatory approval due to safety concerns.

Numerous peptides have been developed into effective drugs. These include, but are not limited to, insulin, glucagon-like peptide 1 (GLP-1), somatostatin, vasopressin, cyclosporine A, and the like. In a case such as insulin, the therapeutic peptide can be identical to the naturally occurring molecule (i.e. that which circulates in humans and is considered "wild-type" in the human population). In many other cases, the peptide is not suitable or sub-optimal for therapeutic use due to a short circulating half-life that is often due to metabolic instability in the body. In these cases a modified or a variant form of the peptide (peptidomimetic) is used which results in improved pharmacokinetic and pharmacodynamic behavior. In other cases a peptide derived from a natural source has an equivalent mechanism of action but a preferred pharmaceutical profile and can be used as a therapy. For example, exenatide, a synthetic version of exedin-4, has biological properties similar to human glucagon-like peptide-1 (GLP-1) and has been approved by the FDA for the treatment of diabetes mellitus type 2. As another example, salmon calcitonin, calcitonin extracted from the Ultimobranchial glands of salmon, resembles human calcitonin but is more active than human calcitonin and may be used to treat postmenopausal osteoporosis, hypercalcaemia, paget's disease, bone metastases and phantom limb pain.

Peptides are typically limited to non-oral routes of administration. In nearly all cases, peptides and peptidomimetics must be delivered by injection, since even very short peptides (e.g., peptides with 4-10 amino acid residues) are incapable or poorly capable of passing through the cell membranes lining the intestinal tract. For efficient oral availability, drugs typically need to pass through both the luminal and basolateral membranes of gut epithelial cells in order to enter the systemic circulation. The poor membrane permeability and lack of oral bioavailability of peptides significantly limits their therapeutic use.

The effectiveness of a peptide as a drug may be influenced by it proteolytic stability. Within the body, peptides can be modified or degraded by enzymes, which can limit their effectiveness for interacting with an intended target. Maintaining a given level of a therapeutic peptide within the body or the bloodstream may be difficult due to efflux. The rate of efflux of a peptide from the body may vary and should be monitored when considering the administration of therapeutic peptides.

Metabolic stability of peptides is important as it is related to their global flexibility, intramolecular fluctuations, various internal dynamic processes as well as many biologic functions. The metabolic stability of peptides may be critical in the development of pharmaceuticals it may affect parameters such as, but not limited to, clearance, half-life and bioavailability of the drugs.

In general, the properties of natural peptides are generally not well suited for use as human therapeutics. Inhibitors of plasma kallikrein comprised exclusively of natural amino acids are unlikely to display the proteolytic and metabolic stability needed for use as human therapeutics. There remains a significant medical need for highly potent and highly specific plasma kallikrein inhibitors and formulations of plasma kallikrein inhibitors with properties consistent Discovery of Peptidomimetics Peptidomimetics may be identified by a variety of means. In some cases a naturally occurring peptide or a sequence found in a natural protein is used as a starting point. In these instances, the starting peptide sequence has been chosen because it is known to physically interact with a desired target molecule. A natural peptide may be chosen because it is an agonist or antagonist for a receptor, inhibits an enzyme, or modulates a channel. A sequence found in a natural protein may be chosen because it comprises a domain that participates in an interaction with another protein or some other molecule in a human or animal. In many cases, structural data on interacting proteins can be obtained from public databases (e.g. the RCSB Protein Data Bank; H. M. Berman, J. Westbrook, Z. Feng, G. Gilliland, T. N. Bhat, H. Weissig, I. N. Shindyalov, P. E. Bourne (2000) The Protein Data Bank Nucleic Acids Research, 28: 235-242) and the specific region of a protein that interacts with the desired target can be identified from crystallographic data on the protein complex. In other cases, peptides corresponding to various portions of a protein can be prepared and tested for binding to a target of interest. Once identified, chemical modifications are introduced to improve its stability and potency, with the resulting peptidomimetic having improved pharmacokinetic or pharmacodynamic parameters.

In other cases, a peptide is isolated by one of several methods for isolating peptide sequences from libraries of peptides based on their affinities to specific target proteins, nucleic acids, carbohydrates, lipids, or whole cells. Such methods include phage display, mRNA display, ribosome display, DNA display, DNA-encoded assembly, and two-hybrid screening, as well as their modifications (See, e.g., Takahashi, T. T et al. (2003). Trends in Biochem. Sci. 28(3):159-165; Kay, B. K. et al. (2001). Methods. 24:240-246; He, M and Taussig, M (2002). Briefins in Functional Genomics and Proteomics. 1(2): 204-212; Rothe, A. et al. (2006). The FASEB Journal. 20(10):1599-1610; all of which are included herein by reference in their entireties.)

Polypeptides can adopt three-dimensional structures that are capable of binding to other biological molecules with certain degrees of affinity and specificity. Some will bind with very high affinity and specificity. A library of random polypeptide sequences will be populated by molecules with a wide variety of three-dimensional structures. In order to isolate a polypeptide with a conformation that interacts with a specific target protein, individual sequences from the library can be prepared and tested or screened for their affinity to the target. However, for very large libraries ($>10^6$ members), the screening of individual sequences for binding affinity is not feasible. To overcome this limitation, a number of techniques have been developed to select novel polypeptides from extremely large, complex mixtures by virtue of their binding affinity to a target. Since high affinity binding polypeptides are predicted to be present at a very low frequency within the population, these selection methods rely on maintaining a physical link between the polypeptide and the genetic material (generally a nucleic acid such as DNA or RNA) encoding the polypeptide so that selection of the polypeptide automatically includes selection of a nucleic acid encoding it. The nucleic acid encoding the selected polypeptide can be amplified and sequenced to reveal the sequence of both the nucleic acid and the polypeptide. In one approach, phage display (see Cwirla, S. E. et al. (1990). Proc. Natl. Acad. Sci. U.S.A. 87:6378-6382; Dower, W. J. and Cwirla, S. E. U.S. Pat. Nos. 5,427,908 and 5,580,717), each random polypeptide member of the library is displayed on the surface of a bacteriophage particle as part of a fusion protein between the polypeptide and one of the phage coat proteins. The phage particle provides the link between the polypeptide and the encoding DNA by co-localizing them within the same physical entity, and the encoding DNA can be subsequently amplified by infecting bacteria with the selected phage. In another approach, ribosome display (see Kawasaki, G. H. U.S. Pat. Nos. 5,658,754 and 5,643,768), a mixture of messenger RNA (mRNA) molecules is translated in vitro in a manner that produces, for each mRNA in the mixture, a stabilized complex of ribosome, mRNA, and newly synthesized polypeptide protruding from the ribosome. Stabilizing the complex permits it to be held together while the polypeptides are screened for binding to a target of interest. The mRNAs encoding the selected polypeptides can be amplified using polymerase chain reaction (PCR), and then characterized, e.g., by sequencing.

In yet another approach, mRNA display (see Szostak, J. W. and Roberts, R. W., U.S. Pat. No. 6,258,558, the contents of which are incorporated herein by reference in its entirety), each mRNA molecule in the library is modified by the covalent addition of a puromycin-like moiety at its 3' terminus. The puromycin-like moiety is an aminoacyl-tRNA acceptor stem analog that functions as a peptidyl acceptor, and can be added to a growing polypeptide chain by the peptidyl transferase activity of a ribosome translating the mRNA. During in vitro translation, the mRNA and the encoded polypeptide become covalently linked through the puromycin-like moiety, creating an RNA-polypeptide fusion. After selecting a fusion molecule by binding of its polypeptide component to a target, the RNA component of the selected fusion molecule can be amplified using PCR, and then characterized. Several other methods have been developed to produce a physical linkage between a polypeptide and its encoding nucleic acid to facilitate selection and amplification (see Yanagawa, H., Nemoto, N., Miyamoto, E., and Husimi, Y., U.S. Pat. No. 6,361,943; Nemoto, H., Miyamoto-Sato, E., Husimi, H., and Yanagawa, H. (1997). FEBS Lett. 414:405-408; Gold, L., Tuerk, C., Pribnow, D., and Smith, J. D., U.S. Pat. Nos. 5,843,701 and 6,194,550; Williams, R. B., U.S. Pat. No. 6,962,781; Baskerville, S. and Bartel, D. P. (2002). Proc. Natl. Acad. Sci. USA 99:9154-9159; Baskerville, D. S. and Bartel, D. P., U.S. Pat. No. 6,716,973; Sergeeva, A. et al. (2006). Adv. Drug Deliv. Rev. 58:1622-1654; the contents of each of which are incorporated herein by reference in their entirety).

mRNA display is a particularly useful method for creating large libraries of peptides. Accordingly, provided herein are methods of selecting for a polypeptide (or an mRNA encoding a polypeptide) that interacts with plasma kallikrein. A library will generally contain at least $10^2$ members, more preferably at least $10^6$ members, and more preferably at least $10^9$ members (e.g., any of the mRNA-polypeptide complexes). In some embodiments, the library will include at least $10^{12}$ members or at least $10^{14}$ members. In general, the members will differ from each other; however, it is expected there will be some degree of redundancy in any library. The library can exist as a single mixture of all members, or can be divided into several pools held in separate containers or wells, each containing a subset of the library, or the library can be a collection of containers or wells on a plate, each container or well containing just one or a few members of the library.

Each mRNA in the library preferably comprises a translation initiation sequence, a start codon, and a variable polypeptide (e.g., protein or short peptide) coding region that is generated by, for example, a random or semi-random assembly of nucleotides, and varies from mRNA to mRNA in the library (though there will likely be some degree of redundancy within the library). The translation initiation sequence, start codon, and variable polypeptide coding region can be flanked by known, fixed sequences that can be used for PCR amplification of the mRNA, e.g., after selection. Other fixed sequences that can be present include those corresponding to sequences that encode amino acids that can participate in chemical or enzymatic cross-linking reactions, such that the polypeptide produced can be modified or derivatized after translation, or that encode a fixed C-terminal extension such as a polypeptide tag that can facilitate purification of the peptide-mRNA fusions.

Once a library of mRNA derivatized with puromycin is generated, the library can be translated. The resulting polypeptides (e.g., displayed polypeptides) will be linked to their corresponding mRNAs as described herein (e.g., as an mRNA-polypeptide complex).

Numerous in vitro translation systems have been described in the literature. The most common systems utilize rabbit reticulocyte lysates, wheat germ extracts, or E. coli extracts, which are available from a number of commercial sources in kit form (e.g., Ambion, Austin, Tex.; Promega, Madison, Wis.; Novagen/EMD Chemicals, Gibbstown, N.J.; Qiagen, Valencia, Calif.).

Unlike phage display or other systems that rely on translation within cells, mRNA display is readily adapted to directly produce libraries of peptidomimetics rather than peptides by performing in vitro translation with unnatural or non-standard amino acids. The 20 natural proteinogenic amino acids are identified by either the one-letter or three-letter designations as follows: aspartic acid (Asp:D), isoleucine threonine (Thr:T), leucine (Leu:L), serine (Ser:S), tyrosine (Tyr:Y), glutamic acid (Glu:E), phenylalanine (Phe:F), proline (Pro:P), histidine (His:H), glycine (Gly:G), lysine (Lys:K), alanine (Ala:A), arginine (Arg:R), cysteine (Cys:C), tryptophan (Trp:W), valine (Val:V), glutamine (Gln:Q) methionine (Met:M), asparagine (Asn:N). Naturally occurring amino acids include only their levorotary (L) stereoisomeric forms.

Unnatural amino acids have side chains or other structures not present in the 20 naturally-occurring amino acids listed above and include, but are not limited to: N-methyl amino acids, N-alkyl amino acids, alpha, alpha substituted amino acids, beta-amino acids, alpha-hydroxy amino acids, D-amino acids, and other unnatural amino acids known in the art (See, e.g., Josephson et al., (2005) J. Am. Chem. Soc. 127: 11727-11735; Forster, A. C. et al. (2003) Proc. Natl. Acad. Sci. USA 100: 6353-6357; Subtelny et al., (2008) J. Am. Chem. Soc. 130: 6131-6136; Hartman, M. C. T. et al. (2007) PLoS ONE 2:e972; and Hartman et al., (2006) Proc. Natl. Acad. Sci. USA 103:4356-4361).

Essentially any amino acid that, when attached to an appropriate tRNA, can be assembled into a polymer by natural or mutant ribosomes can be used (see Sando, S. et al., (2007) J. Am. Chem. Soc. 129:6180-6186; Dedkova, L. et al. (2003) J. Am. Chem. Soc. 125: 6616-6617; Josephson, K., Hartman, M. C. T., and Szostak, J. W. (2005) J. Am. Chem. Soc. 127:11727-11735; Forster, A. C. et al. (2003) Proc. Natl. Acad. Sci. USA 100:6353-6357; Subtelny, A. O., Hartman, M. C. T., and Szostak, J. W. (2008) J. Am. Chem. Soc. 130:6131-6136; and Hartman, M. C. T. et al. (2007) PLoS ONE 2:e972).

When unnatural amino acids are desired, it may be advantageous to use a purified translation system that lacks endogenous aminoacylated tRNAs (Shimizu, Y. et al. (2001) Nat. Biotech. 19:751-755; Josephson, K., Hartman, M. C. T., and Szostak, J. W. (2005) J. Am. Chem. Soc. 127: 11727-11735; Forster, A. C. et al. (2003) Proc. Natl. Acad. Sci. USA 100: 6353-6357). If unnatural amino acids are used with an in vitro translation system based on a lysate or extract, it may be desirable to deplete the extract of endogenous tRNAs, as previously described (see Jackson, R. J., Napthine, S., and Brierley, I. (2001) RNA 7:765-773). A system based on purified E. coli translation factors is commercially available (PURExpress™; New England Biolabs, Ipswich, Mass.). These systems are particularly useful for translation with unnatural amino acids to produce peptidomimetics.

When using natural amino acids with an in vitro translation system based on a lysate or extract, translation is dependent on the enzymatic charging of amino acids onto tRNAs by tRNA synthetases, all of which are components of the extracts. Alternatively, in vitro translation systems that use purified translation factors and ribosomes, or tRNA-depleted extracts, require that aminoacylated tRNAs be provided. In these instances, purified or in vitro synthesized tRNAs can be charged with amino acids using chemical (see Frankel, A., Millward, S. W., and Roberts, R. W. (2003) Chem. Biol. 10:1043-1050) or enzymatic procedures (Josephson, K., Hartman, M. C. T., and Szostak, J. W. (2005) J. Am. Chem. Soc. 127: 11727-11735; Murakami, H. et al. (2006) Nat. Methods 3:357-359).

Numerous publications describe the recovery of mRNA-displayed polypeptides from translation complexes, and these are suitable for use with the methods described herein (Liu, R. et al. (2000). Methods Enzymol. 318:268-293; Baggio, R. et al. (2002). J. Mol. Recognit. 15:126-134; U.S. Pat. No. 6,261,804). The recovery of mRNA-displayed polypeptides may be facilitated by the use of various "tags" that are included in the polypeptide by translation of fixed sequences of the polypeptide coding sequence and which bind to specific substrates or molecules. Numerous reagents for capturing such tags are commercially available, including reagents for capturing the His-tag, FLAG-tag, glutathione-S-transferase (GST) tag, strep-tag, HSV-tag, T7-tag, S-tag, DsbA-tag, DsbC-tag, Nus-tag, myc-tag, hemagglutinin (HA)-tag, or Trx-tag (Novagen, Gibbstown, N.J.; Pierce, Rockford, Ill.). mRNA-displayed peptides can also be isolated by binding of a polyA tail on the mRNA to polydT resin, or a combination of a polyA tail and a His-tag.

After the in vitro translation reaction has been performed, and prior to the selection step, the mRNA portion of the functionalized RNA is typically reversed-transcribed to produce a RNA-DNA hybrid molecule (e.g., a cDNA). This serves to protect the RNA from degradation, and also prevents the RNA from folding into a secondary structure that could bind to the selection target, which would lead to selection of inappropriate products (e.g., the selection of RNA aptamers rather than polypeptide aptamers).

After in vitro translation and isolation of peptide-mRNA fusions, the peptide moiety may be modified by intramolecular or intermolecular cross-linking, chemical conjugation, enzymatic cleavage, truncation, or extension with additional amino acid monomers. One way to accomplish this is by incorporating unnatural amino acids with reactive side chains into the polypeptides that make up the library. After translation, the newly formed polypeptides can be reacted with molecules that react specifically with the reactive side chain of the incorporated amino acid. For example, an amino acid with a terminal alkyne side chain can be incorporated into the polypeptide library and subsequently reacted with an azido sugar, creating a library of displayed polypeptides with sugars attached at the positions of the alkynyl side chains (Josephson, K., Hartman, M. C. T., and Szostak, J. W. (2005) J. Am. Chem. Soc. 127: 11727-11735). A variety of reactive side chains can be used for such post-translational conjugation, including amines, carboxyl groups, azides, terminal alkynes, alkenes, and thiols.

One particularly useful modification is based on the cross-linking of amino acids to produce cyclic structures. Cyclic regions in a protein contain a rigid domain, which reduces conformational flexibility and degrees of rotational freedom, leading to very high affinity binding to target proteins. A number of methods for cyclizing a polypeptide are available to those skilled in the art and are incorporated herein by reference. Typically, the chemical reactivity of specific amino acid side chains and/or the carboxyl or amino termini of the polypeptide are exploited to crosslink two sites of the polypeptide to produce a cyclic molecule. In one method, the thiol groups of two cysteine residues are cross-linked by reaction with dibromoxylene (see Timmerman, P. et al., (2005) ChemBioChem 6:821-824). Tri- and tetrabromoxylene can be used to produce polypeptides with two and three loops, respectively.

In another exemplary method, a side chain amino group and a terminal amino group are cross-linked with disuccinimidyl glutarate (see Millward, S. W. et al., J. Am. Chem. Soc. 127:14142-14143, 2005). In other approaches, cyclization is accomplished by making a thioether bridging group between two sites on the polypeptide (see Timmerman, P. et al., (2005) ChemBioChem 6:821-824; incorporated by reference herein in its entirety). One chemical method relies on the incorporation of an N-chloroacetyl modified amino acid at the N-terminus of the polypeptide, followed by spontaneous reaction with the thiol side chain of an internal cysteine residue (see Goto, Y. et al. (2008) ACS Chem. Biol. 3:120-129). An enzymatic method relies on the reaction between (1) a cysteine and (2) a dehydroalanine or dehydrobutyrine group, catalyzed by a lantibiotic synthetase, to create the thioether bridging group (see Levengood, M. R. and Van der Donk, W. A., Bioorg. and Med. Chem. Lett. 18:3025-3028, 2008). The dehydro functional group can also be generated chemically by the oxidation of selenium containing amino acid side chains incorporated during translation (see Seebeck, F. P. and Szostak, J. W. J. Am. Chem. Soc. 2006).

A library of mRNA-polypeptide fusions (also referred to herein as an mRNA display library) generated using the methods described above, and which may or not have been subjected to a post-translational modification (such as cyclization of the polypeptide, as described above), can be subjected to a batch selection step to isolate those complexes displaying desirable polypeptides. When plasma kallikrein is used, in the selection step it is typically isolated by purification from a natural biological source or from a recombinant DNA expression system. If desirable, plasma kallikrein isolated from either source may be first activated by treated with Factor XIIa.

Typically, the activated plasma kallikrein is conjugated to a solid substrate, such as an agarose or synthetic polymer bead. Numerous methods are available for immobilizing plasma kallikrein to a solid support. In one particularly useful method, plasma kallikrein is conjugated to biotin and streptavidin beads are used to immobilize the enzyme. The beads comprising the immobilized plasma kallikrein are mixed with the mRNA display library and incubated under conditions (e.g., temperature, ionic strength, divalent cations, and competing binding molecules) that permit specific members of the library to bind the target. Alternatively, the enzyme can be free in solution and, after binding to an appropriate polypeptide, the mRNA-polypeptide fusions bound to plasma kallikrein are captured by appropriately modified beads.

The binding conditions can be varied in order to change the stringency of the selection. For example, low concentrations of a competitive binding agent can be added to ensure that the selected polypeptides have a relatively higher affinity. Alternatively, the incubation period can be chosen to be very brief, such that only polypeptides with high $k_{on}$ rates will be isolated. In this manner, the incubation conditions play an important role in determining the properties of the selected polypeptides. Negative selections can also be employed. In this case, a selection to remove polypeptides with affinity to the substrate to which the target is bound (e.g., Sepharose) is carried out by applying the displayed library to substrate beads lacking the target protein. This step can remove mRNAs and their encoded polypeptides that are not specific for the target protein. Numerous references describing how to conduct selection experiments are available. (See, e.g., U.S. Pat. No. 6,258,558, incorporated herein by reference in its entirety; Smith, G. P. and Petrenko, V. A., (1997) Chem. Rev. 97:391-410; Keefe, A. D. and Szostak, J. W. (2001) Nature 15:715-718; Baggio, R. et al. (2002) J. Mol. Recog. 15:126-134; Sergeeva, A. et al. (2006) Adv. Drug Deliv. Rev. 58:1622-1654).

The frequency at which binding molecules are present in a library of random sequences is expected to be very low. Thus, in the initial selection step, very few polypeptides meeting the selection criteria (and their associated mRNAs) should be recovered. Typically, the selection is repeated with mRNAs selected from the first round of selection. This is accomplished by using PCR to amplify the mRNAs or corresponding cDNAs selected in the first round, followed by in vitro transcription to produce a new library of mRNAs. PCR primers corresponding to the 5' and 3' ends of the mRNAs in the library are used. Typically, the 5' primer will extend in the 5' direction beyond the end of the mRNA so that a bacterial promoter, such as a T7 promoter, is added to the 5' end of each amplified molecule. Once amplified, the double-stranded DNA can be used in an in vitro transcription reaction to generate the mRNA for a subsequent round of selection.

The selection process typically involves a number of rounds or cycles, in which the pool of selected molecules is incrementally enriched in a specific set of sequences at the end of each round. The selection conditions may be the same for each round, or the conditions may change, for example, in order to increase the stringency of selection in later rounds. The progress of selection may be monitored by the use of isotopically-labeled amino acids, such as $^{35}$S methionine. The amount of radiolabeled polypeptide bound to the target at each round is measured, and a progressive increase in recovered radiolabel is indicative of a progressive enrichment in RNA molecules encoding polypeptides with binding affinity to the target. After any round, the PCR products may be cloned and sequenced. Generally, cloning and sequencing is performed after a round in which appreciable (e.g. >2% over background to beads lacking immobilized plasma kallikrein) amounts of radiolabeled polypeptide are recovered in the target-bound pool. Sequences that are found in multiple isolates are candidates for encoding polypeptides that bind specifically to the target. Alternatively, high throughput sequencing of thousands of clones can be performed after the first or subsequent rounds. Sequences that increase in frequency between the third and fourth rounds are candidates for encoding polypeptides that bind specifically to the target. The polypeptide encoded by any sequence may be translated or synthesized and tested for binding affinity to the original target protein used in the selection.

The libraries and methods of the present invention may be used to optimize the function or properties of a polypeptide. In one approach, mutagenic PCR (Keefe, A. D. and Szostak, J. W. (2001). Nature 15:715-718) is used to introduce sequence variation in the library once the population is enriched in polypeptides with a certain level of binding affinity. Alternatively, a single RNA sequence encoding a polypeptide with defined binding properties can be replicated but with a defined level of mutations, or mutagenic PCR can be performed to produce a pool of mutant molecules. Upon in vitro translation the resulting mixture of mRNA molecules produced from such a pool is expected to encode polypeptides with a range of improved, similar, or reduced affinities as compared to the starting sequence, and a selection performed on mRNAs from such a pool may be expected to identify polypeptides with improved affinity if an appropriate stringency regimen is used during the selection.

In a second approach, optimization is performed in a directed manner. A sequence encoding a polypeptide with established binding or functional properties is subjected to site-directed mutagenesis, whereby a series of sequences is produced, with each sequence having one codon replaced with, for example, an alanine codon. The number of sequences in the set is equal to the number of amino acid residues that are to be mutated. After in vitro translation, the polypeptide product of each "alanine scanning" mutant is tested for binding or functional properties. Sites at which an alanine substitution affects the binding or function of the polypeptide are considered critical residues. Similarly, an N-methyl scan may be performed, such that each residue is replaced with the N-methyl derivative, and positions in the peptide backbone that can tolerate N-methyl substitutions can be identified.

Alternatively, the sequences can be pooled, subjected to one or more rounds of a high stringency selection, and a pool of sequences representing high affinity binding polypeptides is isolated. Critical residues are identified after DNA sequencing of the recovered DNA as those that cannot be substituted by an alanine residue without loss of activity. Once the critical residues are identified, a pool of mRNA molecules encoding a wide variety of natural (or unnatural) amino acids at each critical position is produced. The resulting pool is subjected to one or more rounds of a high stringency selection (with the appropriate mixture of tRNAs charged with natural or unnatural amino acids), and sequences representing high affinity binding polypeptides are isolated after in vitro translation. In this manner, an optimal polypeptide can be identified. Since the optimal sequence may not necessarily be identified by combining optimal residues at individual sites, it is useful to test mutations at multiple sites in combination.

Both alanine and N-methyl scanning can also be performed using chemical synthesis approaches, such as solid phase peptide synthesis (see e.g., Coin, I et al. (2007). Nature Protocols 2(12):3247-56), for producing peptides.

Once a pool, population or subset of peptides is identified, they may be evaluated for therapeutic or diagnostic applications, including improved pharmacokinetic and/or pharmacodynamic properties.

In one embodiment, peptides are evaluated for one or more of target binding affinity, activity in biochemical or cell based assays, protease resistance, in vitro or in vivo permeability, presence of drug like properties such as plasma protein binding, metabolism (in microsomes, hepatocytes, or plasma), and PGP/CYP inhibition. Peptides of the present invention may also undergo testing for oral bioavailability, toxicity, hERG activity, circulating half-life, other pharmacokinetic and pharmacodynamic parameters, and efficacy in animal models of disease.

Cyclic Peptides and Cyclic Peptidomimetics of the Invention

According to the present invention, once a single peptide or a pool of candidate peptide molecules is identified, they may undergo one or more rounds of structure activity relationship (SAR) optimization using standard chemical and peptide synthesis techniques. Such optimization may include considerations such as avoiding charged polar side chains (Asp, Glu, Arg, Lys) that may inhibit cell penetration, avoidance of side chains that pose metabolic liabilities (Tyr, Met, Trp, Cys), improving solubility, avoidance of unnecessary molecular weight, avoidance of rotatable bonds, and lipophilicity.

In one embodiment, it is a goal of the present invention to provide cyclic peptide mimetics designed to be metabolically stable and cell permeable.

As used herein, the term "amino acid" includes the residues of the natural amino acids as well as unnatural amino acids. The term also includes amino acids bearing a conventional amino protecting group (e.g. acetyl or benzyloxycarbonyl), as well as natural and unnatural amino acids protected at the carboxy terminus (e.g., as a ($C_1$-$C_6$) alkyl, phenyl or benzyl ester or amide; or as an alpha-methylbenzyl amide). Other suitable amino and carboxy protecting groups are known to those skilled in the art (See for example, Greene, T. W.; Wutz, P. G. M., Protecting Groups In Organic Synthesis; second edition, 1991, New York, John Wiley & sons, Inc, and documents cited therein). The peptide compositions of the present invention may also include modified amino acids.

Unnatural amino acids useful for the optimization of kallikrein inhibiting peptides include, but are not limited to, homolysine, homoarginine, homoserine, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimeiic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylpentylglycine, naphthylalanine, ornithine, pentylglycine, thioproline, norvaline, tert-butylglycine, phenylglycine, 7-azatryptophan, 4-fluorophenylalanine, penicillamine, sarcosine, homocysteine, 1-aminocyclopropanecarboxylic acid, 1-aminocyclobutanecarboxylic acid, 1-aminocyclopentanecarboxylic acid, 1-aminocyclohexanecarboxylic acid, 4-aminotetrahydro-2H-pyran-4-carboxylic acid, aminoisobuteric acid, (S)-2-amino-3-(1H-tetrazol-5-yl)propanoic acid, cyclopentylglycine, cyclohexylglycine, cyclopropylglycine, η-ω-methyl-arginine, 4-chlorophenylalanine, 3-chlorotyrosine, 3-fluorotyrosine, 5-fluorotryptophan, 5-chlorotryptophan, citrulline, 4-chloro-homophenylalanine, homophenylalanine, 4-aminomethyl-phenylalanine, 3-aminomethyl-phenylalanine, octylglycine, norleucine, tranexamic acid, 2-amino pentanoic acid, 2-amino hexanoic acid, 2-amino heptanoic acid, 2-amino octanoic acid, 2-amino nonanoic acid, 2-amino decanoic acid, 2-amino undecanoic acid, 2-amino dodecanoic acid, aminovaleric acid, and 2-(2-aminoethoxy)acetic acid, pipecolic acid, 2-carboxy azetidine, hexafluoroleucine, 3-Fluorovaline, 2-amino-4,4-difluoro-3-methylbutanoic acid, 3-fluoro-isoleucine, 4-fluoroisoleucine, 5-fluoroisoleucine, 4-methylphenylglycine, 4-ethyl-phenylglycine, isopropyl-phenylglycine, (S)-2-amino-5-(3-methylguanidino)pentanoic acid, (S)-2-amino-3-(4-(aminomethyl)phenyl)propanoic acid, (S)-2-amino-3-(3-(aminomethyl)phenyl)propanoic acid, (S)-2-amino-4-(2-aminobenzo[d]oxazol-5-yl)butanoic acid, (S)-leucinol, (S)-valinol, (S)-tert-leucinol, (R)-3-methylbutan-2-amine, (S)-2-methyl-1-phenylpropan-1-amine, and (S)—N,2-dimethyl-1-(pyridin-2-yl)propan-1-amine, (S)-2-amino-3-(oxazol-2-yl)propanoic acid, (S)-2-amino-3-(oxazol-5-yl)propanoic acid, (S)-2-amino-3-(1,3,4-oxadiazol-2-yl)propanoic acid, (S)-2-amino-3-(1,2,4-oxadiazol-3-yl) propanoic acid, (S)-2-amino-3-(5-fluoro-1H-indazol-3-yl)

propanoic acid, and (S)-2-amino-3-(1H-indazol-3-yl) propanoic acid and the D and L stereoisomers thereof.

Modified amino acid residues useful for the optimization of kallikrein inhibiting peptides include, but are not limited to those which are chemically blocked, reversibly or irreversibly, or chemically modified on their N-terminal amino group or their side chain groups, as for example, N-methylated D and L natural or unnatural amino acids or residues wherein the side chain functional groups are chemically modified to another functional group. For example, modified amino acids include without limitation, methionine sulfoxide; methionine sulfone; aspartic acid-(beta-methyl ester), a modified amino acid of aspartic acid; N-ethylglycine, a modified amino acid of glycine; or alanine carboxamide, and a modified amino acid of alanine. Unnatural amino acids may be purchased from Sigma Aldrich or other supplier. Unnatural amino acids may further include any of those listed in Table 2 of US patent publication US 2011/0172126, the contents of which are incorporated herein by reference in their entirety.

The amino acid sequences of the peptides of the invention may comprise only naturally occurring amino acids and as such may be considered to be peptides, polypeptides, or fragments thereof. Alternatively, the peptides may comprise both naturally and non-naturally occurring or modified amino acids or be exclusively comprised of non-naturally occurring amino acids. According to the present invention, the compositions identified may be "peptide mimetics," "peptidomimetics," "peptides," "polypeptides," or "proteins." While it is known in the art that these terms imply relative size, these terms as used herein should not be considered limiting with respect to the size of the various polypeptide based molecules referred to herein and which are encompassed within this invention, unless otherwise noted.

According to the present invention, any amino acid based molecule may be termed a "polypeptide" and this term embraces both "peptides" and "proteins." Peptides are also a category of proteins and are traditionally considered to range in size from about 4 to about 50 amino acids. Dipeptides, those having two amino acid residues are a category of peptide as are tripeptides (3 amino acids). Polypeptides larger than about 50 amino acids are generally termed "proteins." Peptide, polypeptide and/or proteins sequences may be linear or cyclic. For example, a cyclic peptide can be prepared or may result from the formation of disulfide bridges between two cysteine residues in a sequence. A peptide can be linked through the carboxy terminus, the amino terminus, or through any other convenient point of attachment, such as, for example, through the sulfur of a cysteine or any side-chain of an amino acid residue or other linkage including, but not limited to, a maleimide linkage, an amide linkage, an ester linkage, an ether linkage, a thiol ether linkage, a hydrazone linkage, or an acetamide linkage.

The term "amino acid sequence variant" refers to molecules with some differences in their amino acid sequences as compared to a native sequence. The amino acid sequence variants may possess substitutions, deletions, and/or insertions at certain positions within the amino acid sequence. Ordinarily, variants will possess at least about 70% homology to a native or starting sequence, and preferably, they will be at least about 80%, more preferably at least about 90% homologous to a native or starting sequence.

"Homology" as it applies to amino acid sequences is defined as the percentage of residues in the candidate amino acid sequence that are identical with the residues in the amino acid sequence of a second sequence after aligning the sequences and introducing gaps, if necessary, to achieve the maximum percent homology. Methods and computer programs for the alignment are well known in the art. It is understood that homology depends on a calculation of percent identity but may differ in value due to gaps and penalties introduced in the calculation.

By "homologs" as it applies to amino acid sequences is meant the corresponding sequence of other species having substantial identity to a second sequence of a second species.

"Analogs" is meant to include polypeptide variants which differ by one or more amino acid alterations, e.g., substitutions, additions or deletions of amino acid residues that still maintain one or more of the properties of the parent or starting polypeptide.

The present invention contemplates several types of composition that are amino acid based including variants and derivatives. These include substitutional, insertional, deletion and covalent variants and derivatives. The term "derivative" is used synonymously with the term "variant" and refers to a molecule that has been modified or changed in any way relative to a reference molecule or starting molecule.

As such, included within the scope of this invention are polypeptide based molecules containing substitutions, insertions and/or additions, deletions and covalently modifications. For example, sequence tags or amino acids, such as one or more lysines, can be added to the peptide sequences of the invention (e.g., at the N-terminal or C-terminal ends). Sequence tags can be used for peptide purification or localization. Lysines can be used to increase peptide solubility or to allow for site specific modifications, such as, but not limited to, biotinylation or PEGylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence, which is soluble, or linked to a solid support.

"Substitutional variants" when referring to polypeptides are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Isosteres" are one of two or more molecules that exhibit some similarity of biological properties as a result of having the same number of total or valence electrons in the same arrangement and that consist of different atoms, not necessarily the same number of atoms. There are two classes of isosteres, classical and non-classical. Classical isosteres have the same number of atoms and/or the same number of valence electrons whereas non-classical isosteres are molecules that produce a similar biological effect in vivo but do not have the same number of atom and/or valence electrons.

According to the present invention, "peptide isosteres" are defined as isosteres having properties resembling peptides. Peptide isosteres may be of a linear type comprising at least one peptide bond replacement or may be cyclic and comprise an amine and a carboxylic acid function. Such replacement may be with any moiety which improves the physicochemical, structural or functional properties of the molecule. Replacement of the peptide bond may increase the metabolic stability of the peptides and reduce the flexibility. Peptide isosteres described herein may be mono-, di-, tri-, tetra-, penta-, sexta-, septa-, octa- nona- deca-peptide isosteres, meaning that at least 1, 2, 3, 4, 5, 6, 7, 8, 9 or 10 peptidic bonds may be replaced. Non-limiting examples of linear dipeptide isosteres for amide (peptidic) bonds include thioamide, sulfonamide, sulfonate, phosphonamide, phosphonate phosphothioate, phosphinate, alkane, 1 or 2 hydroxyethylene, dihydroxyethylene, C—C single bond (alkane), C═C double bond (alkene), C—C triple bond (alkyne), C—O bond (methyleneoxy), O—N or N—O bond, (methyleneamino), triazole, hydrazide, urea, ketone, urethane bond, (di)haloalkene, methylenemercapto, methyleneamino, trifluoroethylamino, hydrazide, amideoxy, and others known to those of skill in the art.

Peptide isosteres may also be cyclic molecules that are decorated with an amine and a carboxylic acid function. Non-limiting examples of cyclic peptide isosteres with varying ring sizes include carbacycles, azacycles and oxacycles. Azacycles may be based on an alkaloid core which forms a bicyclic structure isostere. An example of an azacyclic isostere includes an isostere based on a triazole ring formed by a copper catalyzed azide-alkyne cycloaddition. Cyclic peptide isosteres described herein may be bi-, tri-, tetra-, penta- sexta-, septa-, octa- nona- deca-peptide cyclic isosteres "Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid.

"Deletional variants" when referring to polypeptides are those with one or more amino acids in the native or starting amino acid sequence removed. Ordinarily, deletional variants will have one or more amino acids deleted in a particular region of the molecule.

"Features" when referring to polypeptides are defined as distinct amino acid sequence-based components of a molecule. Features of the polypeptide of the present invention include surface manifestations, local conformational shape, folds, loops, half-loops, domains, half-domains, sites, termini or any combination thereof.

As used herein when referring to polypeptides the terms "site" as it pertains to amino acid based embodiments is used synonymously with "amino acid residue" and "amino acid side chain." A site represents a position within a peptide or polypeptide that may be modified, manipulated, altered, derivatized or varied within the polypeptide based molecules of the present invention.

According to the present invention, the polypeptides may comprise a consensus sequence, which is discovered through rounds of selection. As used herein, a "consensus" sequence is a single sequence which represents a collective population of sequences allowing for variability at one or more sites.

Inhibitor Compounds Obtained by Alternate Cyclization Procedures

Plasma kallikrein inhibitors may be synthesized according to one or more of the chemical reactions described in sections A, B and C of this section.

A. Heck Reaction

As used herein, the term "Heck reaction" refers to a chemical reaction wherein an unsaturated halide (including, but not limited to a bromide) reacts with an alkene group as well as a base in the presence of a catalyst comprising palladium resulting in the formation of a substituted alkene (Mizoroki, T. et al., Arylation of olefin with aryl iodide catalyzed by palladium. Bulletin of the Chemical Society of Japan. 1971. 44(2):p 581). For peptide mimetic synthesis by Heck reaction, peptide containing resin may be treated with a reaction buffer which may comprise DMF/H$_2$O/Et$_3$N, Pd(OAc)$_2$, PPh$_3$, (nBu)$_4$NCl in one portion. The resulting suspension may be agitated overnight at 37° C. After this time, the resin may be washed. Such washing may be done sequentially with DMF, MeOH, DCM and dried under a nitrogen gas flow. Resulting peptides may be cleaved off from the resin with TFA/H$_2$O(97:3) and purified by methods known in the art (including, but not limited to reverse phase HPLC). An example of one such reaction is presented in Scheme 1.

Scheme 1

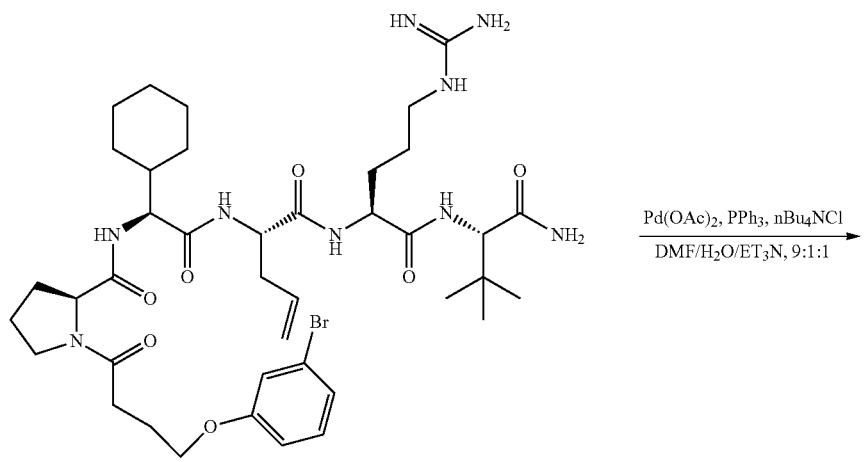

-continued

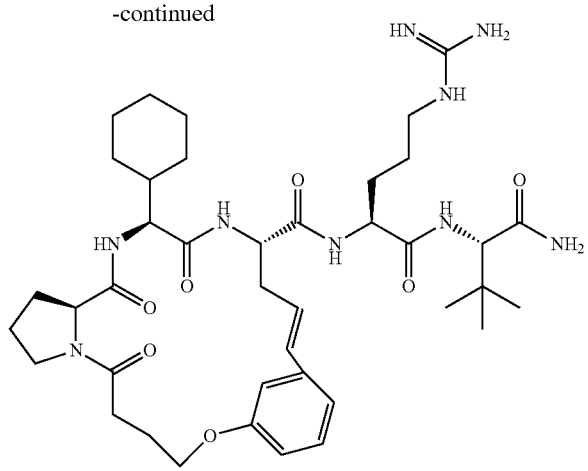

In some embodiments, the double bond formed in the reaction is in the S stereochemical formation. In some embodiments, the double bond formed in the reaction is in the R stereochemical formation.

B. Buchwald Reaction

As used herein, the term "Buchwald reaction" refers to a chemical reaction carried out overnight at a temperature selected from any between 50° C. and 150° C. wherein a halide (including, but not limited to a bromide) is reacted with a chemical group comprising oxygen in the presence of toluene and a catalyst comprising palladium. An example of one such reaction is presented in Scheme 2.

Scheme 2

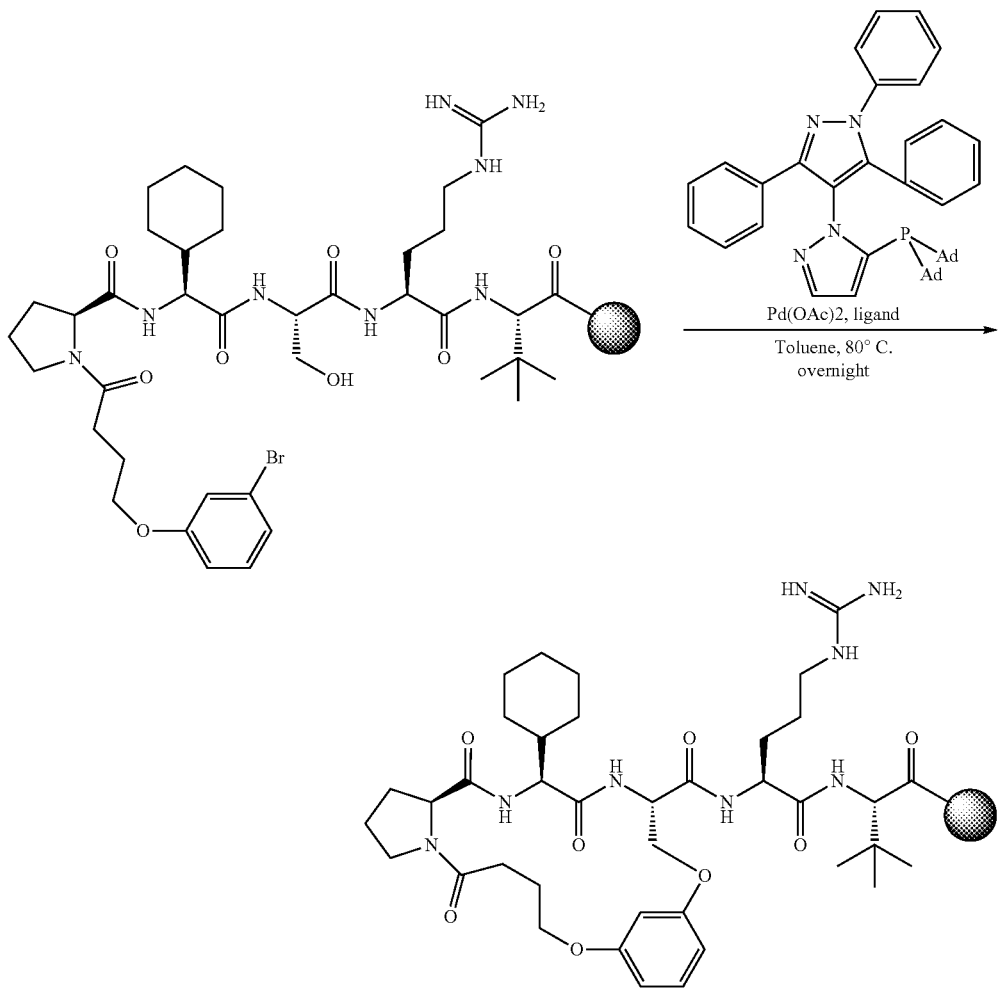

C. Olefin Metathesis

As used herein, the term "olefin metathesis" refers to a chemical reaction comprising alkene redistribution through the breaking and reforming of carbon-carbon double bonds. An example of one such reaction is presented in Scheme 3.

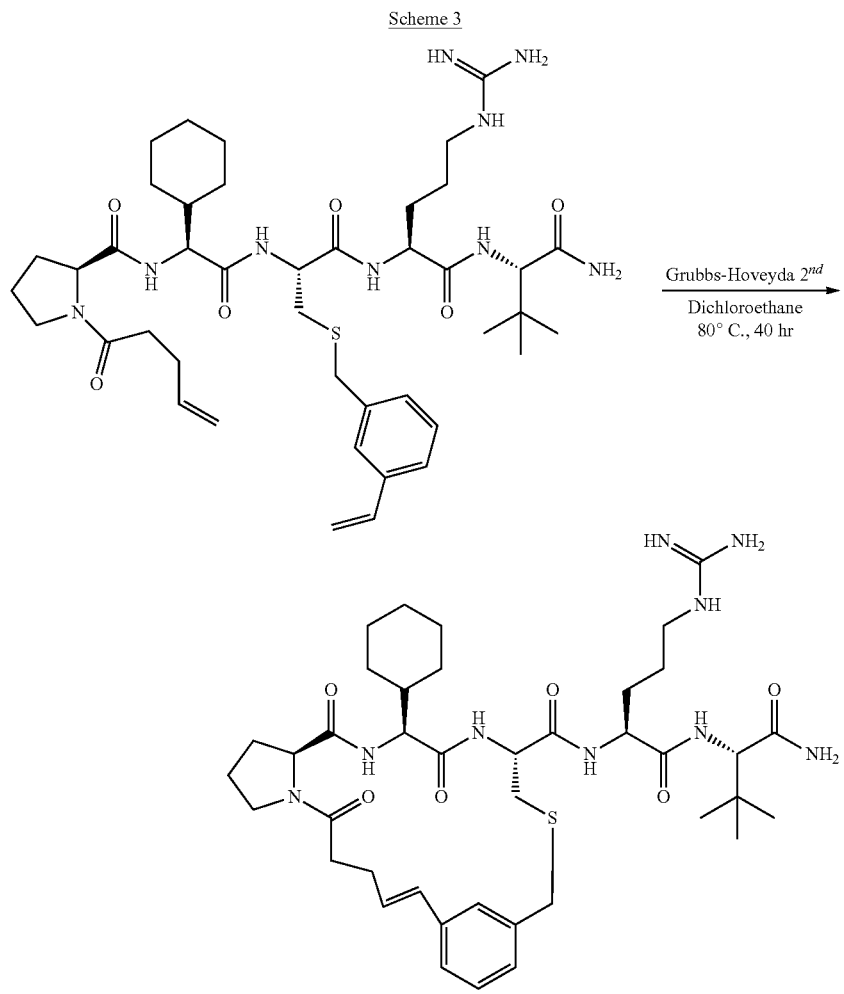

In some embodiments, the double bond formed in the reaction is in the S stereochemical formation. In some embodiments, the double bond formed in the reaction is in the R stereochemical formation.

Conjugates and Combinations

According to the present invention, the polypeptides may be modified by the addition of one or more conjugate groups. The peptides may also be administered in the combination with one or more additional molecules.

As used herein, a "conjugate" refers to any molecule or moiety appended to another molecule. In the present invention, conjugates may be protein (amino acid) based or not. Conjugates may comprise lipids, small molecules, RNA, DNA, proteins, polymers, or combinations thereof. Functionally, conjugates may serve as targeting molecules or may serve as payload to be delivered to a cell, organ or tissue. Conjugates are typically covalent modifications introduced by reacting targeted amino acid residues or the termini of the polypeptide with an organic derivatizing agent that is capable of reacting with selected side-chains or terminal residues. Such modifications are within the ordinary skill in the art and are performed without undue experimentation.

Covalent modifications specifically include molecules in which proteins, peptides or polypeptides of the invention are bonded to a non-proteinaceous polymer. The non-proteinaceous polymer ordinarily is a hydrophilic synthetic polymer, i.e. a polymer not otherwise found in nature. However, polymers that exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. The proteins, peptides or polypeptides may be linked to various non-proteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

As used herein when referring to polypeptides the terms "site" as it pertains to amino acid based embodiments is used synonymous with "amino acid residue" and "amino acid side chain". A site represents a position within a peptide or polypeptide that may be modified, manipulated, altered, derivatized or varied within the polypeptide based molecules of the present invention.

As used herein when referring to polypeptides the term "loop" refers to a structural feature of a polypeptide may serve to reverse the direction of the backbone of a peptide or polypeptide. Where the loop is found in a polypeptide and only alters the direction of the backbone, it may comprise four or more amino acid residues. Oliva et al. have identified at least 5 classes of protein loops (J. Mol Biol 266 (4): 814-830; 1997). Loops may be open or closed. Closed loops or "cyclic" loops may comprise 2, 3, 4, 5, 6, 7, 8, 9, 10 or more amino acids between the bridging moieties. Such bridging moieties may comprise a cysteine-cysteine bridge (Cys-Cys) typical in polypeptides having disulfide bridges or alternatively bridging moieties may be non-protein based such as the dibromozylyl agents used herein.

As used herein the terms "termini or terminus" when referring to polypeptides refers to an extremity of a peptide or polypeptide. Such extremity is not limited only to the first or final site of the peptide or polypeptide but may include additional amino acids in the terminal regions. The polypeptide based molecules of the present invention may be characterized as having both an N-terminus (terminated by an amino acid with a free amino group (NH2)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

In one embodiment, the polypeptide based molecules of the present invention may include a terminal region. As used herein, "terminal region" is a terminal region of amino acids that may include a cysteine. The terminal region may be a N- and/or a C-terminal region. The terminal region may be connected to the parent polypeptide using a linker. As used herein, "parent polypeptide" refers to the polypeptide that does not include the terminal region. The terminal region may be separated from the parent polypeptide by 1, 2, 3, 4, 5, 6, 7, 8, 9, 10 or more residues. The residues added may be selected from, but are not limited to, any natural or unnatural amino acid, the N-methylated form of any natural or unnatural amino acid, the D-stereoisomer of any natural or unnatural amino acid, norvaline, tert-butylglycine, phenylglycine, 7-azatryptophan, 4-fluorophenylalanine, penicillamine, sarcosine, homocysteine, 1-aminocyclopropanecarboxylic acid, 1-aminocyclobutanecarboxylic acid, 1-aminocyclopentanecarboxylic acid, 1-aminocyclohexanecarboxylic acid, 4-aminotetrahydro-2H-pyran-4-carboxylic acid, aminoisobuteric acid, (S)-2-amino-3-(1H-tetrazol-5-yl)propanoic acid, cyclopentylglycine, cyclohexylglycine, cyclopropylglycine, η-ω-methyl-arginine, 4-chlorophenylalanine, 3-chlorotyrosine, 3-fluorotyrosine, 5-fluorotryptophan, 5-chlorotryptophan, citrulline, 4-chloro-homophenylalanine, homophenylalanine, 4-aminomethyl-phenylalanine, 3-aminomethyl-phenylalanine, octylglycine, norleucine, tranexamic acid, 2-amino pentanoic acid, 2-amino hexanoic acid, 2-amino heptanoic acid, 2-amino octanoic acid, 2-amino nonanoic acid, 2-amino decanoic acid, 2-amino undecanoic acid, 2-amino dodecanoic acid, aminovaleric acid, and 2-(2-aminoethoxy)acetic acid, pipecolic acid, 2-carboxy azetidine, hexafluoroleucine, 3-Fluorovaline, 2-amino-4,4-difluoro-3-methylbutanoic acid, 3-fluoro-isoleucine, 4-fluoroisoleucine, 5-fluoroisoleucine, 4-methylphenylglycine, 4-ethyl-phenylglycine, 4-isopropyl-phenylglycine, (S)-2-amino-5-(3-methylguanidino)pentanoic acid, (S)-2-amino-3-(4-(aminomethyl)phenyl)propanoic acid, (S)-2-amino-3-(3-(aminomethyl)phenyl)propanoic acid, (S)-2-amino-4-(2-aminobenzo[d]oxazol-5-yl)butanoic acid, (S)-leucinol, (S)-valinol, (S)-tert-leucinol, (R)-3-methylbutan-2-amine, (S)-2-methyl-1-phenylpropan-1-amine, and (S)—N,2-dimethyl-1-(pyridin-2-yl)propan-1-amine, (S)-2-amino-3-(oxazol-2-yl)propanoic acid, (S)-2-amino-3-(oxazol-5-yl)propanoic acid, (S)-2-amino-3-(1,3,4-oxadiazol-2-yl)propanoic acid, (S)-2-amino-3-(1,2,4-oxadiazol-3-yl) propanoic acid, (S)-2-amino-3-(5-fluoro-1H-indazol-3-yl) propanoic acid, and (S)-2-amino-3-(1H-indazol-3-yl) propanoic acid.

In one embodiment, the polypeptide based molecules may include a terminal modification. The modification may be on the N- and/or C-termini and may include, but is not limited to, the addition of 1, 2, 3, 4, 5, 6, 7, 8, 9, 10 or more residues in the terminal region. The residues added may be selected from, but are not limited to, any natural or unnatural amino acid, the N-methylated form of any natural or unnatural amino acid, the D-stereoisomer of any natural or unnatural amino acid, norvaline, tert-butylglycine, phenylglycine, 7-azatryptophan, 4-fluorophenylalanine, penicillamine, sarcosine, homocysteine, 1-aminocyclopropanecarboxylic acid, 1-aminocyclobutanecarboxylic acid, 1-aminocyclopentanecarboxylic acid, 1-aminocyclohexanecarboxylic acid, 4-aminotetrahydro-2H-pyran-4-carboxylic acid, aminoisobuteric acid, (S)-2-amino-3-(1H-tetrazol-5-yl)propanoic acid, cyclopentylglycine, cyclohexylglycine, cyclopropylglycine, η-ω-methyl-arginine, 4-chlorophenylalanine, 3-chlorotyrosine, 3-fluorotyrosine, 5-fluorotryptophan, 5-chlorotryptophan, citrulline, 4-chloro-homophenylalanine, homophenylalanine, 4-aminomethyl-phenylalanine, 3-aminomethyl-phenylalanine, octylglycine, norleucine, tranexamic acid, 2-amino pentanoic acid, 2-amino hexanoic acid, 2-amino heptanoic acid, 2-amino octanoic acid, 2-amino nonanoic acid, 2-amino decanoic acid, 2-amino undecanoic acid, 2-amino dodecanoic acid, aminovaleric acid, and 2-(2-aminoethoxy)acetic acid, pipecolic acid, 2-carboxy azetidine, hexafluoroleucine, 3-Fluorovaline, 2-amino-4,4-difluoro-3-methylbutanoic acid, 3-fluoro-isoleucine, 4-fluoroisoleucine, 5-fluoroisoleucine, 4-methylphenylglycine, 4-ethyl-phenylglycine, 4-isopropyl-phenylglycine, (S)-2-amino-5-(3-methylguanidino)pentanoic acid, (S)-2-amino-3-(4-(aminomethyl)phenyl)propanoic acid, (S)-2-amino-3-(3-(aminomethyl)phenyl)propanoic acid, (S)-2-amino-4-(2-aminobenzo[d]oxazol-5-yl)butanoic acid, (S)-leucinol, (S)-valinol, (S)-tert-leucinol, (R)-3-methylbutan-2-amine, (S)-2-methyl-1-phenylpropan-1-amine, and (S)—N,2-dimethyl-1-(pyridin-2-yl)propan-1-amine, (S)-2-amino-3-(oxazol-2-yl)propanoic acid, (S)-2-amino-3-(oxazol-5-yl)propanoic acid, (S)-2-amino-3-(1,3,4-oxadiazol-2-yl)propanoic acid, (S)-2-amino-3-(1,2,4-oxadiazol-3-yl) propanoic acid, (S)-2-amino-3-(5-fluoro-1H-indazol-3-yl) propanoic acid, and (S)-2-amino-3-(1H-indazol-3-yl) propanoic acid.

In one embodiment, the polypeptide based molecules may include a terminal modification at the N- or C-termini with the addition of 1, 2, 3, 4, 5, 6, 7, 8, 9, 10 or more residues and a cysteine in the terminal region.

Once any of the features have been identified or defined as a component of a molecule of the invention, any of several manipulations and/or modifications of these features may be performed by moving, swapping, inverting, deleting, randomizing or duplicating. Furthermore, it is understood that manipulation of features may result in the same outcome as a modification to the molecules of the invention. For example, a manipulation which involved deleting a domain would result in the alteration of the length of a molecule just as modification of a nucleic acid to encode less than a full length molecule would.

Modifications and manipulations can be accomplished by methods known in the art such as site directed mutagenesis. The resulting modified molecules may then be tested for activity using in vitro or in vivo assays such as those described herein or any other suitable screening assay known in the art.

According to the present invention, the polypeptides may comprise a consensus sequence which is discovered through rounds of selection. In one embodiment the consensus sequence may comprise Cys-($X_1X_2X_3$-)Cys-Arg-Val-R, where the cysteines are joined to each other by a bridging moiety and —($X_1X_2X_3$—) represent a loop region of amino acids between the cysteines and where R represents zero, one or more amino acids.

The conjugation process may involve PEGylation, lipidation, albumination, the addition of other protein tails, or grafting onto antibody Fc domains, CDR regions of intact antibodies, or antibody domains produced by any number of means. The conjugate may include anchors including cholesterol oleate moiety, cholesteryl laurate moiety, an α-tocopherol moiety, a phytol moiety an oleate moiety or an unsaturated cholesterol-ester moiety or a lipophilic compound selected from acetanilides, anilides, aminoquinolines, benzhydryl compounds, benzodiazepines, benzofurans, cannabinoids, cyclic peptides, dibenzazepines, digitalis gylcosides, ergot alkaloids, flavonoids, imidazoles, quinolines, macrolides, naphthalenes, opiates (such as, but not limited to, morphinans or other psychoactive drugs), oxazines, oxazoles, phenylalkylamines, piperidines, polycyclic aromatic hydrocarbons, pyrrolidines, pyrrolidinones, stilbenes, sulfonylureas, sulfones, triazoles, tropanes, and ymca alkaloids. The peptides of the present invention may be conjugated to any of the peptide conjugates taught, for example, in US patent publications US20110172126 or US20030040472 the contents of which are incorporated herein by reference in their entirety.

Routes of Administration

The pharmaceutical compositions of the present invention may be administered by any route that results in a therapeutically effective outcome. These include, but are not limited to enteral, gastroenteral, epidural, oral, peridural, intracerebral (into the cerebrum), intratracheal (into the airways for delivery to the lung), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (into the posterior chamber of the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), buccal, sublingual, sublabial, enema, eye drops (onto the conjunctiva), or in ear drops.

Formulation and Delivery of Cyclic Peptides

The term "pharmaceutical formulation" refers to a composition comprising at least one active ingredient (e.g., such as a peptide) in a form and amount that permits the active ingredient to be therapeutically effective.

Peptide formulations of the present invention include controlled duodenal release formulations, time release formulations, osmotic-controlled release delivery systems, microemulsions, microspheres, liposomes, nanoparticles, patches, pumps, drug depots, and the like. Specifically included in the present invention are solid oral dosage forms, such as powders, softgels, gelcaps, capsules, pills, and tablets.

In one embodiment, the peptide is formulated as a sterile aqueous solution. In one embodiment, the peptide is formulated in a non-lipid formulation. In another embodiment, the peptide is formulated in a cationic or non-cationic lipid formulation. In either embodiment, the sterile aqueous solution may contain additional active or inactive components. Inactive components ("excipients") can include, but are not limited to, physiologically compatable salts, sugars, bulking agents, surfactants, or buffers.

Peptides or peptide compositions of the present invention may comprise or be formulated or delivered in conjunction with one or more carrier agents. The carrier agent can be a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, or hyaluronic acid); or lipid. The carrier molecule can also be a recombinant or synthetic molecule, such as a synthetic polymer, e.g., a synthetic polyamino acid. Examples of polyamino acids include polylysine (PLL), poly L aspartic acid, poly L-glutamic acid, poly(L-lactide-co-glycolide) copolymer, polyethylene glycol (PEG), polyvinyl alcohol (PVA), poly(2-ethylacryllic acid), and N-isopropylacrylamide polymers. Other useful carrier molecules can be identified by routine methods. PEG conjugates may vary in size (e.g. 5,000 kD (5K), 10,000 kD (10K), 20,000 kD (20K), 40,000 kD (40K), etc).

In one embodiment the pharmaceutical composition comprises the active peptide ingredient together with ethanol, corn oil-mono-di-triglycerides, hydrogenated castor oil, DL-tocopherol, propylene glycol, gelatin, glycerol, colorants, flavors and sweeteners.

In another embodiment the pharmaceutical composition comprises the active peptide ingredient together with a delivery agent such as 4-(2-hydroxy-4-methoxybenzamido) butanoic acid (or any of the delivery agents described in U.S. Pat. No. 7,744,910B2, the contents of which are incorporated herein by reference in their entirety), a pharmaceutically acceptable buffer, a disintegrant, hydroxypropylmethylcellulose, colorants, flavors and sweeteners.

In another embodiment, the pharmaceutical composition comprises a mix of the active ingredient together with ethanol, soy phosphatidyl choline, glycerol diolate which is injected into an excess of saline solution as described in US patent application 2008/0146490A1, the contents of which are incorporated herein by reference in their entirety.

The delivery of one or more peptides or cyclic peptides to a subject in need thereof can be achieved in a number of different ways. In vivo delivery can be performed directly by administering a composition comprising a cyclic peptide, to a subject. Alternatively, delivery can be performed indirectly by administering one or more vectors that encode and direct the expression of the cyclic peptide.

Local delivery avoids gut permeability and systemic exposure. For example, peptides of the present invention may be used in the eye as a drop or in posterior section of the eye by direct injection. They may be applied in the gut to target enzymes. They may be used topically in dermatologic applications (e.g., creams, ointments, transdermal patches) or ocular applications (e.g., eye drops).

Peptides or peptide compositions of the present invention may comprise or be formulated with one or more fusogenic agents. A fusogenic agent of a composition described herein can be an agent that is responsive to, e.g., changes charge depending on, the pH environment. Upon encountering the pH of an endosome, it can cause a physical change, e.g., a change in osmotic properties that disrupts or increases the permeability of the endosome membrane. Preferably, the fusogenic agent changes charge, e.g., becomes protonated, at pH lower than physiological range. For example, the fusogenic agent can become protonated at pH 4.5-6.5. The fusogenic agent can serve to release the polypeptide into the cytoplasm of a cell after the composition is taken up, e.g., via endocytosis, by the cell, thereby increasing the cellular concentration of the peptide in the cell.

In one embodiment, the fusogenic agent can have a moiety, e.g., an amino group, which, when exposed to a specified pH range, will undergo a change, e.g., in charge, e.g., protonation. The change in charge of the fusogenic agent can trigger a change, e.g., an osmotic change, in a vesicle, e.g., an endocytic vesicle, e.g., an endosome. For example, the fusogenic agent, upon being exposed to the pH environment of an endosome, will cause a solubility or osmotic change substantial enough to increase the porosity of (preferably, to rupture) the endosomal membrane.

The fusogenic agent can be a polymer, preferably a polyamino chain, e.g., polyethyleneimine (PEI). The PEI can be linear, branched, synthetic or natural. The PEI can be, e.g., alkyl substituted PEI, or lipid substituted PEI.

In other embodiments, the fusogenic agent can be polyhistidine, polyimidazole, polypyridine, polypropyleneimine, mellitin, or a polyacetal substance, e.g., a cationic polyacetal. In some embodiment, the fusogenic agent can have an alpha helical structure. The fusogenic agent can be a membrane disruptive agent, e.g., mellittin.

Other suitable fusogenic agents can be tested and identified by a skilled artisan.

The peptide compositions of the present invention may comprise or be formulated with one or more condensing agents. The condensing agent of a composition described herein can interact with (e.g., attracts, holds, or binds to) a peptide and act to (a) condense, e.g., reduce the size or charge of the peptide and/or (b) protect the peptide, e.g., protect the peptide against degradation. The condensing agent can include a moiety, e.g., a charged moiety, which can interact with a peptide by ionic interactions. The condensing agent would preferably be a charged polymer, e.g., a polycationic chain. The condensing agent can be a polylysine (PLL), spermine, spermidine, polyamine, pseudopeptide-polyamine, peptidomimetic polyamine, dendrimer polyamine, arginine, amidine, protamine, cationic lipid, cationic porphyrin, quarternary salt of a polyamine, or an alpha helical peptide.

In one embodiment, the peptide compositions of the present invention may be formulated as bicyclic peptides. As a non-limiting example, bicyclic peptide inhibitors of kallikrein may be produced in combinatorial libraries (see e.g., Baeriswyl et al., "Bicyclic Peptides with Optimized Ring Size Inhibit Human Plasma Kallikrein and its Orthologues While Sparing Paralogous Proteases," ChemMedChem, 2012. http://onlinelibrary.wiley.com/doi/10.1002/cmdc.201200071/abstract; the contents of which is herein incorporated by reference in its entirety). The bicyclic peptides may have 2, 3, 4, 5, 6 or more amino acids per loop.

Kallikrein Inhibitors

In one embodiment, the cyclic peptides bind to and/or inhibit the activity of plasma kallikrein. Inhibitors of plasma kallikrein may find utility in eliminating or reducing various ischemias, including but not limited to perioperative blood loss, cerebral ischemia, the onset of systemic inflammatory response (SIR), and/or reperfusion injury, e.g., reperfusion injury associated with cerebral ischemia or a focal brain ischemia. Certain plasma kallikrein inhibitors are known in the art and are taught in U.S. Pat. Nos. 6,333,402 and 6,057,287; both of which are herein incorporated by reference in their entireties.

Inhibitors of plasma kallikrein may also be useful in the treatment of disorder selected from the group consisting of rheumatoid arthritis, gout, intestinal bowel disease, oral mucositis, neuropathic pain, inflammatory pain, spinal stenosis-degenerative spine disease, arterial or venous thrombosis, post operative ileus, aortic aneurysm, osteoarthritis, vasculitis, edemas (including, but not limited to, diabetic macular edema, cerebral edema, intracerebral edema, and radiation-induced edema), hemorrhage, pulmonary embolism, stroke, clotting on ventricular assistance devices or stents, head trauma or peri-tumor brain edema, sepsis, acute middle cerebral artery (MCA) ischemic event (stroke), restenosis (e.g., after angioplasty), systemic lupus erythematosis nephritis, burn injury, embolism, intracerebral hemorrhage (ICH), inflammation, acute myocardial infarction (MI), deep vein thrombosis (DVT), coagulations from post fibrinolytic treatment conditions (e.g., tissue plasminogen activator and streptokinase), angina angioedema, joint swelling, lesions in lipopolysaccharides (LPS) diabetes and its complications, and retinopathy.

A genetic deficiency in the C1-inhibitor protein (C1-INH), the major natural inhibitor of plasma kallikrein, leads to hereditary angioedema (HAE). Patients with HAE suffer from acute attacks of painful edema often precipitated by unknown triggers (Zuraw B. L. et al., N Engl J Med 359, 1027-1036, 2008). Inhibitors disclosed herein are particularly useful in the treatment of either acute or chronic HAE.

Further examples of applications for kallikrein inhibitors include pediatric cardiac surgery, lung transplantation, total hip replacement and orthotopic liver transplantation, and to reduce or prevent perioperative stroke during CABG and extracorporeal membrane oxygenation (ECMO), and reduce or prevent cerebrovascular accidents (CVA) during these procedures. Kallikrein inhibitors can also be used for stroke, e.g., embolism, thrombus and/or hemorrhage associated stroke and for reperfusion injury associated with stroke.

Vascular Permeability and Diabetic Retinopathy

Diseases which have been associated with an increase in vascular permeability (e.g., retinal vascular permeability) include, but are not limited to, diabetes (e.g., type-1 or type-2 diabetes mellitus), hypertension, insulin resistance, ketoacidosis, trauma, infection, and hyperglycemia, diabetic retinopathy (e.g., proliferative or nonproliferative retinopathy), edema, hereditary angioedema (HAE) edema in the brain, including, but not limited to, cerebral edema (e.g., high altitude edema), hemorrhage, intracerebral hemorrhage, subdural hemorrhage, sub-arachnoid hemorrhage, hemorrhagic stroke, hemorrhagic transformation of ischemic stroke, vascular permeability associated with hypertension or inflammation, increased systemic vascular permeability, e.g., associated with septic shock, scurvy, anaphylaxis, hereditary or acquired angioedema (both of which have been linked to C1 inhibitor deficiency), brain aneurysm, and arterial-venous malformation. Cerebral edema is an increase in brain volume caused by an absolute increase in cerebral tissue fluid content; vasogenic cerebral edema arises from transvascular leakage caused by mechanical failure of the endothelial tight junctions of the blood-brain barrier (BBB). In some instances, cerebral edema can be caused by high altitude (e.g., a rapid transition to at least 8,000 ft above sea level).

Kallikrein may be used as a therapeutic target for people with diabetic retinopathy as it has been shown that kallikrein contributes to an increase in blood vessel leakage and the thickening of the retina which is a leading cause of diabetic retinopathy. Diabetic retinopathy is characterized by gradual progressive alterations in the retinal microvasculature leading to areas of retinal non-perfusion, increased vascular permeability and pathologic intraocular proliferation of retinal vessels. As used herein, "vascular permeability" is meant the passage of substances, including molecules, particles, and cells, across the vascular endothelium. Disorders associated with excessive vascular permeability and/or edema in the eye, e.g., in the retina or vitreous, include, but are not limited to, age-related macular degeneration (AMD), retinal edema, retinal hemorrhage, vitreous hemorrhage, macular edema (ME), diabetic macular edema (DME), proliferative diabetic retinopathy (PDR) and non-proliferative diabetic retinopathy (DR), radiation retinopathy, telangiectasis, central serous retinopathy, retinal vein occlusions (e.g., branch or central vein occlusions), radiation retinopathy, sickle cell retinopathy, retinopathy of prematurity, Von Hipple Lindau disease, posterior uveitis, chronic retinal detachment, Irvine Gass Syndrome, Eals disease, retinitis, and choroiditis.

Increases in the rate or amount of such passage (i.e., increased vascular permeability) can be indicative of the disease states described herein. The complications associated with the increased vascular permeability in the macula (termed macular edema) and uncontrolled neovascularization (termed proliferative diabetic retinopathy) can result in severe and permanent visual loss. Diabetic retinopathy progresses in a predictable fashion through distinctly definable stages. It is divided into two broad categories, non-proliferative diabetic retinopathy (NPDR) and proliferative diabetic retinopathy (PDR) and is further subdivided by level of severity.

Diabetic macular edema (DME) is a major cause of moderate visual loss and legal blindness in persons with type 2 diabetes (Javitt et al., Diabetes Care. 17:909-917 (1994)). 20 to 25% of the at least 346 million diabetics worldwide will develop DME. DME can occur at any level of NPDR or PDR. DME develops when a breakdown of the blood-retinal barrier allows fluid and other plasma components to leak from blood vessels into the retina. The blood-retinal barrier breakdown, which can be detected as increased vascular permeability, may be observed in the diabetic retina before any other retinopathic changes are seen. The activation of prekallikrein has been shown to result in the increased retinal vascular permeability where the greater the amount of retinal vascular permeability, the greater the chance of the progression of DME and, ultimately, vision loss.

The kallikrein inhibitors described herein may be used to decrease blood vessel leakage and the thin the retina as a method to treat and/or prevent diabetic retinopathy. The kallikrein inhibitors may be further used in combination with current treatments and therapies for DME such as, but not limited to, laser photocoagulation, laser photocoagulation and lucentis injections, anti-VEGF agents and corticosteroid intravitreal and/or implant therapy, intravitreal steroid implants, combinations of laser photocoagulation with pharmacotherapy, eye drops containing a small molecule antagonist of bradykinin B1 receptor, single intravitreal injection of a pharmaceutical composition containing a kallikrein inhibitor, and an oral pharmaceutical composition containing a small molecule plasma kallikrein inhibitor. T Topical delivery may be particularly useful for treating DME. In this embodiment, the peptide may be injected directly into the posterior chamber (intravitreously) of the eye. The peptide may be in a reservoir or embedded in a biodegradable polymer microparticle or nanoparticle. The peptides may be used in combination with approved therapies for wet age-related macular degeneration and/or DME, such as Lucentis® (Roche-Genentech-Novartis) or Eylea™ (Regeneron-Bayer) to augment the effectiveness of the approved products.

In HAE, the normal regulation of plasma kallikrein activity and the classical complement cascade is not present and the unregulated activity of plasma kallikrein results in excessive bradykinin generation. The kallikrein inhibitors of the present invention may be used alleviate edema in patients with HAE and may further inhibit bradykinin production to alleviate edema in patients with HAE. For the treatment of HAE, kallikrein inhibitors of the present invention may be delivered by a method such as, but not limited to, oral, parenteral, depot, transdermal, or any other suitable route that achieves adequate systemic exposure. The peptides may be used with other medications, for example steroids (danazol, oxandrolone and stanozolol) and pain medications commonly used to treat HAE, and may be used with other approved products used for the treatment of HAE [e.g. KALBITOR® (Dyax Corp., Burlington Mass.), FIRAZYR® (Shire, Dublin Ireland), Berinert® (CSL Behring, Prussia, Pa.), or CINRYZE™ (ViroPharma, Exton Pa.)] in order to augment the efficacy of the approved products.

Surgical Procedures

Treating a systemic inflammatory response induced by kallikrein with kallikrein inhibitors may be especially beneficial, for example, in patients undergoing surgical procedures such as, but not limited to, procedures involving cardiothoracic surgery, e.g., cardiopulmonary bypass (CPB) and coronary artery bypass graft (CABG) procedures. Cardiothoracic surgery generally refers to surgery of the chest area, such as, but not limited to, surgery of the heart and lungs. Diseases which may be treated by cardiothoracic surgery include, but are not limited to, coronary artery disease, tumors and cancers of the lung, esophagus and chest wall, heart vessel and valve abnormalities, and birth defects involving the chest or heart. When cardiothoracic surgery is used for treatment, there is a risk of blood loss (e.g., surgery-induced ischemia) and a risk for the onset of systemic inflammatory response (SIR) which may result in severe organ dysfunction (e.g., systemic inflammatory response syndrome (SIRS)).

Using kallikrein inhibitors to treat and/or prevent perioperative blood loss and reduce heart blood flow may be helpful as a number of highly invasive surgical procedures are carried out each day that result in blood loss, or place patients at a high risk for blood loss. Surgical procedures that involve blood loss include, but are not limited to, those involving extra-corporeal circulation methods such as cardiothoracic surgery, e.g., CPB. In such methods, a patient's heart is stopped and the circulation, oxygenation, and maintenance of blood volume are carried out using artificial means by an extra-corporeal circuit and a synthetic membrane oxygenator. Additionally, with cardiothoracic surgery, e.g., CPB and/or surgery involving extensive trauma to bone, such as, but not limited to, hip replacement procedures and the sternal split necessary in CABG, the contact of a patient's blood with the cut surfaces of bone and/or CPB equipment may be sufficient to active one or several undesirable cascade responses which can result in a variety of disruptions in the blood and vasculature. Such responses include, but are not limited to, a contact activation system (CAS) response, which can lead to extensive perioperative blood loss which may require an immediate blood transfusion, as well as a systemic inflammatory response (SIR), which, in turn, can result in permanent damage to a patient's tissues and organs.

For example, CABG procedures may be used in the treatment of atherosclerotic coronary artery disease (CAD) to bridge the occluded blood vessel and restore blood to the heart. Atherosclerosis CAD causes a narrowing of the lumen of one or several of the coronary arteries which limits the flow of blood to the myocardium (i.e., the heart muscle) and can cause angina, heart failure, and myocardial infarcts. In the end stage of coronary artery atherosclerosis, the coronary circulation can be almost completely occluded, causing life threatening angina or heart failure, with a very high mortality. CABG procedures are among the most invasive of surgeries in which one or more healthy veins or arteries are implanted to provide a "bypass" around the occluded area of the diseased vessel. Despite these very encouraging results, repeat CABG procedures are frequently necessary, as indicated by an increase in the number of patients who eventually undergo second and even third procedures and the perioperative mortality and morbidity seen in the primary CABG procedures is increased when the procedure is done for the second and third time.

Nearly all CABG procedures performed for valvular and/or congenital heart disease, heart transplantation, and major aortic procedures, are still carried out on patients supported by CPB. In CPB, large cannulae are inserted into the great vessels of a patient to permit the mechanical pumping and oxygenation of the blood using a membrane oxygenator. The blood is then returned to the patient without flowing through the lungs, as the lungs are hypoperfused during this procedure. CPB has been extensively used in a variety of procedures performed for nearly half a century with successful outcomes. The interaction between artificial surfaces, blood cells, blood proteins, damaged vascular endothelium, and extravascular tissues, such as bone, disturbs hemostasis and frequently activates the CAS, which, as noted above, can result in a variety of disruptions in the blood and vasculature. Such disruption leads to excess perioperative bleeding, which can require an immediate blood transfusion. A consequence of circulating whole blood through an extracorporeal circuit in CPB can also include the activation of the systemic inflammatory response (SIR), which is initiated by contact activation of the coagulation and complement systems.

Much of the morbidity and mortality associated with CPB surgical procedures is the result of the effects of activating coagulation, fibrinolysis, or complement systems. Such activation can damage the pulmonary system, leading to adult respiratory distress syndrome (ARDS), impairment of kidney and splanchnic circulation, and induction of a general coagulopathy leading to blood loss and the need for transfusions. In addition, pathologies associated with SIR include, but are not limited to, neurocognitive deficits, stroke, renal failure, acute myocardial infarct, and cardiac tissue damage may be seen with the activation of coagulation, fibrinolysis, or complement systems.

Administering blood transfusions elevate the cost of CABG or other similar procedures that require CPB and also present a significant risk of infection. In the absence of any pharmacological intervention, three to seven units of blood must typically be expended on a patient, even with excellent surgical techniques. Accordingly, there is considerable incentive for the development of new and improved pharmacologically effective compounds to reduce, treat and/or prevent perioperative bleeding and SIR in patients subjected to procedures such as, but not limited to, CPB and CABG. Use of the kallikrein inhibitors described herein may improve these various procedures and also may lead to amelioration of the undesirable symptoms that can occur with these procedures.

Cerebral Ischemia and Reperfusion Injury

The kallikrein inhibitors described herein may be useful for reducing and/or preventing cerebral ischemia as well as reperfusion injury associated with cerebral ischemia. An ischemic condition in which the blood supply to the brain is block may be known as a cerebral ischemic attack and/or cerebral ischemia. This interruption in the blood supply to the brain may result from a variety of causes including, but not limited to, an intrinsic blockage or occlusion of the blood vessel itself, a remotely originated source of occlusion, decreased perfusion pressure or increased blood viscosity resulting in decreased cerebral blood flow, or ruptured or leaky blood vessels in the subarachnoid space or intracerebral tissue. Cerebral ischemia may result in either transient or permanent deficits and the seriousness of the neurological damage in a patient who has experienced cerebral ischemia depends on the intensity and duration of the ischemia event. A transient ischemia attack (TIA) is one in which the blood flow to the brain is briefly interrupted and causes temporary neurological deficits. Symptoms of TIA include numbness of weakness of face or limbs, loss of ability to speak clearly and/or understand the speech of others, a loss of vision or dimness of vision and dizziness. Permanent cerebral ischemia attacks, also known as strokes, are caused by a longer interruption in blood flow to the brain resulting from an embolism, a thrombus or bleeding in the brain (e.g., a hemorrhage). The terms "thromboembolic stroke" or "thromboembolism" as used herein to refer to a stroke which has been caused by either a thrombosis or an embolism. A stroke causes a loss of neurons which can result in a neurological deficit that may improve but it will not entirely resolve. The kallikrein inhibitors described herein may be useful to prevent and/or reduce the change of a stroke including, but not limited to, embolic, thrombolic, thromboembolic and hemorrhage-associated strokes.

Strokes may be a result of a variety of causes. One category of strokes includes perioperative strokes that can be associated with thrombus or embolism formation. In stroke patients, there is a core of the neurological deficit marked by total ischemia and/or tissue necrosis. This area is normally surrounded by ischemic tissue, referred to as the ischemic penumbra, which receives collateral circulation. Ischemia in the penumbra does not always result in irreversible damage. In some cases, the restoration of blood flow (reperfusion) into the penumbra may prevent total ischemia and necrosis in this area. However, reperfusion has also been associated with injury to the tissue surrounding the core.

Once blood flow is returned, blood cells such as neutrophils, attack the damaged tissue which in turn cause additional inflammation and/or damage. Reperfusion injury is associated with an influx of neutrophils into the affected tissue and subsequent activation of the neutrophils. Neutrophils can release lytic enzymes that directly induce tissue damage and proinflammatory mediators such as cytokines that amplify local inflammatory reaction. The influx of neutrophils to a site of ischemic damage can also plug capillaries and cause vasoconstriction. Kallikrein has been found to play a role in neutrophil chemotaxis, neutrophil activation and reperfusion injury. Thus, the kallikrein inhibitors described herein may be used to prevent and/or reduce reperfusion injury and may halt and/or hinder the ischemic cascade. As a non-limiting example, the reperfusion injury may be reduced and/or prevented using kallikrein inhibitors to reduce and/or prevent one or more of: neutrophil infiltration, neutrophil activation, cytokine release, elastase release, vasodilation, brain edema, infarct volume and neurological deficits.

In surgical indications, stroke, and intracerebral hemorrhage, local or systemic administration of the kallikrein inhibitors described herein may be effective treatment options. For local administration, peptides may be embedded in sponges, sheets, and films for optimizing vascular contact.

A variety of inhibitors of a kallikrein, e.g., a plasma kallikrein which may be useful in the treatment of the foregoing are described herein.

In one embodiment, the kallikrein inhibitors described herein may include a terminal modification at the N- or C-termini with the addition of 1, 2, 3, 4, 5, 6, 7, 8, 9, 10 or more residues. In a further embodiment, the terminal modification at the N- or C-termini may include the addition of 1, 2, 3, 4, 5, 6, 7, 8, 9, 10 or more residues and a cysteine in the terminal region.

In one embodiment, the kallikrein inhibitors described herein may include at least 1, at least 2 or at least 3 cysteine residues. In a further embodiment, the kallikrein inhibitors may contain a terminal modification at the N- or C-termini and may include the addition of 1, 2, 3, 4, 5, 6, 7, 8, 9, 10 or more residues and a cysteine in the terminal region. The terminal modification and/or the addition of a cysteine in the terminal region may improve drug activity such as, but not limited to, potency of the kallikrein inhibitors. As a non-limiting example, the kallikrein inhibitors described in Tables 1, 2, 3, 4, 5, 6 and 9 may include a terminal modification of 1, 2, 3, 4, 5, 6, 7, 8, 9, 10 or more residues at the N-terminus wherein one of the additional residues is cysteine to improve potency.

Methods for Treating Diseases

The invention relates in particular to the use of peptide or peptide mimetics, often cyclic, and compositions containing at least one peptide, for the treatment of a disorder, condition or disease.

As used herein the terms "treat," "treatment," and the like, refer to relief from or alleviation of pathological processes. In the context of the present invention insofar as it relates to any of the other conditions recited herein below, the terms "treat," "treatment," and the like mean to relieve or alleviate at least one symptom associated with such condition, or to slow or reverse the progression or anticipated progression of such condition, such as slowing the progression of a malignancy or cancer, or increasing the clearance of an infectious organism to alleviate/reduce the symptoms caused by the infection, e.g., hepatitis caused by infection with a hepatitis virus.

By "lower" or "reduce" in the context of a disease marker or symptom is meant a statistically significant decrease in such level. The decrease can be, for example, at least 10%, at least 20%, at least 30%, at least 40% or more, and is preferably down to a level accepted as within the range of normal for an individual without such disorder.

By "increase" or "raise" in the context of a disease marker or symptom is meant a statistically significant rise in such level. The increase can be, for example, at least 10%, at least 20%, at least 30%, at least 40% or more, and is preferably up to a level accepted as within the range of normal for an individual without such disorder.

As used herein, the phrases "therapeutically effective amount" and "prophylactically effective amount" refer to an amount that provides a therapeutic benefit in the treatment, prevention, or management of pathological processes or an overt symptom of one or more pathological processes. The specific amount that is therapeutically effective can be readily determined by an ordinary medical practitioner, and may vary depending on factors known in the art, such as, for example, the type of pathological processes, the patient's history and age, the stage of pathological processes, and the administration of other agents that inhibit pathological processes.

As used herein, a "pharmaceutical composition" comprises a pharmacologically effective amount of a peptide and a pharmaceutically acceptable carrier. As used herein, "pharmacologically effective amount," "therapeutically effective amount" or simply "effective amount" refers to that amount of a peptide effective to produce the intended pharmacological, therapeutic or preventive result. For example, if a given clinical treatment is considered effective when there is at least a 10% alteration (increase or decrease) in a measurable parameter associated with a disease or disorder, a therapeutically effective amount of a drug for the treatment of that disease or disorder is the amount necessary to effect at least a 10% alteration in that parameter. For example, a therapeutically effective amount of a peptide may be one that alters binding of a target to its natural binding partner by at least 10%.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Agents included in drug formulations are described further herein below.

Efficacy of treatment or amelioration of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. In connection with the administration of a peptide or pharmaceutical composition thereof, "effective against" a disease or disorder indicates that administration in a clinically appropriate manner results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of disease or disorder.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given peptide drug or formulation of that drug can also be judged using an experimental animal model for the given disease as known in the art. When using an experimental animal model, efficacy of treatment is evidenced when a statistically significant reduction in a marker or symptom is observed.

The peptide and an additional therapeutic agent can be administered in combination in the same composition, e.g., parenterally, or the additional therapeutic agent can be administered as part of a separate composition or by another method described herein.

Dosage and Administration

For use as treatment of human subjects, peptides can be formulated as pharmaceutical compositions. Depending on the subject to be treated, the mode of administration, and the type of treatment desired (e.g., prevention, prophylaxis, or therapy) the peptides are formulated in ways consonant with these parameters. A summary of such techniques is found in Remington: The Science and Practice of Pharmacy, 21st Edition, Lippincott Williams & Wilkins, (2005); and Encyclopedia of Pharmaceutical Technology, eds. J. Swarbrick and J. C. Boylan, 1988-1999, Marcel Dekker, New York, each of which is incorporated herein by reference.

Compositions of the present invention are preferably provided in a therapeutically effective amount, which may be, for example, a daily amount of from 1 mg to 1,600 mg, more preferably 10 mg to 800 mg, and even more preferably 100 mg to 400 mg. In one embodiment, a pharmaceutical composition comprises a capsule, for example in unit dosage form.

Unit Dosage Forms

The peptides of the invention may be present in amounts totaling 1-95% by weight of the total weight of the composition. The composition may be provided in a dosage form that is suitable for oral administration. Thus, the pharmaceutical composition may be in the form of, e.g., hard capsules (e.g., hard gelatin capsules or hard hydroxypropyl methylcellulose capsules), soft gelatin capsules, tablets, caplets, enteric coated tablets, chewable tablets, enteric coated hard gelatin capsules, enteric coated soft gelatin capsules, minicapsules, lozenges, films, strips, gelcaps, dragees, solutions, emulsions, suspensions, syrups, or sprays.

Patients can be administered a therapeutic amount of a peptide, such as 0.01 mg/kg, 1.0 mg/kg, or 15 mg/kg. For administration to human subjects, the dosage of peptides of the present invention, is typically 0.01 to 15 mg/kg, more preferably 3 to 5 mg/kg. However, dosage levels can be highly dependent on the nature of the condition, drug efficacy, the condition of the patient, the judgment of the practitioner, and the frequency and mode of administration.

In other embodiments, the peptides are administered at a frequency of e.g., every 4 hr, every 6 hr, every 12 hr, every 18 hr, every 24 hr, every 36 hr, every 72 hr, every 84 hr, every 96 hr, every 5 days, every 7 days, every 10 days, every 14 days, every 3 weeks, or more. The compositions can be administered once daily or the peptide can be administered as two, three, or more sub-doses at appropriate intervals throughout the day or delivery through a controlled release formulation. In that case, the peptide contained in each sub-dose must be correspondingly smaller in order to achieve the total daily dosage. The dosage unit can also be compounded for delivery over several days, e.g., using a conventional sustained release formulation, which provides sustained release of the peptide over a several-day-period.

Sustained release formulations are well known in the art and are particularly useful for delivery of agents to a particular site, such as could be used with the peptide compositions of the present invention. The effect of a single dose can be long-lasting, such that subsequent doses are administered at not more than 3-, 4-, or 5-day intervals, or at not more than 1, 2-, 3-, or 4-week intervals.

The peptide can be administered by intravenous infusion over a period of time, such as over a 5 minute, 10 minute, 15 minute, 20 minute, or 25 minute period. The administration may be repeated, for example, on a regular basis, such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of the peptide or composition can reduce, lower, increase or alter binding or any physiologically deleterious process, e.g., in a cell, tissue, blood, urine or other compartment of a patient by at least 10%, at least 15%, at least 20%, at least 25%, at least 30%, at least 40%, at least 50%, at least 60%, at least 70%, at least 80% or at least 90% or more.

Before administration of a full dose of the peptide or composition, patients can be administered a smaller dose, such as a 5% infusion reaction, and monitored for adverse effects, such as an allergic reaction, or for elevated lipid levels or blood pressure. In another example, the patient can be monitored for unwanted immunostimulatory effects, such as increased cytokine (e.g., TNF-alpha or INF-alpha) levels.

Genetic predisposition plays a role in the development of some diseases or disorders. Therefore, a patient in need of a peptide or peptide composition may be identified by taking a family history, or, for example, screening for one or more genetic markers or variants. A healthcare provider, such as a doctor, nurse, or family member, can take a family history before prescribing or administering a therapeutic composition of the present invention. For example, a genetic deficiency of the C-1 inhibitor protein leads to hereditary angioedema. A blood test may also be performed on the patient to determine if the patient is deficient for C-1 inhibitor before a peptide is administered to the patient.

Kits

Any of the compositions described herein may be comprised in a kit. In a non-limiting example, peptides may be included in a kit for treating a disease. The kit may include a vial of sterile, dry peptide power, sterile solution for dissolving the dried power, and a syringe for infusion set for administering the peptide.

When peptides are provided as a dried power it is contemplated that between 10 micrograms and 1000 milligrams, or at least or at most those amounts of peptides are provided in kits of the invention The container means will generally include at least one vial, test tube, flask, bottle, syringe and/or other container means, into which the peptide formulations are placed, preferably, suitably allocated. The kits may also comprise a second container means for containing a sterile, pharmaceutically acceptable buffer and/or other diluent.

A kit can include instructions for employing the kit components as well the use of any other reagent not included in the kit. Instructions may include variations that can be implemented.

While various embodiments of the invention have been particularly shown and described, it will be understood by those skilled in the art that various changes in form and details may be made therein without departing from the spirit and scope of the invention as defined by the appended claims.

EXAMPLES

Example 1

Activation of Human Pre-Kallikrein by Human Factor Alpha-XIIa

Pre-kallikrein (Enzyme Research Laboratories, HPK 1302) was activated by Human Factor Alpha-XIIa (Enzyme Research Laboratories, HFXIIa 1212a) at an 80:1 molar ratio in 50 mM Tris-HCl pH 7.4, 150 mM NaCl and 0.02% Tween-20 for 10 minutes at 37° C. The reaction was quenched with 0.1M NaOAc, dialyzed overnight at 4° C. in 10 mM NaOAc, 150 mM NaCl, pH 5.2 and stored at −80° C.

Example 2

Isolation and Activation of Recombinant Plasma Kallikrein

According to the present invention, a recombinantly expressed fragment of human plasma kallikrein (expressed as Gly20-Ala638 fragment in NS0-derived murine myeloma cell line corresponding to the proform without signal peptide) with a C-terminal His-tag (Swiss-Prot accession number P03952) is purified in the proform. Activation (e.g. with thermolysin or Factor XIIa) is carried out by converting the proform to a heavy and a light chain which are linked by disulfide bonds. Subsequent biotinylation is then carried out using Sulfo-NHS-LC-Biotin.

Example 3

Large Scale Biotinylation of Plasma Kallikrein

Activated plasma kallikrein (pKAL) at 3.7 µM (0.31 mg/ml) in acetic acid buffer pH 5.2 was used to make biotinylated pKAL. Sulfo-NHS-LC-Biotin (Thermo Scientific #21327) was freshly prepared according to manufactures instructions. A ten fold molar excess of Sulfo-NHS-LC_Biotin to-pKAL protein was used based on pilot testing.

The final concentrations in the reaction mixture were 2.47 µM pKAL and 24.7 µM Sulfo-NHS-LC-Biotin in 10 mM Sodium Phosphate buffer pH 8.0. The mixture was aliquoted to 100 µl×12 tubes and incubated at 4° C. for 2 hours. The reaction was stopped by adding 1M Tris-HCl pH 7.5 to a final concentration of 0.16 M into each tube and incubated on ice for 10 min. The biotinylated pKAL was then dialyzed in 10 mM acetate and 150 mM NaCl pH 5.3 overnight at 4° C. After dialysis the efficiency of biotinylation was determined using SA ultralink resin (Thermo Scientific #53114) to pull down the biotin-pKAL and the concentration was estimated by running known amounts of pKAL on a 4-12% Bis-Tris gel (Invitrogen #NP0322BOX). The biotinylated pKAL was aliquoted and stored at −80° C.

Example 4

Enzyme Inhibition Assay

Activated human plasma kallikrein (Enzyme Research Laboratories, HPKa 1303) was reacted with H-Pro-Phe-Arg-7-amido-4-methylcoumarin (H-Pro-Pre-Arg-AMC) (a fluorogenic substrate for plasma as well as pancreatic and urinary kallikreins; Bachem I-1295) and candidate inhibitory peptides to determine the $IC_{50}$ of the inhibitor.

Ten 8-fold serial dilutions of peptides (10 mM DMSO stocks) were performed in DMSO and then added to TCNB (50 mM Tris-HCl pH 7.2, 150 mM NaCl, 10 mM $CaCl_2$, 0.05% Brij-35) and sonicated. 50 µL of the peptide dilutions were added to microtitre plates (96 well, black non-binding surface, Corning, 3650) and incubated for 5 minutes at room temperature with 4 nM activated human kallikrein (final concentration after addition of fluorogenic substrate: 1 nM). The samples were then incubated for 1 hour at room temperature with 2 mM H-Pro-Phe-Arg-AMC (final concentration 500 µM). Relative Fluorescence Units (RFU) were measured at excitation/emission 360 nm/460 nm by a SpectraMax M3.

Example 5

Activity of Biotinylated pKAL

Biotinylated and non-biotinylated pKAL were incubated with H-Pro-Phe-Arg-7-amido-4-methylcoumarin (H-Pro-Pre-Arg-AMC) (Bachem I-1295, 200 mM stock in DMSO). 1 nM biotinylated or non-biotinylated pKAL were incubated with different concentrations of H-Pro-Phe-Arg-AMC in freshly prepared TCNB (50 mM Tris-HCl pH 7.4, 150 mM NaCl, 10 mM $CaCl_2$ and 0.5% Brij-35). Fluorescence was measured after 10 minutes at 360 nm and Emission 460 nm. Vmax and $EC_{50}$ were calculated using SoftMax Pro software. Comparison of the activity of pKAL before and after biotinylation revealed that biotinylated pKAL and non-biotinylated pKAL have comparative activities while substrate alone had no activity.

Example 6

Isolation of Peptides Binding Plasma Kallikrein

Kallikrein inhibitors were identified through several rounds of mRNA display and selection. mRNA display was performed generally as described (Roberts, R. W., and Szostak, J. W. (1997). Proc. Natl. Acad. Sci. USA 94, 12297-12302; WO2009067191; herein incorporated by reference in its entirety) with modifications as described herein. RNA pools, were generated from a mixture of eight DNA libraries. The libraries code for peptides with a fixed N-terminal Methionine residue, followed sequentially by a fixed Cysteine residue, eleven positions for amino acids, a Glycine-Serine-Glycine linker, and a C-terminal hexa-Histidine tag. In each of the eight libraries, one of the eleven positions from positions four through eleven is a fixed Cysteine residue. All twenty amino acids are allowed in the ten remaining positions in each of the eight libraries. Through this design, each of the libraries has two Cysteine residues flanking a random region comprised of three to eight residues followed by a second random region of two to seven residues. At the DNA level, the random positions with all twenty amino acids are made combinatorially with repeating codon units of NNS (N is A, G, C, and T; S is G and C) (Devlin, J. J., et. al., (1990). Science 249, 404-406.) To conduct the selection, one round of enrichment comprised the following steps: RNA pools containing a 3' terminal UV cross-linked oligonucleotide containing puromycin were translated with natural amino acids in rabbit reticulocyte lysates and the resulting peptides cyclized with dibromoxylene (J. Am. Chem. Soc. 127:1 1727 (2005)).

Direct selection of the peptides by target affinity was then performed. The RNA corresponding to the affinity selected peptides was reverse transcribed and PCR amplified to create a double-stranded DNA pool. The DNA pool was in vitro translated using T7 RNA polymerase to generate mRNA, and the mRNA produced was cross-linked as before at its 3' terminus with a puromycin-containing oligonucleotide. The mRNA-puromycin fusions were subjected to in vitro translation to generate the second round of the library, which is now enriched in peptides that bind plasma kallikrein. The selection cycle was repeated for six rounds. After the sixth round the DNA pool representing the selected peptides was cloned and sequenced, and the amino acid sequences of candidate kallikrein inhibitors were determined based on the DNA sequences. The peptide sequences identified are listed in Table 1.

TABLE 1

Kallikrein Binding Peptides

| Compound No. | Sequence | SEQ ID NO. |
|---|---|---|
| R2001 | MCNYWSPWTECSR | 1 |
| R2002 | MCESICRVLRYSE | 2 |

Example 7

Optimization of Kallikrein Inhibitors and Binding Sites

Kallikrein binding peptides were prepared by solid-phase synthesis, purified by RP-HPLC, and characterized for enzyme activity (Table 2).

TABLE 2

Kallikrein Inhibitory Activity of Synthetic Peptides

| Compound No. | Sequence | Cyclic | Avg. $IC_{50}$ (nM) | SEQ ID NO. |
|---|---|---|---|---|
| R2003 | [mXylyl(2,11)]MCNYWSPWTECSR-NH2 | Yes | 3.1 | 3 |
| R2004 | [mXylyl(2,6)]MCESICRVLRYSE-NH2 | Yes | 0.501 | 4 |

Peptides were optimized by making a variety of truncations, deletions, and substitutions. Each derivative was synthesized according to the methods of Examples 12 through 14. Each derivative was tested for inhibition of plasma kallikrein as described in Example 4. Derivatives of peptide R2004 are listed in Table 3 with their corresponding $IC_{50}$ values. Derivatives of peptide R2003 are listed in Table 4 with their corresponding $IC_{50}$ values.

TABLE 3

Kallikrein Inhibitory Activity

| Compound # | Sequence | Cyclic | Avg $IC_{50}$ (nM) | SEQ ID NO. |
|---|---|---|---|---|
| R2004 | [mXylyl(2,6)]MCESICRVLRYSE-NH2 | Yes | 0.501 | 4 |
| R2005 | [mXylyl(2,6)]MCETICRVLKYSD-NH2 | Yes | 1.8 | 5 |
| R2006 | [mXylyl(2,6)]MCESICRV-NH2 | Yes | 11.8 | 6 |
| R2007 | MCESICRV-NH2 | No | 2000 | 7 |
| R2008 | [mXylyl(2,6)]Ac-MCESICRV-NH2 | Yes | 10.2 | 8 |
| R2009 | [mXylyl(2,6)]Nvl-CESICRV-NH2 | Yes | 8.6 | 9 |
| R2010 | [mXylyl(2,6)]MCESICR-Tbg-NH2 | Yes | 9.9 | 10 |
| R2011 | [trans-butenyl(2,6)MCESICRV-NH2 | Yes | 12800 | 11 |
| R2012 | [mXylyl(2,6)]MCES-Phg-CRV-NH2 | Yes | 8.3 | 12 |
| R2013 | [mXylyl(2,6)]Nvl-CES-Phg-CR-Tbg-NH2 | Yes | 6.8 | 13 |
| R2014 | [mXylyl(2,6)]MCESICRVN-NH2 | Yes | 37.5 | 14 |
| R2015 | [mXylyl(2,6)]MCESICR-NH2 | Yes | 16500 | 15 |
| R2016 | [mXylyl(2,6)]MCESICRA-NH2 | Yes | 3900 | 16 |
| R2017 | [mXylyl(2,6)]MCESACRV-NH2 | Yes | 2140 | 17 |

TABLE 3-continued

Kallikrein Inhibitory Activity

| Compound # | Sequence | Cyclic | Avg IC$_{50}$ (nM) | SEQ ID NO. |
|---|---|---|---|---|
| R2018 | [mXylyl(2,6)]MCEAICRV-NH2 | Yes | 37.3 | 18 |
| R2019 | [mXylyl(2,6)]MCE-nMeS-ICRV-NH2 | Yes | 52.3 | 19 |
| R2020 | [mXylyl(2,6)]MC-Asp(T)-SICRV-NH2 | Yes | 13 | 20 |
| R2021 | [mXylyl(2,6)]Nvl-CESIC-Phe(4-CH2NH2)-V-NH2 | Yes | 2000 | 21 |
| R2022 | [mXylyl(2,6)]Nvl-CESIC-Phe(3-CH2NH2)-V-NH2 | Yes | 21000 | 22 |
| R2023 | [mXylyl(1,5)]Ac-CESICRV-NH2 | Yes | 19 | 23 |
| R2024 | [mXylyl(2,6)]MCASICRV-NH2 | Yes | 41.9 | 24 |
| R2025 | [mXylyl(2,6)]ACESICRV-NH2 | Yes | 9.5 | 25 |
| R2026 | [mXylyl(2,6)]MCES-nMeI-CRV-NH2 | Yes |  | 26 |
| R2027 | [mXylyl(2,6)]MC-nMeE-ESICRV-NH2 | Yes | 990 | 27 |
| R2028 | [hexyltetrazolyl-mXylyl(2,6)]MCESICRV-NH2 | Yes | 714 | 28 |
| R2029 | [mXylyl(2,6)]Nvl-CESIC-hLys-V-NH2 | Yes | 8840 | 29 |
| R2030 | [mXylyl(2,6)]Nvl-CEP-Phg-CR-Tbg-NH2 | Yes | 25 | 30 |
| R2031 | [mXylyl(2,6)]Nvl-Pen-ESICRV-NH2 | Yes | 1460 | 31 |
| R2032 | [mXylyl(2,6)]Nvl-CESI-Pen-RV-NH2 | Yes | 1030 | 32 |
| R2033 | [mXylyl(2,6)]Ac-Nvl-CESIC-hLys-V-NH2 | Yes | 8650 | 33 |
| R2034 | [mXylyl(2,6)]Nvl-Pen-ESI-Pen-RV-NH2 | Yes | >100000 | 34 |
| R2035 | [mXylyl(2,6)]Nvl-CESICRF-NH2 | Yes | 7200 | 35 |
| R2036 | [mXylyl(1,5)]Ac-CAS-Phg-CR-Tbg-NH2 | Yes | 6.4 | 36 |
| R2037 | [mXylyl(1,4)]Ac-CSICRV-NH2 | Yes | 410 | 37 |
| R2038 | [mXylyl(1,5)]Ac-CESICRVLK-NH2 | Yes | 299 | 38 |
| R2039 | [mXylyl(1,5)]CAS-Phg-CR-Tbg-NH2 | Yes | 11.9 | 39 |
| R2040 | [mXylyl(2,6)]MCESICKV-NH2 | Yes | 733 | 40 |
| R2041 | [mXylyl(1,5)]Heptanoyl-CESICRV-NH2 | Yes | 24.2 | 41 |
| R2042 | [oXylyl(2,6)]MCESICRV-NH2 | Yes | 3190 | 42 |
| R2043 | [pXylyl(2,6)]MCESICRV-NH2 | Yes | 617 | 43 |
| R2044 | [mLutidine(2,6)]MCESICRV-NH2 | Yes | 645 | 44 |
| R2045 | [mXylyl(1,5)]Ac-CESICRVL-NH2 | Yes | 187 | 45 |
| R2046 | [mXylyl(1,5)]Ac-CESICRVLR-NH2 | Yes | 59.3 | 46 |
| R2047 | [mXylyl(1,5)]Ac-C-a-SICRV-NH2 | Yes | 17.4 | 47 |
| R2048 | [mXylyl(1,5)]Ac-CAS-Tbg-CR-Tbg-NH2 | Yes | 1400 | 48 |
| R2049 | [mXylyl(1,3)](des-NH2)C-ICRV-NH2 | Yes | 16300 | 49 |
| R2050 | [mXylyl(2,6)]Ac-MCES-Chg-CRV-NH2 | Yes | 11 | 50 |
| R2051 | [mXylyl(1,5)](des-NH2)C-ESICRV-NH2 | Yes | 12.9 | 51 |
| R2052 | [mXylyl(1,5)]Ac-CA-Sar-Phg-CR-Tbg-NH2 | Yes | 74.2 | 52 |

TABLE 3-continued

Kallikrein Inhibitory Activity

| Compound # | Sequence | Cyclic | Avg IC$_{50}$ (nM) | SEQ ID NO. |
|---|---|---|---|---|
| R2053 | [mXyly1(1,5)]Ac-CAS-Phg-C-Phe(4-CH2NH2)-Tbg-NH2 | Yes | 5340 | 53 |
| R2054 | [mXyly1(2,6)]Ac-Nvl-CESIC-(η-ω-MeR)-V-NH2 | Yes | 5000 | 54 |
| R2055 | [mXyly1(1,5)]Ac-CESICRVLRY-NH2 | Yes | 2.2 | 55 |
| R2056 | [mXyly1(1,5)]Ac-CESICRVLRYS-NH2 | Yes | 1.9 | 56 |
| R2057 | [mXyly1(1,5)]Ac-CESICRVLRYSE-NH2 | Yes | 0.943 | 57 |
| R2058 | [mXyly1(1,5)]Ac-CAP-Phg-CR-Tbg-NH2 | Yes | 29.5 | 58 |
| R2059 | [mXyly1(1,5)]Ac-CASFCR-Tbg-NH2 | Yes | 425 | 59 |
| R2060 | [mXyly1(1,5)]Ac-C-a-S-(D)Phg-CR-Tbg-NH2 | Yes | 959 | 60 |
| R2061 | [mXyly1(1,5)]Ac-C-a-S-Phg-CR-Tbg-NH2 | Yes | 12.7 | 61 |
| R2062 | [mXyly1(1,5)]Ac-C-a-S-Cppg-CRV-NH2 | Yes | 2470 | 62 |
| R2063 | [mXyly1(1,5)]Ac-C-a-SVCRV-NH2 | Yes | 151 | 63 |
| R2064 | [mXyly1(1,5)](des-NH2)C-a-S-Phg-CR-Tbg-NH2 | Yes | 14.9 | 64 |
| R2065 | [mXyly1(1,5)]Ac-C-Nle-S-Phg-CR-Tbg-NH2 | Yes | 6.1 | 65 |
| R2066 | [mXyly1(1,5)]Heptanoyl-C-a-S-(D)Phg-C-R-Tbg-NH2 | Yes | 4370 | 66 |
| R2067 | [mXyly1(1,5)]Heptanoyl-C-a-S-Phg-C-R-Tbg-NH2 | Yes | 19.1 | 67 |
| R2068 | [mXyly1(1,5)]Heptanoyl-C-a-nMeS-Phg-C-R-Tbg-NH2 | Yes | 26.8 | 68 |
| R2069 | [mXyly1(1,5)]Heptanoyl-C-a-nMeS-(D)Phg-C-R-Tbg-NH2 | Yes | 903 | 69 |
| R2070 | [mXyly1(1,5)]Ac-C-a-S-Phg-CR-Cppg-NH2 | Yes | 118 | 70 |
| R2071 | [mXyly1(1,5)]Ac-C-a-S-Phg-CR-Chg-NH2 | Yes | 1920 | 71 |
| R2072 | [mXyly1(1,5)](des-NH2)C-AAICRV-NH2 | Yes | 13 | 72 |
| R2073 | [mXyly1(1,5)](des-NH2)C-OctG-S-Phg-CR-Tbg-NH2 | Yes | 18.6 | 73 |
| R2074 | [mXyly1(2,6)]MCESICR-nMeV-NH2 | Yes | 11600 | 74 |
| R2075 | [mXyly1(1,5)](des-NH2)C-AA-Phg-CR-Tbg-NH2 | Yes | 2.6 | 75 |
| R2076 | [mXyly1(1,5)](des-NH2)C-GA-Phg-CR-Tbg-NH2 | Yes | 11.4 | 76 |
| R2077 | [mXyly1(2,6)]MCES-Cpg-CRV-NH2 | Yes | 19.7 | 77 |
| R2078 | [mXyly1(1,5)](des-NH2)C-Aib-A-Phg-CR-Tbg-NH2 | Yes | 2.8 | 78 |
| R2079 | [mXyly1(1,5)](des-NH2)C-a-A-Phg-CR-Tbg-NH2 | Yes | 17.8 | 79 |
| R2080 | [mXyly1(1,5)](des-NH2)C-a-S-Phg-C-azaTrp-Tbg-NH2 | Yes | 13200 | 80 |

TABLE 3-continued

Kallikrein Inhibitory Activity

| Compound # | Sequence | Cyclic | Avg IC$_{50}$ (nM) | SEQ ID NO. |
|---|---|---|---|---|
| R2081 | [mXylyl(1,5)](des-NH2)C-Tranexamic-(D)Phg-CR-Tbg-NH2 | Yes | >10,000 | 81 |
| R2082 | [mXylyl(1,5)](des-NH2)C-a-S-Chg-C-R-Tbg-NH2 | Yes | 25.8 | 82 |
| R2083 | [oXylyl(1,5)](des-NH2)C-Phg-CR-Tbg-NH2 | Yes | >8900 | 83 |
| R2084 | [pXylyl(1,5)]des-NH2)C-Phg-CR-Tbg-NH2 | Yes | 1800 | 84 |
| R2085 | [mXylyl(1,5)]CESICRV-NH2 | Yes | 21.9 | 85 |
| R2086 | [mXylyl(2,6)]MCESICRELRYSE-NH2 | Yes | 8930 | 86 |
| R2087 | [mXylyl(2,6)]MCESICRE-NH2 | Yes | >16600 | 87 |
| R2088 | [mXylyl(2,6)]MCESNCRV-NH2 | Yes | 2040 | 88 |
| R2089 | [mXylyl(2,6)]MCEYICRV-NH2 | Yes | 61.9 | 89 |
| R2090 | [mXylyl(1,5)](des-NH2)C-Tranexamic-Phg-CR-Tbg-NH2 | Yes | 1750 | 90 |
| R2091 | [mXylyl(1,5)](des-NH2)C-Aib-A-Chg-CR-Tbg-NH2 | Yes | 3.2 | 91 |
| R2092 | [mXylyl(1,5)](des-NH2)C-Acc-A-(D)Phg-CR-Tbg-NH2 | Yes | 3960 | 92 |
| R2093 | [mXylyl(1,5)](des-NH2)C-Acc-A-Phg-CR-Tbg-NH2 | Yes | 10.3 | 93 |
| R2094 | [mXylyl(1,5)](des-NH2)C-AcPyr-A-(D)Phg-CR-Tbg-NH2 | Yes | 46.9 | 94 |
| R2095 | [mXylyl(1,5)](des-NH2)C-AcPyr-A-Phg-CR-Tbg-NH2 | Yes | 1.6 | 95 |
| R2096 | [mXylyl(1,5)](des-NH2)C-Acbc-A-(D)Phg-CR-Tbg-NH2 | Yes | 748 | 96 |
| R2097 | [mXylyl(1,5)](des-NH2)C-Acbc-A-Phg-CR-Tbg-NH2 | Yes | 2 | 97 |
| R2098 | [mXylyl(1,5)](des-NH2)C-Aib-A-(D)Phg-CR-Tbg-LRYSE-NH2 | Yes | 22.4 | 98 |
| R2099 | [mXylyl(1,5)](des-NH2)C-Aib-A-Phg-CR-Tbg-LRYSE-NH2 | Yes | 0.1 | 99 |
| R2100 | [mXylyl(1,5)](des-NH2)C-AcPyr-A-Chg-CR-Tbg-NH2 | Yes | 1.5 | 100 |
| R2101 | [mXylyl(2,6)]MCESI-nMeC-RV-NH2 | Yes | 12700 | 101 |
| R2102 | [3-methoxy-mXylyl(2,6)]MCESICRV-NH2 | Yes | 39.7 | 102 |

TABLE 4

Kallikrein Inhibitory Activity

| Compound # | Sequence | Cyclic | Avg IC$_{50}$ (nM) | SEQ ID NO. |
|---|---|---|---|---|
| R2003 | [mXylyl(2,11)]MCNYWSPWTECSR-NH2 | Yes | 3.1 | 3 |
| R2103 | MCNYWSPWTECSR-NH2 | No | 2.3 | 103 |

TABLE 4-continued

Kallikrein Inhibitory Activity

| Compound # | Sequence | Cyclic | Avg IC$_{50}$ (nM) | SEQ ID NO. |
|---|---|---|---|---|
| R2104 | MCNYWSPWTECSA-NH2 | No | 3.4 | 104 |
| R2105 | MCNYWSPWTSEIC-NH2 | No | 4.4 | 105 |
| R2106 | Ac-NYWSPWT-NH2 | No | 374 | 106 |
| R2107 | MSNYWSPWTESSA-NH2 | No | 128 | 107 |
| R2108 | [mXylyl(2,11)]MCNYWSPWTECSA-NH2 | Yes | 4.1 | 108 |
| 82109 | [mXylyl(2,13)]MCNYWSPWTSEIC-NH2 | Yes | 9.2 | 109 |
| R2110 | MCNYWSPWTECS-NH2 | No | 3.5 | 110 |
| R2111 | MCNYWSPWTEC-NH2 | No | 3.8 | 111 |
| R2112 | MCNYWSPWTE-NH2 | No | 2.4 | 112 |
| R2113 | MCNYWSPWT-NH2 | No | 88.8 | 113 |
| R2114 | MCNYWSPW-NH2 | No | 349 | 114 |
| R2115 | MCNYWSP-NH2 | No | >17300 | 115 |
| R2116 | Ac-CNYWSPWTECSA-NH2 | No | 3.5 | 116 |
| R2117 | Ac-NYWSPWTECSA-NH2 | No | 43.9 | 117 |
| R2118 | Ac-YWSPWTECSA-NH2 | No | >100000 | 118 |
| R2119 | Ac-WSPWTECSA-NH2 | No | >100000 | 119 |
| R2120 | Ac-SPWTECSA-NH2 | No | >100000 | 120 |
| R2121 | Ac-PWTECSA-NH2 | No | 10300 | 121 |
| R2122 | MCNYWSPWTSEI-NH2 | No | 30.4 | 122 |
| R2123 | MCNYWSPWTSE-NH2 | No | 25.5 | 123 |
| R2124 | MCNYWSPWTS-NH2 | No | 54.6 | 124 |
| R2125 | [mXylyl(1,10)]Ac-CNYWSPWTECSA-NH2 | Yes | 10.6 | 125 |
| R2126 | Ac-CNYWSPWTEC-NH2 | No | 1.4 | 126 |
| R2127 | Ac-CNYWSPWTEA-NH2 | No | 35.6 | 127 |
| R2128 | Ac-CNYWSPWTAC-NH2 | No | 2.5 | 128 |
| R2129 | Ac-CNYWSPWAEC-NH2 | No | 12.3 | 129 |
| R2130 | Ac-CNYWSPATEC-NH2 | No | 5300 | 130 |
| R2131 | Ac-CNYWAPWTEC-NH2 | No | 127 | 131 |
| R2132 | Ac-CNYASPWTEC-NH2 | No | 4110 | 132 |
| R2133 | Ac-CNAWSPWTEC-NH2 | No | 39.1 | 133 |
| R2134 | Ac-CNYWSPWTC-NH2 | No | 86.7 | 134 |
| R2135 | Ac-CNYWSPWT-NH2 | No | 144 | 135 |
| R2136 | [mXylyl(1,10)]Ac-CNYWSPWTAC-NH2 | Yes | 6.1 | 136 |
| R2137 | Ac-CNYWSAWTEC-NH2 | No | 57.2 | 137 |
| R2138 | Ac-ANYWSPWTEC-NH2 | No | 22.3 | 138 |

TABLE 4-continued

Kallikrein Inhibitory Activity

| Compound # | Sequence | Cyclic | Avg IC$_{50}$ (nM) | SEQ ID NO. |
|---|---|---|---|---|
| R2139 | Ac-Nvl-NYWSPWTAC-NH2 | No | 65.3 | 139 |
| R2140 | Ac-CNYWSPWTA-Nvl-NH2 | No | 105 | 140 |
| R2141 | Ac-Nvl-NYWSPWTA-Nvl-NH2 | No | 157 | 141 |
| R2142 | [cyclo(1,10)]Ac-CNYWSPWTAC-NH2 | Yes | 2.7 | 142 |
| R2143 | Ac-ANYWSPWTAC-NH2 | No | 48.4 | 143 |
| R2144 | Ac-CNYWSPWTAA-NH2 | No | 95.5 | 144 |
| R2145 | Ac-ANYWSPWTAA-NH2 | No | 58.8 | 145 |
| R2146 | Ac-CNYWSPWAAC-NH2 | No | 17.5 | 146 |

Additional optimization was carried out by making a variety of truncations, deletions, and substitutions. Each derivative was synthesized according to the methods of Examples 12 through 14. Each derivative was tested for inhibition of plasma kallikrein as described in Example 4.

Additional derivatives of peptide R2004 are listed in Table 5 with their corresponding IC$_{50}$ values. Additional derivatives of peptide R2003 are listed in Table 6 with their corresponding IC$_{50}$ values.

TABLE 5

Additional optimized derivatives of R2004

| Compound No. | Sequence | Cyclic | Avg. IC$_{50}$ (nM) | SEQ ID NO. |
|---|---|---|---|---|
| R2147 | [mXylyl(1,5)](des-NH2)C-AcPyr-A-Chg-C-AzaTrp-Tbg-NH2 | Yes | >2190 | 147 |
| R2148 | [mXylyl(1,5)]heptanoyl-C-a-nMeS-Chg-CR-Tbg-NH2 | Yes | 28.8 | 148 |
| R2149 | [mXylyl(1,5)](des-NH2)C-(Cyclo-L)-A-(D)Phg-CRTbg-NH2 | Yes | 177 | 149 |
| R2150 | [mXylyl(1,5)](des-NH2)C-(Cyclo-L)-A-Phg-CRTbg-NH2 | Yes | 0.764 | 150 |
| R2151 | [mXylyl(1,4)](des-NH2)C-AEA-Phg-CR-Tbg-NH2 | Yes | 1940 | 151 |
| R2152 | [mXylyl(1,5)](des-NH2)C-Aib-A-Chg-CR-(3,3-dimethylbutan-2-amine) | Yes | 319 | 152 |
| R2153 | [mXylyl(1,5)](des-NH2)C-Aib-A-Chg-CR-OH | Yes | >8880 | 153 |
| R2154 | [mXylyl(1,4)](2-SAc)-SlCRV-NH2 | Yes | >7930 | 154 |
| R2155 | [mXylyl(1,4)](des-NH2)C-SlCRV-NH2 | Yes | 66.3 | 155 |
| R2156 | [pXylyl(1,4)](des-NH2)C-SlCRV-NH2 | Yes | 1,530 | 156 |
| R2157 | [1,3,5-Xylyl(1,5,9)(des-NH2)C-Aib-A-Chg-CR-Tbg-PC-NH2 | Yes | >14,300 | 157 |
| R2158 | [1,3,5-Xylyl(1,5,11)](des-NH2)C-Aib-A-Chg-CR-Tbg-LRYC-NH2 | Yes | 2,340 | 158 |
| R2159 | [mXylyl(2,6)]Ac-Chg-CR-V-AC-NH2 | Yes | >20100 | 159 |
| R2160 | [mXylyl(2,6)]Ac-Chg-CR-V-PC-NH2 | Yes | >100000 | 160 |
| R2161 | [oXylyl(1,4)](Des-NH2)C-SlCRV-NH2 | Yes | 2230 | 161 |

TABLE 5-continued

Additional optimized derivatives of R2004

| Compound No. | Sequence | Cyclic | Avg. IC$_{50}$ (nM) | SEQ ID NO. |
|---|---|---|---|---|
| R2162 | [mXylyl(1,5)](des-NH2)C-Aib-A-Chg-CR-(2-amino-3,3-dimethylbutan-1-ol) | Yes | 466 | 162 |
| R2163 | [mXylyl(2,6)]MCESIC-nMeR-V-NH2 | Yes | 1960 | 163 |
| R2164 | [mXylyl(1,4)](des-NH2)C-S-Chg-CR-Tbg-NH2 | Yes | 10.1 | 164 |
| R2165 | [mXylyl(1,4)](Des-NH2)C-nMeS-Chg-CR-Tbg-NH2 | Yes | 82.1 | 165 |
| R2166 | [mXylyl(1,5)](des-NH2)C-AcPyr-A-Chg-C-(4-BZA)-V-NH2 | Yes | 310 | 166 |
| R2167 | [mXylyl(1,4)](des-NH2)C-P-Chg-CR-Tbg-NH2 | Yes | 10.7 | 167 |
| R2168 | [mXylyl(1,4)](Des-NH2)C-(Cyclo-L)-Chg-CR-Tbg-NH2 | Yes | 11.3 | 168 |
| R2169 | [mXylyl(1,5)](des-NH2)C-(Cyclo-L)-A-Chg-CR-Tbg-NH2 | Yes | 1.9 | 169 |
| R2170 | [mXylyl(1,5)](des-NH2)C-(Cyclo-L)-A-Chg-CR-Tbg-LRY-NH2 | Yes | 2.1 | 170 |
| R2171 | [mXylyl(1,5)](des-NH2)C-ESIC-r-V-NH2 | Yes | >100,000 | 171 |
| R2172 | [mXylyl(1,5)](des-NH2)C-ESIC-Orn-V-NH2 | Yes | >100,000 | 172 |
| R2173 | [cyclo(1,5)]-ACP-Aib-A-Chg-DR-Tbg-NH2 | Yes | >100,000 | 173 |
| R2174 | [mXylyl(1,4)](des-NH2)C-(Cyclo-L)-Chg-CK-Tbg-NH2 | Yes | 870 | 174 |
| R2175 | [mXylyl(1,5)](des-NH2)C-(Cyclo-L)-A-Chg-CR-V-OH | Yes | 379 | 175 |
| R2176 | [mXylyl(1,4)](des-NH2)C-Aib-Chg-CR-Tbg-NH2 | Yes | 15.2 | 176 |
| R2177 | [mXylyl(1,4)](des-NH2)C-Acc-Chg-CR-Tbg-NH2 | Yes | 34.1 | 177 |
| R2178 | [mXylyl(1,5)](des-NH2)C-(Cyclo-L)-A-Chg-CR-V-NHCH3 | Yes | 3.2 | 178 |
| R2179 | [mXylyl(1,5)](des-NH2)C-AcPyr-A-Chg-C-(3-BZA)-V-NH2 | Yes | >8230 | 179 |
| R2180 | [mXylyl(1,4)](des-NH2)C-(a-Me)P-Chg-CR-Tbg-NH2 | Yes | 6.8 | 180 |
| R2181 | [mXylyl(1,4)](des-NH2)C-Acbc-Chg-CR-Tbg-NH2 | Yes | 18.5 | 181 |
| R2182 | [mXylyl(1,4)](des-NH2)C-AcPyr-Chg-CR-Tbg-NH2 | Yes | 13.5 | 182 |
| R2183 | [mXylyl(1,4)](des-NH2)C-P-Chg-CR-V-OH | Yes | >3500 | 183 |
| R2184 | [mXylyl(1,4)](des-NH2)C-P-Chg-CR-V-NHCH3 | Yes | 15.7 | 184 |
| R2185 | [mXylyl(1,5)](des-NH2)C-AcPyr-A-Chg-C-(4-BZA-N-hexylcarbamate)-V-NH2 | Yes | >100,000 | 185 |

TABLE 5-continued

Additional optimized derivatives of R2004

| Compound No. | Sequence | Cyclic | Avg. IC$_{50}$ (nM) | SEQ ID NO. |
|---|---|---|---|---|
| R2186 | [mXylyl(1,4)](des-NH2)C-P-Chg-C-R(N-ω hexylcarbamate)-Tbg-NH2 | Yes | >100,000 | 186 |
| R2187 | [mXylyl(1,4)](des-NH2)C-P-(D)Phg-CR-Tbg-NH2 | Yes | >4700 | 187 |
| R2188 | [mXylyl(1,4)](des-NH2)C-P-Phg-CR-Tbg-NH2 | Yes | 3.4 | 188 |
| R2189 | [mXylyl(1,4)](des-NH2)C-P-(2-OMe)Phg-CR-Tbg-NH2 | Yes | 39.8 | 189 |
| R2190 | [mXylyl(1,5)](des-NH2)C-Aib-A-Chg-CR-Tbg-LRYSE-NH2 | Yes | 0.511 | 190 |
| R2191 | [mXylyl(1,5)](des-NH2)C-Aib-A-Chg-CR-Tbg-LRYSE(PEG40K)-NH2 | Yes | 5.5 | 191 |
| R2192 | [mXylyl(1,4)](des-NH2)C-P-(α-Me)Phg-CR-Tbg-NH2 | Yes | 851 | 192 |
| R2193 | [mXylyl(2,6)](BODIPY-TMR)-MCESICRV-NH2 | Yes | 205 | 193 |
| R2194 | [mXylyl(1,4)](des-NH2)C-Aze-Chg-CR-Tbg-NH2 | Yes | 127 | 194 |
| R2195 | [mXylyl(1,4)](des-NH2)C-P-Chg-CR-OH | Yes | >175000 | 195 |
| R2196 | [mXylyl(1,4)](des-NH2)C-P-Chg-CR-(S)-2,2-dimethyl-1-(pyridin-2-yl)propan-1-amine | Yes | 35.6 | 196 |
| R2197 | [mXylyl(1,4)](des-NH2)C-P-Chg-CR-2-methyl-1-(4H-1,2,4-triazol-3-yl)propan-1-amine | Yes | 56.9 | 197 |
| R2198 | [mXylyl(1,4)](Des-NH2)C-P-Chg-C-(2-APY-Tbg-NH2 | Yes | >15,000 | 198 |
| R2199 | [mXylyl(1,4)](des-NH2)C-(α-Me)Pro-Phg-CR-Tbg-NH2 | Yes | 0.54 | 199 |
| R2200 | [mXylyl(1,4)](des-NH2)C-(α-Me)Pro-(D-Phg)-CR-Tbg-NH2 | Yes | 470 | 200 |
| R2201 | [mXylyl(1,4)](des-NH2)C-E-Chg-CR-Tbg-NH2 | Yes | 7 | 201 |
| R2202 | [mXylyl(1,4)](des-NH2)C-P-Phg-CR-Tbg-L-OH | Yes | 58.8 | 202 |
| R2203 | [mXylyl(1,4)](des-NH2)C-P-Chg-C-2-amino-4-(6-aminopyridin-3-yl)butanoic acid-V-NH2 | Yes | >10000 | 203 |
| R2204 | [mXylyl(1,4)](des-NH2)C-Ser-(nMe)Ile-CR-Tbg-NH2 | Yes | >25,000 | 204 |
| R2205 | [mXylyl(1,4)](des-NH2)C-P-Phg-C-4-Cl-Phe-Tbg-NH2 | Yes | >75000 | 205 |
| R2206 | [mXylyl(1,4)](des-NH2)C-P-(D)Phg-C-4-Cl-Phe-Tbg-NH2 | Yes | >75000 | 206 |
| R2207 | [mXylyl(1,4)](des-NH2)C-P-Phg-C-3-Cl-Phe-Tbg-NH2 | Yes | >75000 | 207 |
| R2208 | [mXylyl(1,4)](des-NH2)C-P-(D-Phg)-C-3-Cl-Phe-Tbg-NH2 | Yes | >75000 | 208 |
| R2209 | [mXylyl(1,4)](des-NH2)C-P-Phg-C-5-Cl-Trp-Tbg-NH2 | Yes | >75000 | 209 |

TABLE 5-continued

Additional optimized derivatives of R2004

| Compound No. | Sequence | Cyclic | Avg. IC$_{50}$ (nM) | SEQ ID NO. |
|---|---|---|---|---|
| R2210 | [mXylyl(1,4)](des-NH2)C-P-(D-Phg)-C-5-Cl-Trp-Tbg-NH2 | Yes | >75000 | 210 |
| R2211 | [mXylyl(1,4)](des-NH2)C-P-Phg-C-Dab-Tbg-NH2 | Yes | >75000 | 211 |
| R2212 | [mXylyl(1,4)](des-NH2)C-P-(D-Phg)-C-Dab-Tbg-NH2 | Yes | >100000 | 212 |
| R2213 | [mXylyl(1,4)](des-NH2)C-E(PEG40K)-Chg-CR-Tbg-NH2 | Yes | 461.6 | 213 |
| R2214 | [mXylyl(1,4)](des-NH2)Cys-P-Chg-CR-Tbg-OH | Yes | 4000 | 214 |
| R2215 | [mXylyl(1,4)](Des-NH2)C-P-Phg-C-(4-amidino)Phe-V-NH2 | Yes | 6386 | 215 |
| R2216 | [mXylyl(1,4)](des-NH2)C-P-Phg-CR-Tbg-L-nMeR-YSE-NH2 | Yes | 0.913 | 216 |
| R2217 | [mXylyl(1,4)](des-NH2)C-P-(D-Phg)-CR-Tbg-L-nMeR-YSE-NH2 | Yes | 114.1 | 217 |
| R2218 | [mXylyl(1,4)](des-NH2)C-P-Ind-CR-Tbg-NH2 | Yes | 3 | 218 |
| R2219 | [mXylyl(1,4)](des-NH2)C-P-Phg-C-ABP-Tbg-NH2 | Yes | >100000 | 219 |
| R2220 | [mXylyl(1,4)](des-NH2)C-P-(D-Phg)-C-ABP-Tbg-NH2 | Yes | >100000 | 220 |
| R2221 | [mXylyl(1,4)](des-NH2)C-P-Phg-C-(4-(aminomethyl)benzimidamide | Yes | 400.6 | 221 |

TABLE 6

Additional optimized derivatives of R2003

| Compound No. | Sequence | Cyclic | Avg. IC$_{50}$ (nM) | SEQ ID NO. |
|---|---|---|---|---|
| R2222 | [Cyclo(1,10)]CNYWSPWTAA | Yes | 926 | 222 |
| R2223 | [mXylyl(1,10)]Ac-CN-nMeY-W-nMeS-PW-nMeT-AC-NH2 | Yes | >100,000 | 223 |
| R2224 | [cyclo(1,10)]Ac-CN-nMeY-W-nMeS-PW-nMeT-AC-NH2 | Yes | >100,000 | 224 |
| R2225 | Ac-CNYWSPWTAc-NH2 | No | 8.1 | 225 |
| R2226 | Ac-CNYWSPWTaC-NH2 | No | 222 | 226 |
| R2227 | Ac-CNYWSPWtAC-NH2 | No | 323 | 227 |
| R2228 | Ac-CNYWSPwTAC-NH2 | No | >10,600 | 228 |
| R2229 | Ac-CNYWSpWTAC-NH2 | No | >14,300 | 229 |
| R2230 | Ac-CNYWsPWTAC-NH2 | No | >6,580 | 230 |
| R2231 | Ac-CNYwSPWTAC-NH2 | No | 760 | 231 |
| R2232 | Ac-CNyWSPWTAC-NH2 | No | >1,950 | 232 |
| R2233 | Ac-CnYWSPWTAC-NH2 | No | 305 | 233 |
| R2234 | Ac-CNYWSPWT-nMeA-C-NH2 | No | 2.7 | 234 |

TABLE 6-continued

Additional optimized derivatives of R2003

| Compound No. | Sequence | Cyclic | Avg. IC$_{50}$ (nM) | SEQ ID NO. |
|---|---|---|---|---|
| R2235 | Ac-CNYWSPW-nMeT-AC-NH2 | No | 101 | 235 |
| R2236 | Ac-CNYWSP-nMeW-TAC-NH2 | No | >4900 | 236 |
| R2237 | Ac-CNYW-nMeS-PWTAC-NH2 | No | >13900 | 237 |
| R2238 | Ac-CNY-nMeW-SPWTAC-NH2 | No | >4520 | 238 |
| R2239 | Ac-CN-nMeY-WSPWTAC-NH2 | No | >12,500 | 239 |

As used herein, abbreviations have the following meaning: "Nvl" stands for Norvaline; "Phg" stands for phenylglycine; "Tbg" stands for tert-butylglycine; "nMe" indicates the N-methylated form of a given amino acid (e.g. nMeS or nMeSer is the N-methylated form of serine); "Asp(T)" stands for (S)-2-amino-3-(2H-tetrazol-5-yl)propanoic acid; "Phe(4-CH2NH2)" stands for 4-aminomethyl-phenylalanine; "Phe(3-CH2NH2)" stands for 3-aminomethyl-phenylalanine; "Cpg" stands for cyclopentylglycine; "hLys" stands for homolysine; "Pen" stands for penicillamine; one letter abbreviations for amino acids that appear in lower case indicate that the D-isomer of that amino acid is present (e.g. "a" stands for D-alanine); "Chg" stands for cyclohexylglycine; "Sar" stands for sarcosine; "η-ω-MeR" or "η-ω-Me-Arg" stands for the eta-omega methylated form of arginine; "Cppg" stands for cyclopropylyglycine; "(D)Phg" stands for D-phenylglycine; "OctG" stands for octylglycine; "Nle" stands for norleucine; "Aib" stands for aminoisobutyric acid; "azaTrp" stands for aza-tryptophan; "Tranexamic" stands for tranexamic acid; "Acc" stands for 1-aminocyclopropanecarboxylic acid; "AcPyr" or "Ac-pyr" stands for 4-aminotetrahydro-2H-pyran-4-carboxylic acid; "Acbc" stands for 1-aminocyclobutanecarboxylic acid; "(2-OMe) Phg" stands for 2-methoxy-phenylglycine; "(a-Me)P" stands for alpha methyl proline; "(a-Me)Phg" stands for alpha methyl phenylglycine; "(BODIPY-TMR)" stands for 6-((4, 4-difluoro-1,3-dimethyl-5-(4-methoxyphenyl)-4-bora-3a, 4a-diaza-s-indacene-2-propionyl)amino)hexanoic acid; "2APY" stands for 2-amino-4-(2-aminopyridin-4-yl)butanoic acid; "2-SAc" stands for 2-thioacetic acid; "3-Cl-Phe" stands for 3-chlorophenylalanine; "3-Cl-Tyr" stands for 3-chlorotyrosine; "3-F-Tyr" stands for 3-fluorotyrosine; "4-BZA" stands for 2-amino-3-(4-carbamimidoylphenyl) propanoic acid; "4-Cl-Phe" stands for 4-chlorophenylalanine; "4-F-Phe" stands for 4-fluorophenylalanine; "5-Cl-Trp" stands for 5-chlorotryptophan; "5-F-Trp" stands for 5-fluorotryptophan; "ABP" stands for 2-amino-3-(5-bromothiophen-2-yl)propanoic acid; "Achc" stands for 1-aminocyclohexanecarboxylic acid; "AEA" stands for 2-(2-aminoethoxy)acetic acid; "AzaTrp" stands for 7-azatryptophan; "azaTrp" stands for aza-tryptophan; "Aze" stands for Azetidine; "Cpg" stands for cyclopentylglycine; "(Cyclo-L)" stands for 1-aminocyclopentanecarboxylic acid; "Dab" stands for (S)-4-diaminobutyric acid; "homoCys" stands for homocysteine; "Ind" stands for (S)-2-amino-2-(2,3-dihydro-1H-inden-2-yl)acetic acid; "Orn" stands for Ornithine; "PEG40K" stands for poly ethylene glycol, 40,000 kD in size; "des-NH2" represents a missing amino-terminal amine group; "mLutidine" stands for meta-lutidine; "Ac" stands for acetyl; "NH2" stands for amine; "Heptanoyl" refers to an acyl chain comprised of 7 carbon atoms; "[mXylyl(x,y)]" refers to the dibromoxylene linker between the cysteines and the numerical identifiers, x and y, place the position of the cysteines participating in the cyclization; "oXylyl" stands for ortho-xylyl; "pXylyl" stands for para-xylyl; and "[cyclo (x,y)]" refers to the disulfide bond between two cysteines (to form a cyclic loop) and the numerical identifiers, x and y, place the position of the cysteines participating in the cyclization. All other symbols refer to the standard one-letter amino acid code.

Example 8

Inhibitor Specificity

To determine the specificity of peptide inhibitors, an IC$_{50}$ assay, as described in Example 4, was performed on a variety of serine proteases related to human plasma kallikrein. The enzymes tested include mouse plasma kallikrein (R&D Systems, Minneapolis, Minn.), and the human enzymes Factor VIIa (Enzyme Research Laboratories, South Bend, Ind.), Factor Xa (Enzyme Research Laboratories, South Bend, Ind.), Factor XIa (Enzyme Research Laboratories, South Bend, Ind.), Factor XIIa (Enzyme Research Laboratories, South Bend, Ind.), tissue kallikrein KLK13 (R&D Systems, Minneapolis, Minn.), thrombin (Enzyme Research Laboratories, South Bend, Ind.) and plasmin (Enzyme Research Laboratories, South Bend, Ind.).

Each enzyme was tested with the following specific fluorogenic substrates (available from Bachem; Torrance, Calif.): mouse plasma kallikrein (Pro-Phe-Arg-AMC), Factor VIIa (Boc-Val-Pro-Arg-AMC), Factor Xa (Boc-Gln-Gly-Arg-AMC), Factor XIa (Boc-Gln-Gly-Arg-AMC), Factor XIIa (Boc-Gln-Gly-Arg-AMC), KLK13 (Boc-Val-Pro-Arg-AMC), thrombin (Boc-Val-Pro-Arg-AMC) and plasmin (Boc-Val-Leu-Lys-AMC). Peptide inhibitors R2006, R2010, R2012, R2019, R2023, R2030, R2036, R2041, R2047, R2104 and R2051 were assayed. As compared to human and mouse plasma kallikreins, for which the inhibitors exhibited IC$_{50}$ values ranging from 3.4 to 191 nM, none of the inhibitors had an IC$_{50}$ value below 4.8 μM and the majority were above 100 μM. Thus, all of the inhibitors tested were found to be highly selective for human and mouse plasma kallikreins (Tables 7 and 8).

TABLE 7

Inhibitor Specificity

| Peptide | SEQ ID NO | Human Kallikrein IC$_{50}$ (nM) | Mouse Kallikrein IC$_{50}$ (nM) | Factor VIIa IC$_{50}$ (nM) | Factor Xa IC$_{50}$ (nM) | Factor XIa IC$_{50}$ (nM) |
|---|---|---|---|---|---|---|
| R2006 | 6 | 25 | 42 | >100,000 | >7,000 | >11,600 |
| R2010 | 10 | 9.9 | 38.8 | >100,000 | >100,000 | >15,000 |

TABLE 7-continued

Inhibitor Specificity

| Peptide | SEQ ID NO | Human Kallikrein IC$_{50}$ (nM) | Mouse Kallikrein IC$_{50}$ (nM) | Factor VIIa IC$_{50}$ (nM) | Factor Xa IC$_{50}$ (nM) | Factor XIa IC$_{50}$ (nM) |
|---|---|---|---|---|---|---|
| R2012 | 12 | 8.3 | 11.3 | NT | NT | >8,300 |
| R2019 | 19 | 52.3 | 85.6 | >100,000 | >10,000 | >9,100 |
| R2023 | 23 | 19 | 47.3 | >100,000 | >7,000 | >12,100 |
| R2030 | 30 | 25 | 63.9 | >100,000 | >100,000 | >10,400 |
| R2036 | 36 | 6.4 | 12.8 | >100,000 | >7,000 | >4,800 |
| R2041 | 41 | 24.2 | 191 | >17,900 | >7,000 | >5,400 |
| R2047 | 47 | 32.3 | 36.7 | >100,000 | >100,000 | >13,800 |
| R2104 | 104 | 3.4 | 11.2 | >100,000 | >100,000 | >5,000 |
| R2051 | 51 | 12.9 | 19.3 | >100,000 | >100,000 | >8,300 |

TABLE 8

Inhibitor Specificity (continued)

| Peptide | SEQ ID NO | Factor XIIa IC$_{50}$ (nM) | KLK13 IC$_{50}$ (nM) | Thrombin IC$_{50}$ (nM) | Plasmin IC$_{50}$ (nM) |
|---|---|---|---|---|---|
| R2006 | 6 | >100,000 | >100,000 | >100,000 | >100,000 |
| R2010 | 10 | >100,000 | >100,000 | >100,000 | >100,000 |
| R2012 | 12 | NT | >100,000 | NT | NT |
| R2019 | 19 | >12,500 | >16,400 | >100,000 | >21,000 |
| R2023 | 23 | >100,000 | >100,000 | >100,000 | >100,000 |
| R2030 | 30 | >100,000 | >100,000 | >100,000 | >100,000 |
| R2036 | 36 | >100,000 | >100,000 | >100,000 | >19,500 |
| R2041 | 41 | >100,000 | >100,000 | >100,000 | >100,000 |
| R2047 | 47 | >100,000 | >100,000 | >100,000 | >100,000 |
| R2104 | 104 | >100,000 | >100,000 | >100,000 | 5,800 |
| R2051 | 51 | >100,000 | >100,000 | >100,000 | >100,000 |

Example 9

Carrageenan-Induced Paw Edema Animal Model

The carrageenan-induced paw edema model is an art accepted animal model for the study of the compositions of the present invention. In this model, animals are administered carrageenan and the subsequent paw swelling is quantified by methods described by Morris (2003, Carrageenan-Induced Paw Edema in the Rat and Mouse. Methods in Mol. Biology 225, 115-121). The resulting paw swelling is compared to swelling after the effects of administration of any of the kallikrein inhibitors disclosed herein. Active kallikrein inhibitors are those that evince less paw swelling than that induced by carrageenan.

Example 10

Diabetic Macular Edema Animal Models

Diabetic macular edema (DME) is the thickening of the retina in the macular area due to diabetic retinopathy (DR). Patients with advance DR have abnormally abundant ocular levels of proteins of the plasma kallikrein-kinin system. Animals are administered the kallikrein inhibitors disclosed in Tables 1-6 and 9 to study the effect of the inhibitors for the treatment of DME. The animal models include animals that have diabetes, oxygen-induced retinopathy (OIR) and/ or both disorders. Diabetes is induced when the animals are given an injection of streptozotocin and OIR is induced by exposing neonatal animals to hyperoxia as described (Zhang et al, 2004, Plasminogen kringle 5 reduces vascular leakage in the retina in rat models of oxygen-induced retinopathy and diabetes. Diabetologia 47:124-131; Smith et al, 1994, Oxygen-induced retinopathy in the mouse. Invest Ophthalmol Vis Sci 35:101-111).

The vascular permeability of the retina and iris is determined by measuring the albumin leakage from blood vessels into the retina and iris using Evans blue as described (Zhang et al, 2004, Plasminogen kringle 5 reduces vascular leakage in the retina in rat models of oxygen-induced retinopathy and diabetes. Diabetologia 47:124-131; Gao et al, 2003, Kallikrein-binding protein inhibits retinal neovascularization and decreases vascular leakage, Diabetologia 46:689-698). The dosage of kallikrein inhibitors administered to the animals is varied to study the dose-dependent effects on vascular permeability.

Example 11

Animal Models Using C1INH Knockout Mice

Mice in which the C1INH gene was targeted by gene trapping (C1INH−/− mice) are used to study the effect of the kallikrein inhibitors disclosed in Tables 1-6 and 9 on vascular permeability. The mice may have diabetes induced from an injection of streptozotocin and/or oxygen-induced retinopathy (OIR) induced by exposing neonatal mice to hyperoxia. To determine the effects on vascular permeability from the administration kallikrein inhibitors described herein, Evans blue dye is injected into the mice after the administration of the kallikrein inhibitor. The mice are administered the kallikrein inhibitor in a single dose administration or a dose-dependent administration study. The kallikrein inhibitor is administered intravenously, subcutaneously or intramuscularly.

Example 12

Peptide Synthesis

Peptides were synthesized using standard solid-phase Fmoc/tBu methods. The synthesis is typically performed on a Liberty automated microwave peptide synthesizer (CEM, Matthews N.C.) using standard protocols with Rink amide resin, although other automated synthesizers without microwave capability may also be used. All amino acids were obtained from commercial sources unless otherwise noted. The coupling reagent used is 2-(6-chloro-1-H-benzotriazole-1yl)-1,1,3,3,-tetramethylaminium hexafluorophosphate (HCTU) and the base is diisopropylethylamine (DIEA). Peptides are cleaved from resin with 95% TFA, 2.5% TIS and 2.5% water for 3 hours and isolated by precipitation with ether. The crude peptides are purified on a reverse phase preparative HPLC using a C18 column, with an acetonitrile/water 0.1% TFA gradient from 20%-50% over 30 min. Fractions containing the pure peptide are collected and lyophilized and all peptides are analyzed by LC-MS.

Example 13

Dibromoxylene Cyclization

A 100 mL flask is charged with acetonitrile (12 mL) and water (24 mL) and is degassed with argon for about 5 min. Linear peptide (0.01 mmole) and 200 mM ammonium bicarbonate (6 mL) are added followed by at least one peptide (0.012 mmole) such as, but not limited to, 1,3-bis (bromomethyl)benzene, 1,2-bis(bromomethyl)benzene, 1,4- bis(bromomethyl)benzene, 2,6-bis(bromomethyl)pyridine, (E)-1,4-dibromobut-2-ene. The reaction mixture is stirred under argon at room temperature for approximately 2 hours and monitored by LC-MS. After the reaction is complete, the reaction solution is frozen and lyophilized. HPLC purification of the crude lyophilized product followed by lyophilization of fractions containing pure peptide results in the final cyclized product as a white power.

Example 14

Substituted Bis(Bromomethyl)Benzenes Cyclization

A 100 mL flask is charged with acetonitrile (12 mL) and water (24 mL) and is degassed with argon for about 5 min. Linear peptide (0.01 mmole) and 200 mM ammonium bicarbonate (6 mL) are added followed by a substituted bis(bromomethyl)benzene (0.012 mmole). The reaction mixture is stirred under argon at room temperature for approximately 2 hours and monitored by LC-MS. After the reaction is complete, the reaction solution is frozen and lyophilized. HPLC purification of the crude lyophilized product followed by lyophilization of fractions containing pure peptide results in the final cyclized product as a white power.

Example 15

Inhibitor Compounds Obtained by Alternate Cyclization Procedures

Plasma kallikrein inhibitors were synthesized according to one or more of the chemical reactions described in sections A, B and C of the present example. The resulting inhibitor compounds were tested for plasma kallikrein inhibitory activity as described in example 4. These compounds are listed in Table 9 along with the corresponding $IC_{50}$ data obtained.

A. Heck Reaction

As used herein, the term "Heck reaction" refers to a chemical reaction wherein an unsaturated halide (including, but not limited to a bromide) reacts with an alkene group as well as a base in the presence of a catalyst comprising palladium resulting in the formation of a substituted alkene (Mizoroki, T. et al., Arylation of olefin with aryl iodide catalyzed by palladium. Bulletin of the Chemical Society of Japan. 1971. 44(2):p 581). For peptide mimetic synthesis by Heck reaction, 300 mg of peptide containing resin (0.59 mmol/g) was treated with a solution of $DMF/H_2O/Et_3N$ (9:1:1; 10 mL), $Pd(OAc)_2$ (40 mg), $PPh_3$ (50 mg), $(nBu)_4NCl$ (45 mg) in one portion. The resulting suspension was agitated overnight at 37° C. and after this time, the resin was washed sequentially with DMF, MeOH, DCM and dried under a nitrogen gas flow. The Peptide was cleaved off from the resin with $TFA/H_2O(97:3)$ and purified by reverse phase HPLC. An example of one such reaction is presented in Scheme 4.

Scheme 4

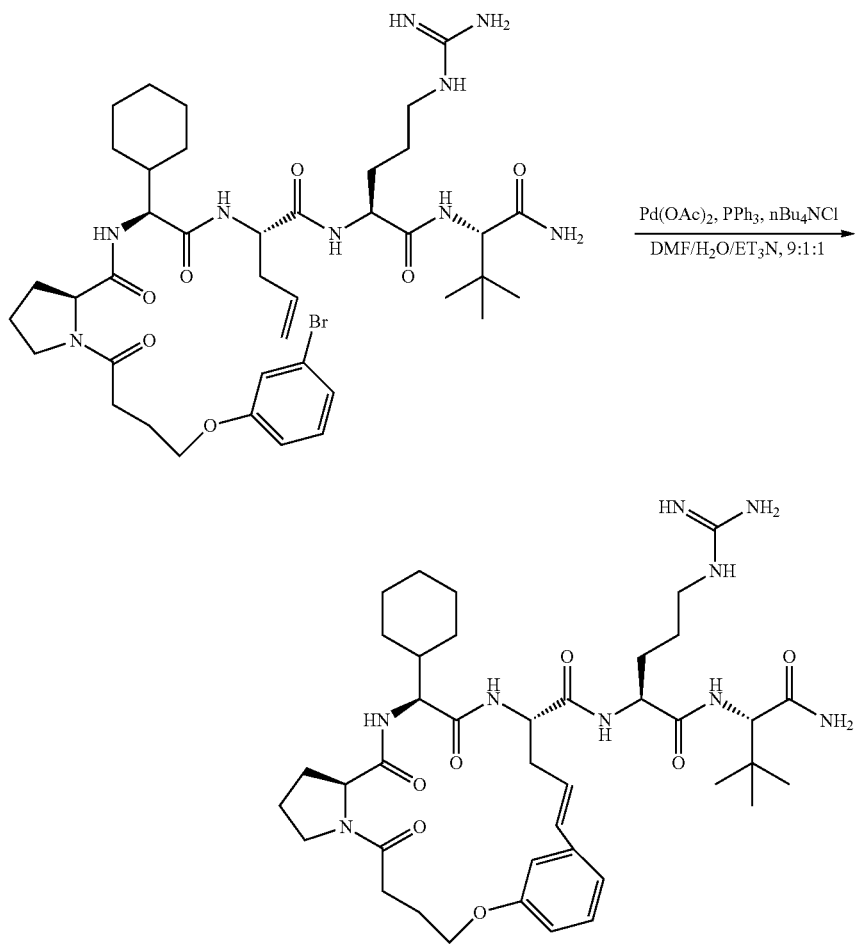

In some embodiments, the double bond formed in the reaction is in the S stereochemical formation. In some embodiments, the double bond formed in the reaction is in the R stereochemical formation.

B. Buchwald Reaction

As used herein, the term "Buchwald reaction" refers to a chemical reaction carried out overnight at a temperature selected from any between 50° C. and 150° C. wherein a halide (including, but not limited to a bromide) is reacted with a chemical group comprising oxygen in the presence of toluene and a catalyst comprising palladium. For peptide mimetic synthesis by Buchwald reaction, peptide containing resin (0.6 mmol/g) was treated with a solution of Toluene (10 mL), Pd(OAc)$_2$ (12 mg), ligand (7.9 mg), Cs$_2$CO$_3$ (32.5 mg) in 10 mL of Toluene in one portion. The resulting solution was agitated at 80° C. for 24 hr. The resin was washed sequentially with MeOH and DCM and dried under a nitrogen gas flow. The Peptide was cleaved off from the resin with TFA/H$_2$O(97:3) and purified by reverse phase HPLC. An example of one such reaction is presented in Scheme 5.

C. Olefin Metathesis

As used herein, the term "olefin metathesis" refers to a chemical reaction comprising alkene redistribution through the breaking and reforming of carbon-carbon double bonds. For peptide mimetic synthesis by olefin metathesis, peptide containing resin (0.6 mmol/g) and Grubbs-Hoveyda $2^{nd}$ catalyst (6.2 mg) were added into a reaction vessel and purged with nitrogen gas flow for 30 min. Anhydrous dichloroethane (1 mL) was then added, the vessel was sealed and the suspension was agitated at 80° C. for 40 hr. The resin was washed with DCM and dried under nitrogen gas flow. The Peptide was cleaved off from the resin with TFA/H$_2$O (97:3) and purified by reverse phase HPLC. An example of one such reaction is presented in Scheme 6.

Scheme 5

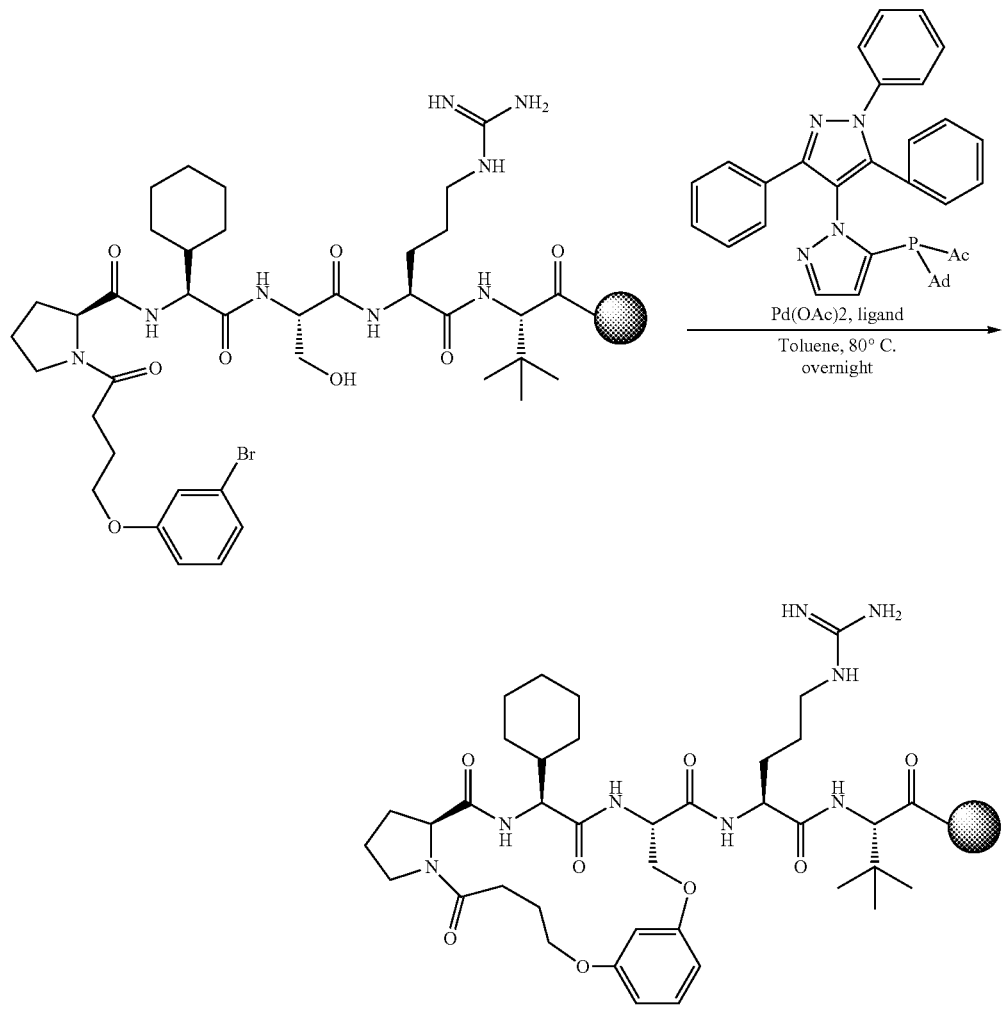

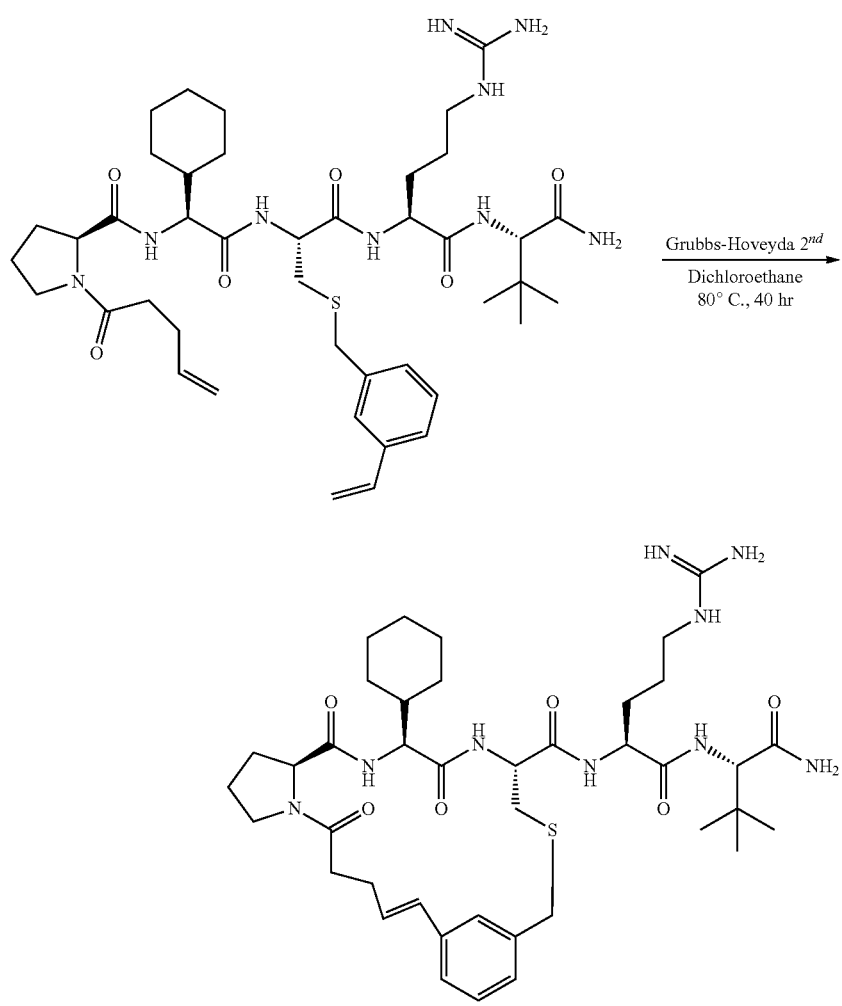
TABLE 9
Compounds synthesized using additional cyclization procedures
| Compound No. | Structure | Cyclic | Avg. IC$_{50}$ (nM) |
|---|---|---|---|
| R2240 | 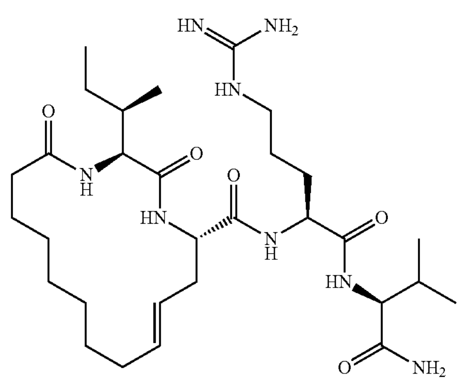 [SMILES: CC[C@@H](C)[C@@H]1NC(=O)CCCCCCC/C=C/C[C@@H](C(=O)N[C@@H](CCCNC(=N)N)C(=O)N[C@H](C(N)=O)C(C)C)NC1=O] | Yes | >75,000 |

TABLE 9-continued
Compounds synthesized using additional cyclization procedures
| Compound No. | Structure | Cyclic | Avg. IC$_{50}$ (nM) |
|---|---|---|---|
| R2241 | 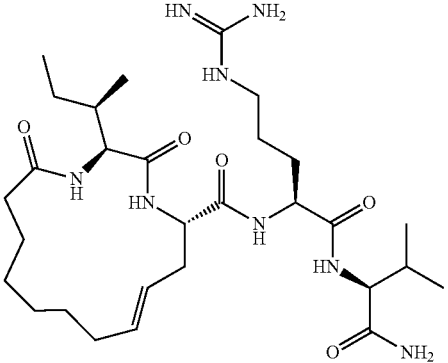 [SMILES: CC[C@@H](C)[C@@H]1NC(=O)CCCCCC/C=C/C[C@@H](C(=O)N[C@@H](CCCNC(=N)N)C(=O)N[C@H](C(N)=O)C(C)C)NC1=O] | Yes | >75,000 |
| R2242 | 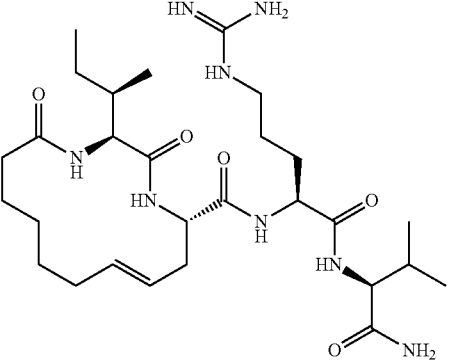 [SMILES: CC[C@@H](C)[C@@H]1NC(=O)CCCCC/C=C/C[C@@H](C(=O)N[C@@H](CCCNC(=N)N)C(=O)N[C@H](C(N)=O)C(C)C)NC1=O] | Yes | >100,000 |
| R2243 | 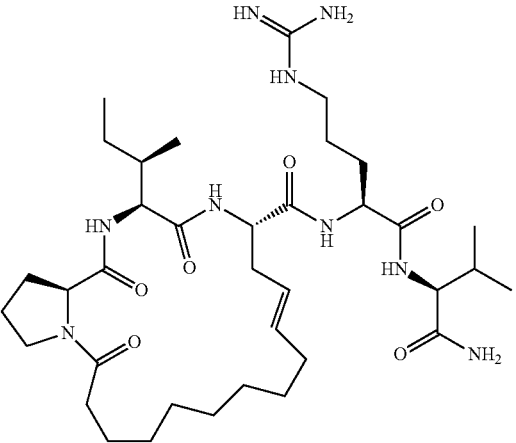 [SMILES: CC[C@@H](C)[C@@H]1NC(=O)[C@@H]2CCCN2C(=O)CCCCCCCC/C=C/C[C@@H](C(=O)N[C@@H](CCCNC(=N)N)C(=O)N[C@H](C(N)=O)C(C)C)NC1=O] | Yes | >50,000 |

TABLE 9-continued
Compounds synthesized using additional cyclization procedures
| Compound No. | Structure | Cyclic | Avg. IC$_{50}$ (nM) |
|---|---|---|---|
| R2244 | 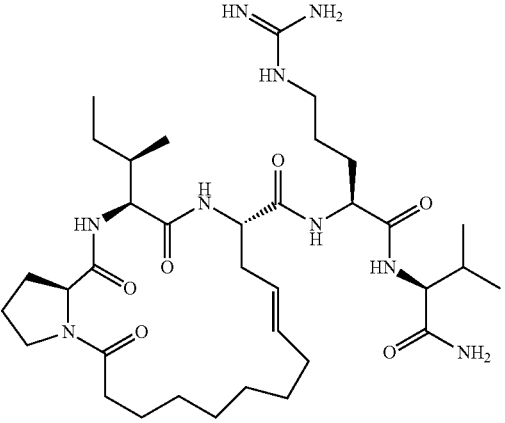 [SMILES: CC[C@@H](C)[C@@H]1NC(=O)[C@@H]2CCCN2C(=O)CCCCCCC/C=C/C[C@@H](C(=O)N[C@@H](CCCNC(=N)N)C(=O)N[C@H](C(N)=O)C(C)C)NC1=O] | Yes | >50,000 |
| R2245 | 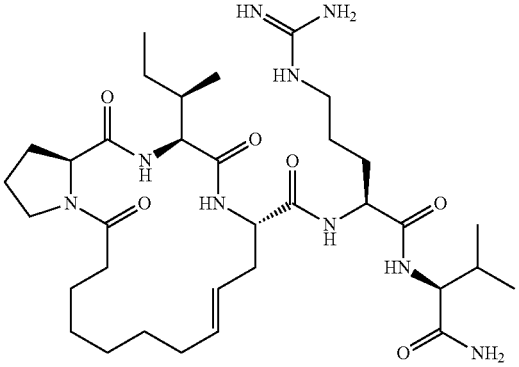 [SMILES: CC[C@@H](C)[C@@H]1NC(=O)[C@@H]2CCCN2C(=O)CCCCCC/C=C/C[C@@H](C(=O)N[C@@H](CCCNC(=N)N)C(=O)N[C@H](C(N)=O)C(C)C)NC1=O] | Yes | >50,000 |
| R2246 | 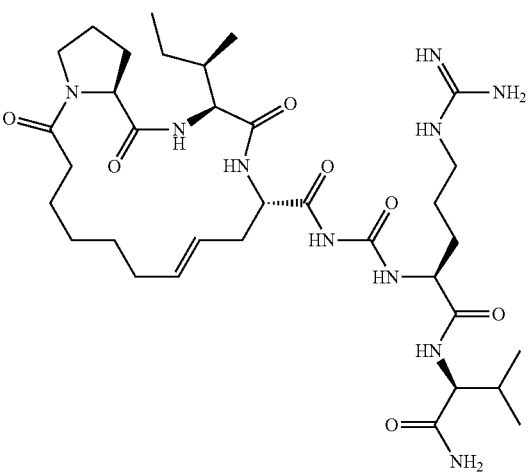 [SMILES: CC[C@@H](C)[C@@H]1NC(=O)[C@@H]2CCCN2C(=O)CCCCC/C=C/C[C@@H](C(=O)NC(=O)N[C@@H](CCCNC(=N)N)C(=O)N[C@H](C(N)=O)C(C)C)NC1=O] | Yes | >50,000 |

TABLE 9-continued

Compounds synthesized using additional cyclization procedures

| Compound No. | Structure | Cyclic | Avg. IC$_{50}$ (nM) |
|---|---|---|---|
| R2247 | 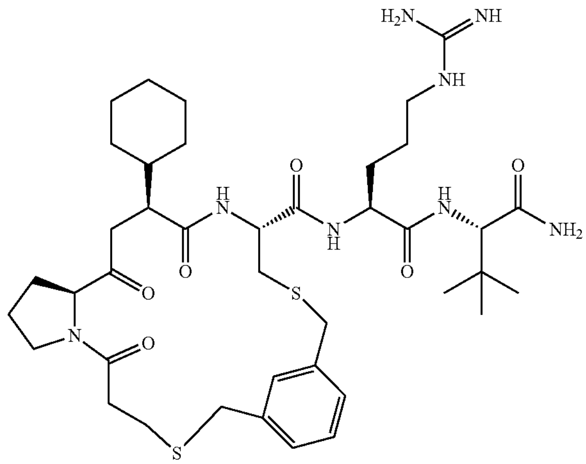 [SMILES: CC(C)(C)[C@H](NC(=O)[C@H](CCCNC(=N)N)NC(=O)[C@@H]1CSCc2cccc(c2)CSCCC(=O)N2CCC[C@H]2C(=O)C[C@@H](C2CCCCC2)C(=O)N1)C(N)=O] | Yes | 474 |
| R2248 | 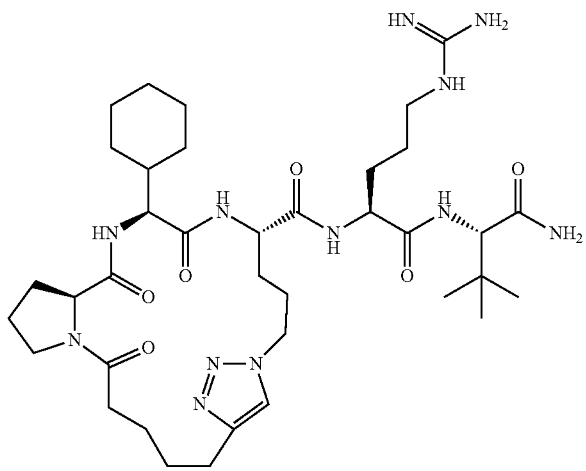 [SMILES: CC(C)(C)[C@H](NC(=O)[C@H](CCCNC(=N)N)NC(=O)[C@@H]1CCCn2cc(nn2)CCCCC(=O)N2CCC[C@H]2C(=O)N[C@@H](C2CCCCC2)C(=O)N1)C(N)=O] | Yes | 100,000 |
| R2249 | 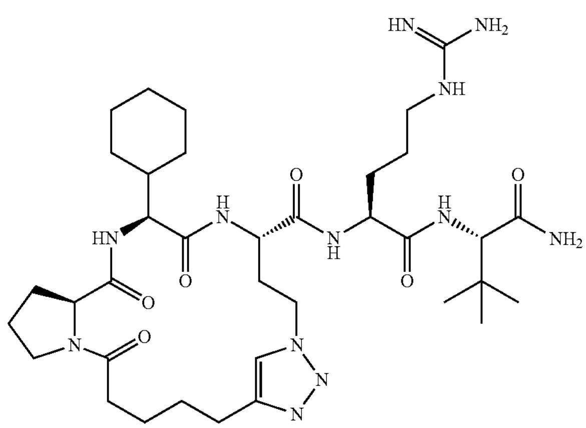 [SMILES: CC(C)(C)[C@H](NC(=O)[C@H](CCCNC(=N)N)NC(=O)[C@@H]1CCN2C=C(CCCCC(=O)N3CCC[C@H]3C(=O)N[C@@H](C3CCCCC3)C(=O)N1)NN2)C(N)=O] | Yes | >100,000 |

TABLE 9-continued
Compounds synthesized using additional cyclization procedures
| Compound No. | Structure | Cyclic | Avg. IC$_{50}$ (nM) |
|---|---|---|---|
| R2250 | 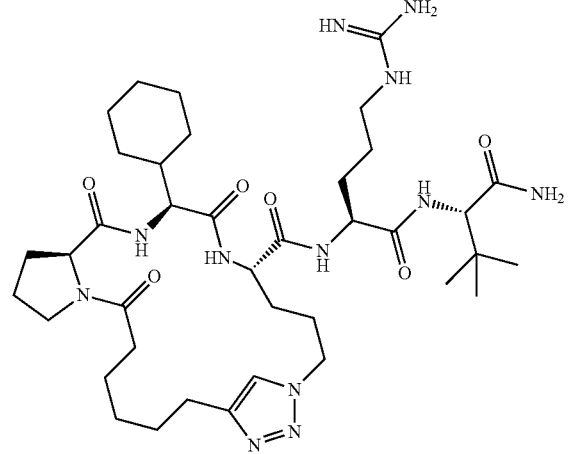 [SMILES: CC(C)(C)[C@H](NC(=O)[C@H](CCCNC(=N)N)NC(=O)[C@@H]1CCCn2cc(nn2)CCCCCC(=O)N2CCC[C@H]2C(=O)N[C@@H](C2CCCCC2)C(=O)N1)C(N)=O] | Yes | >100,000 |
| R2251 | 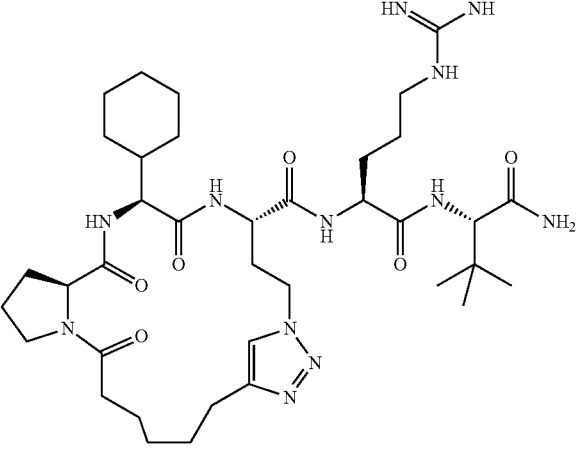 [SMILES: CC(C)(C)[C@H](NC(=O)[C@H](CCCNC(=N)N)NC(=O)[C@@H]1CCn2cc(nn2)CCCCCC(=O)N2CCC[C@H]2C(=O)N[C@@H](C2CCCCC2)C(=O)N1)C(N)=O] | Yes | >100,000 |
| R2252 | 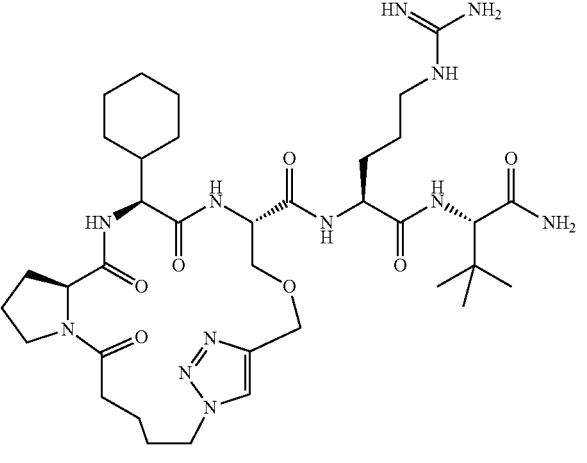 [SMILES: CC(C)(C)[C@H](NC(=O)[C@H](CCCNC(=N)N)NC(=O)[C@@H]1COCc2cn(nn2)CCCCC(=O)N2CCC[C@H]2C(=O)N[C@@H](C2CCCCC2)C(=O)N1)C(N)=O] | Yes | >100,000 |

TABLE 9-continued
Compounds synthesized using additional cyclization procedures
| Compound No. | Structure | Cyclic | Avg. IC$_{50}$ (nM) |
|---|---|---|---|
| R2253 | 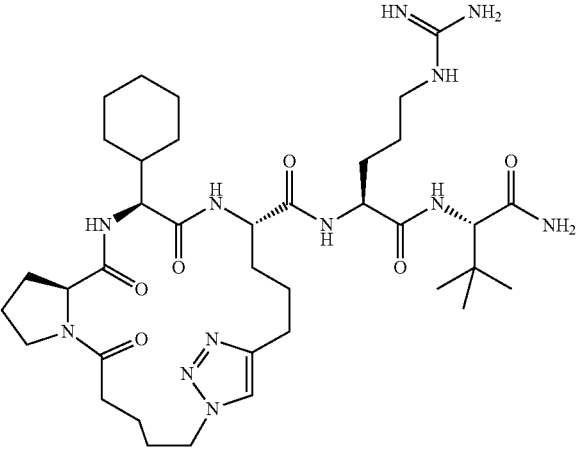 [SMILES: CC(C)(C)[C@H](NC(=O)[C@H](CCCNC(=N)N)NC(=O)[C@@H]1CCCc2cn(nn2)CCCCC(=O)N2CCC[C@H]2C(=O)N[C@@H](C2CCCCC2)C(=O)N1)C(N)=O] | Yes | >100,000 |
| R2254 | 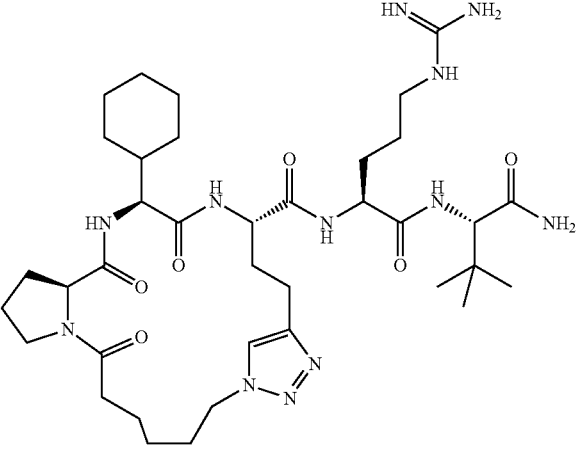 [SMILES: CC(C)(C)[C@H](NC(=O)[C@H](CCCNC(=N)N)NC(=O)[C@@H]1CCc2cn(nn2)CCCCCC(=O)N2CCC[C@H]2C(=O)N[C@@H](C2CCCCC2)C(=O)N1)C(N)=O] | Yes | >100,000 |
| R2255 | 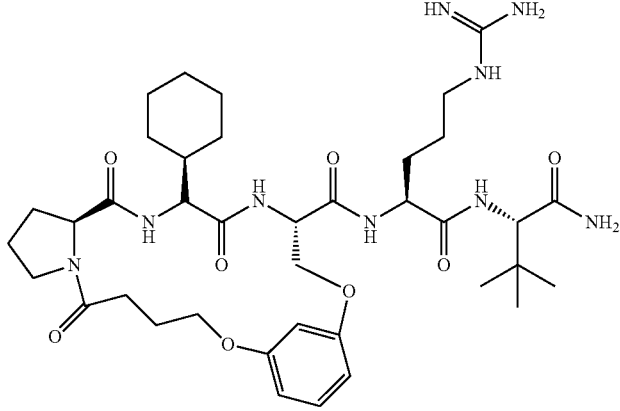 | Yes | >25,000 |

TABLE 9-continued
Compounds synthesized using additional cyclization procedures
| Compound No. | Structure | Cyclic | Avg. IC$_{50}$ (nM) |
|---|---|---|---|
| R2256 | 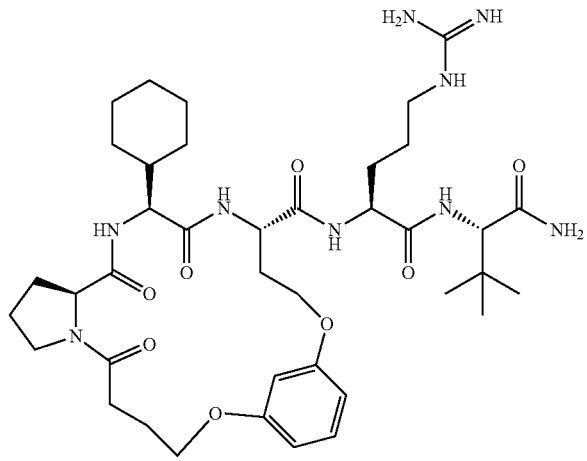 [SMILES: CC(C)(C)[C@H](NC(=O)[C@H](CCCNC(=N)N)NC(=O)[C@@H]1CCOc2cccc(c2)OCCCC(=O)N2CCC[C@H]2C(=O)N[C@@H](C2CCCCC2)C(=O)N1)C(N)=O] | Yes | >100000 |
| R2257 | 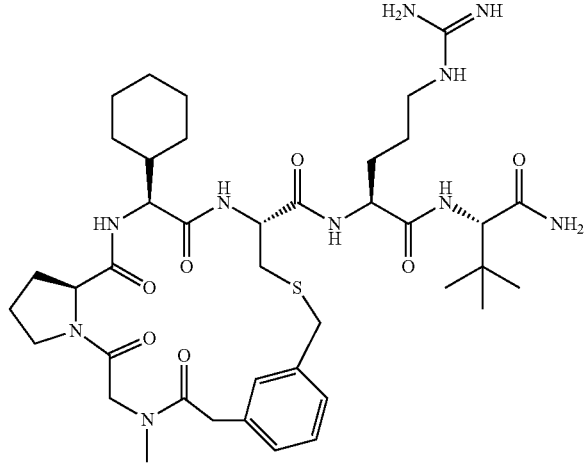 [SMILES: CN1CC(=O)N2CCC[C@H]2C(=O)N[C@@H](C2CCCCC2)C(=O)N[C@H](C(=O)N[C@@H](CCCNC(=N)N)C(=O)N[C@H](C(N)=O)C(C)(C)C)CSCc2cccc(c2)CC1=O] | Yes | 383.4 |
| R2258 | 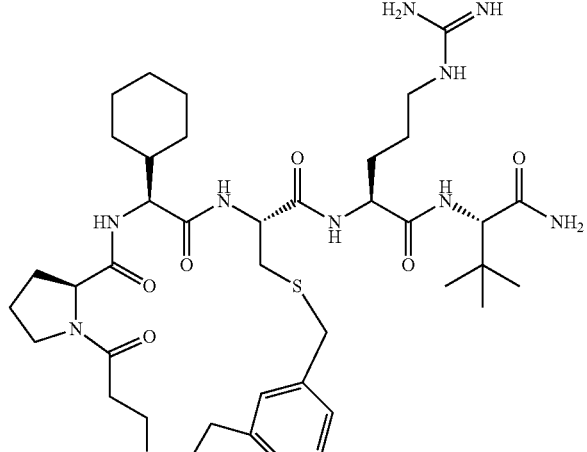 | Yes | 498 |

TABLE 9-continued
Compounds synthesized using additional cyclization procedures
| Compound No. | Structure | Cyclic | Avg. IC$_{50}$ (nM) |
|---|---|---|---|
| R2259 | 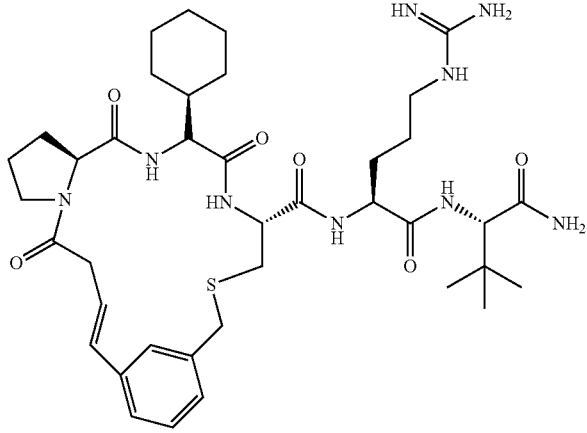 | Yes | 1456 |
| R2260 | 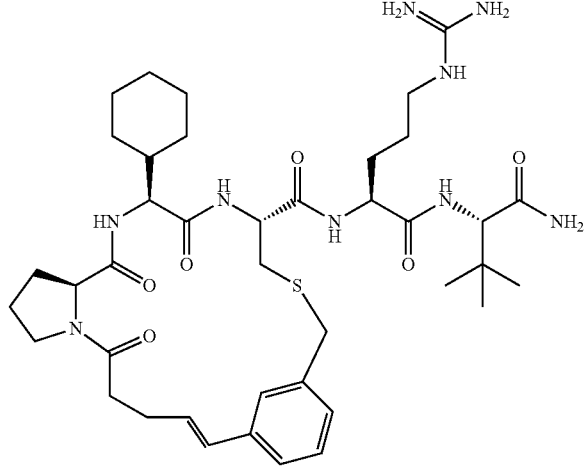 [SMILES: CC(C)(C)[C@H](NC(=O)[C@H](CCCNC(=N)N)NC(=O)[C@@H]1CSCc2cccc(c2)/C=C/CCC(=O)N2CCC[C@H]2C(=O)N[C@@H](C2CCCCC2)C(=O)N1)C(N)=O] | Yes | 4682 |
| R2261 | 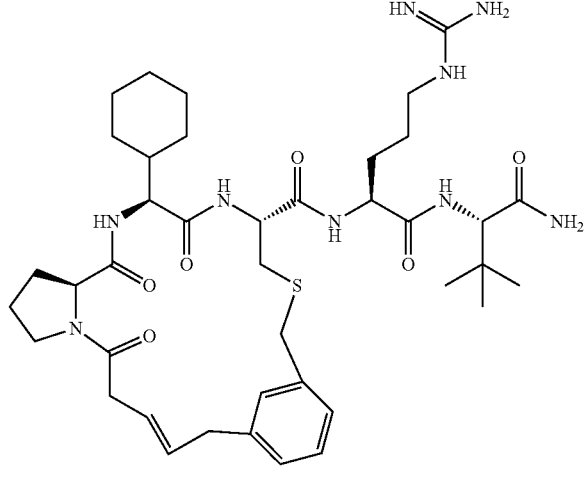 [SMILES: CC(C)(C)[C@H](NC(=O)[C@H](CCCNC(=N)N)NC(=O)[C@@H]1CSCc2cccc(c2)C/C=C/CC(=O)N2CCC[C@H]2C(=O)N[C@@H](C2CCCCC2)C(=O)N1)C(N)=O] | Yes | 164.2 |

TABLE 9-continued
Compounds synthesized using additional cyclization procedures
| Compound No. | Structure | Cyclic | Avg. IC$_{50}$ (nM) |
|---|---|---|---|
| R2262 | 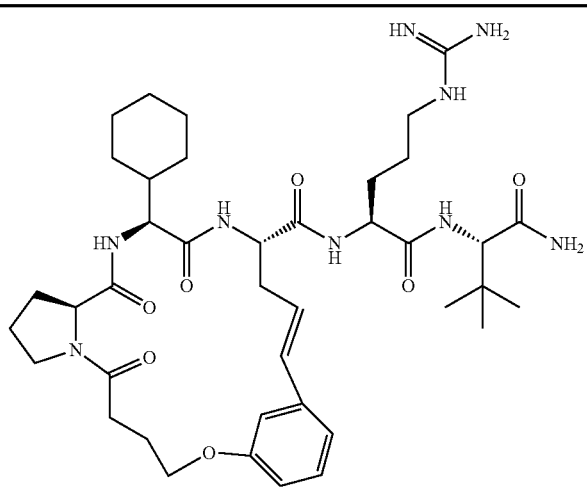 | Yes | >100000 |
| R2263 | 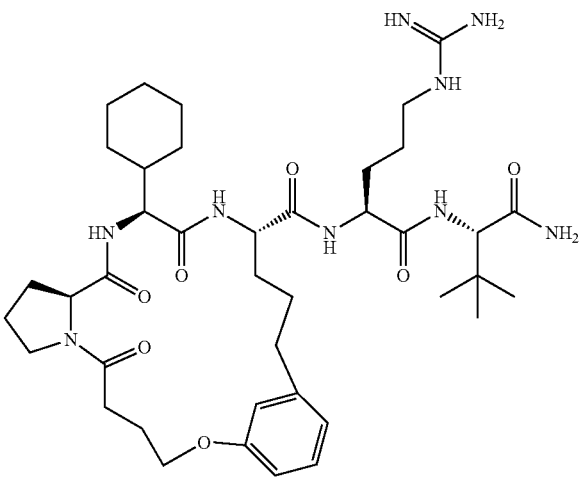 [SMILES: CC(C)(C)[C@H](NC(=O)[C@H](CCCNC(=N)N)NC(=O)[C@@H]1CCCc2cccc(c2)OCCCC(=O)N2CCC[C@H]2C(=O)N[C@@H](C2CCCCC2)C(=O)N1)C(N)=O] | Yes | >100000 |
| R2264 | 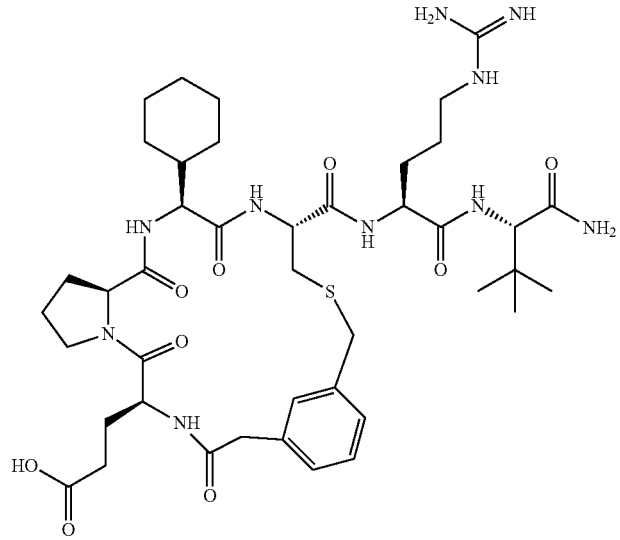 [SMILES: CC(C)(C)[C@H](NC(=O)[C@H](CCCNC(=N)N)NC(=O)[C@@H]1CSCc2cccc(c2)CC(=O)N[C@@H](CCC(=O)O)C(=O)N2CCC[C@H]2C(=O)N[C@@H](C2CCCCC2)C(=O)N1)C(N)=O] | Yes | 1103 |

TABLE 9-continued

Compounds synthesized using additional cyclization procedures

| Compound No. | Structure | Cyclic | Avg. IC$_{50}$ (nM) |
|---|---|---|---|
| R2265 | 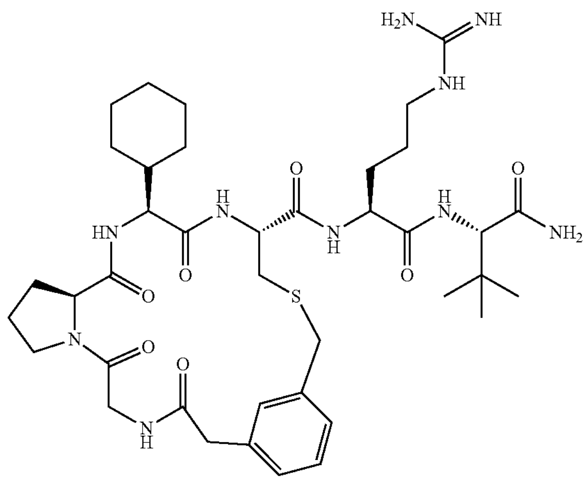 [SMILES: CC(C)(C)[C@H](NC(=O)[C@H](CCCNC(=N)N)NC(=O)[C@@H]1CSCc2cccc(c2)CC(=O)NCC(=O)N2CCC[C@H]2C(=O)N[C@@H](C2CCCCC2)C(=O)N1)C(N)=O] | Yes | 39.2 |
| R2266 | 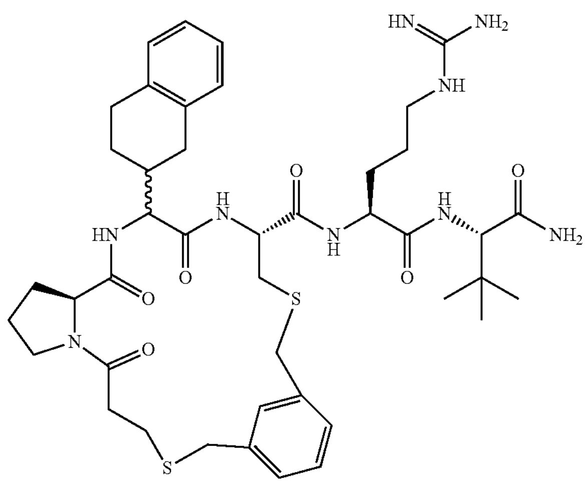 [SMILES: CC(C)(C)[C@H](NC(=O)[C@H](CCCNC(=N)N)NC(=O)[C@@H]1CSCc2cccc(c2)CSCCC(=O)N2CCC[C@H]2C(=O)NC(C2CCc3ccccc3C2)C(=O)N1)C(N)=O] | Yes | 118.4 |
| R2267 | 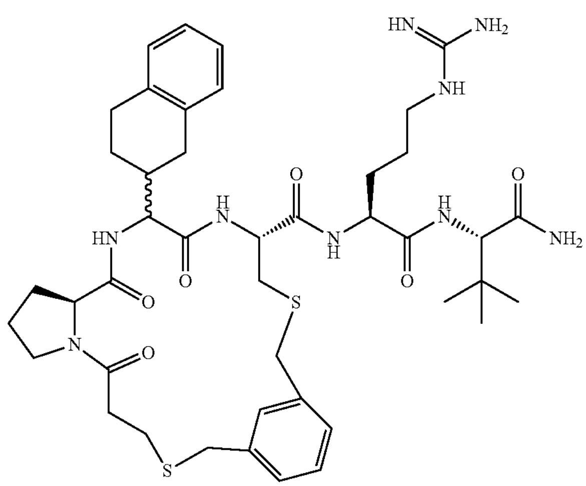 [SMILES: CC(C)(C)[C@H](NC(=O)[C@H](CCCNC(=N)N)NC(=O)[C@@H]1CSCc2cccc(c2)CSCCC(=O)N2CCC[C@H]2C(=O)NC(C2CCc3ccccc3C2)C(=O)N1)C(N)=O] | Yes | 12.8 |

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

What is claimed is:

1. A peptide comprising SEQ ID NO: 2 or an amino acid sequence having at least 80% homology to SEQ ID NO: 2.

2. The peptide of claim 1, wherein the peptide is cyclized with a reagent, thereby forming a cyclic peptide.

3. The cyclic peptide of claim 2, wherein the reagent is a thiol-reactive reagent.

4. The cyclic peptide of claim 3, wherein the thiol-reactive reagent is selected from the group consisting of: 1,2-bis(bromomethyl)benzene, 1,4-bis(bromomethyl)benzene, 2,6-bis(bromomethyl)pyridine, substituted bis(bromomethyl)benzenes and (E)-1,4-dibromobut-2-ene.

5. The cyclic peptide of claim 2, wherein the thiol-reactive reagent is 1,3-bis(bromomethyl)benzene.

6. The cyclic peptide of claim 2, wherein a loop is formed between two cysteine residues located at position 2 and position 6 of the cyclic peptide.

7. A method for the treatment of hereditary angioedema in a subject comprising the administration to said subject in need thereof of a therapeutically effective amount of a serine protease inhibitor, characterized in that the serine protease is plasma kallikrein and the serine protease inhibitor is a peptide or peptide mimetic comprising the amino acid sequence of SEQ ID NO: 2 or an amino acid sequence having 80% homology to SEQ ID NO: 2.

8. The method of claim 7, wherein administration is selected from the group consisting of oral, intravenous, intramuscular, intraperitoneal, subcutaneous, transdermal, and intravitreal.

9. The method of claim 8, wherein the inhibitor of plasma kallikrein is conjugated to a water soluble polymer.

10. The method of claim 9, wherein the water soluble polymer is a hydrophilic polymer.

11. The method of claim 10, wherein the hydrophilic polymer is selected from the group consisting of polyalkylene oxide homopolymers, polypropylene glycols, polyoxyethylenated polyols, and copolymers thereof.

12. The method of claim 11, wherein the water soluble polymer is polyethylene glycol (PEG).

13. A pharmaceutical composition comprising the cyclic peptide of claim 3 and a pharmaceutically acceptable carrier or excipient.

14. The cyclic peptide of claim 2, having kallikrein inhibitory activity with an $IC_{50}$ of less than 100 nM.

15. The cyclic peptide of claim 14 having an $IC_{50}$ of less than 50 nM against human kallikrein.

16. The cyclic peptide of claim 15 having an $IC_{50}$ of less than 10 nM against human kallikrein.

17. The cyclic peptide of claim 2, comprising one or more unnatural amino acids.

18. The cyclic peptide of claim 17, having kallikrein inhibitory activity and comprising at least one peptidic bond replacement, said at least one peptidic bond replacement being with a non-peptide moiety.

19. The cyclic peptide of claim 18, wherein the non-peptide moiety is selected from the group consisting of thioamide, sulfonamide, sulfonate, phosphonamide, phosphonate phosphothioate, phosphinate, alkane, 1 or 2 hydroxyethylene, dihydroxylethylene, C—C single bond (alkane), C—C double bond (alkene), C—C triple bond (alkyne), C—O bond (methyleneoxy), O—N or N—O bond, (methylenemino), triazole, hydrazide, urea, ketone, urethane bond, (di)haloalkene, methylenemercapto, methyleneamino, trifluoroethylamino, hydrazide and amideoxy.

20. The method of claim 7, wherein the method further comprises administering one or more additional inhibitors of plasma kallikrein.

* * * * *